US012611436B2

(12) United States Patent

Dismuke

(10) Patent No.: US 12,611,436 B2
(45) Date of Patent: *Apr. 28, 2026

---

(54) AAV TRANSFER CASSETTE

(71) Applicant: Sarepta Therapeutics, Inc., Cambridge, MA (US)

(72) Inventor: David Dismuke, Cary, NC (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 453 days.

This patent is subject to a terminal disclaimer.

(21) Appl. No.: 17/072,637

(22) Filed: Oct. 16, 2020

(65) Prior Publication Data

US 2021/0128652 A1 May 6, 2021

Related U.S. Application Data

(60) Provisional application No. 62/923,253, filed on Oct. 18, 2019, provisional application No. 62/916,749, filed on Oct. 17, 2019.

(51) Int. Cl.
| | |
|---|---|
| *A61K 35/761* | (2015.01) |
| *A61K 48/00* | (2006.01) |
| *A61P 25/28* | (2006.01) |
| *A61P 43/00* | (2006.01) |
| *C07K 14/705* | (2006.01) |
| *C12N 15/86* | (2006.01) |

(52) U.S. Cl.
CPC .......... *A61K 35/761* (2013.01); *A61K 48/005* (2013.01); *A61P 25/28* (2018.01); *A61P 43/00* (2018.01); *C07K 14/705* (2013.01); *C12N 15/86* (2013.01); *C12N 2750/14143* (2013.01)

(58) Field of Classification Search
CPC ........ A61K 35/761; C12N 15/86; A61P 25/28
See application file for complete search history.

(56) References Cited

U.S. PATENT DOCUMENTS

| | | |
|---|---|---|
| 4,039,388 A | 8/1977 | Gal et al. |
| 4,501,729 A | 2/1985 | Boucher et al. |
| 4,968,603 A | 11/1990 | Slamon et al. |
| 5,139,941 A | 8/1992 | Muzyczka et al. |
| 5,328,470 A | 7/1994 | Nabel et al. |
| 5,399,346 A | 3/1995 | Anderson et al. |
| 5,478,745 A | 12/1995 | Samulski et al. |
| 5,658,776 A | 8/1997 | Flotte et al. |
| 5,686,240 A | 11/1997 | Schuchman et al. |
| 5,863,541 A | 1/1999 | Samulski et al. |
| 5,869,248 A | 2/1999 | Yuan et al. |
| 5,877,022 A | 3/1999 | Stinchcomb et al. |
| 5,882,652 A | 3/1999 | Valdes et al. |
| 5,905,040 A | 5/1999 | Mazzara et al. |
| 5,916,563 A | 6/1999 | Young et al. |
| 5,962,313 A | 10/1999 | Podsakoff |
| 6,013,487 A | 1/2000 | Mitchell |
| 6,040,183 A | 3/2000 | Ferrari et al. |

| | | |
|---|---|---|
| 6,083,702 A | 7/2000 | Mitchell et al. |
| 6,093,570 A | 7/2000 | Ferrari et al. |
| 6,156,303 A | 12/2000 | Russell et al. |
| 6,180,613 B1 | 1/2001 | Kaplitt et al. |
| 6,426,198 B1 | 7/2002 | Carstea et al. |
| 6,468,524 B1 | 10/2002 | Chiorini et al. |
| 6,468,798 B1 | 10/2002 | Debs et al. |
| 6,503,888 B1 | 1/2003 | Kaplitt et al. |
| 6,544,785 B1 | 4/2003 | Palese et al. |
| 6,562,958 B1 | 5/2003 | Breton et al. |
| 6,733,757 B2 | 5/2004 | Patel et al. |
| 6,822,071 B1 | 11/2004 | Stephens et al. |
| 6,962,815 B2 | 11/2005 | Bartlett |
| 6,984,517 B1 | 1/2006 | Chiorini et al. |
| 7,045,675 B2 | 5/2006 | Carstea et al. |
| 7,071,172 B2 | 7/2006 | Mccown et al. |
| 7,105,345 B2 | 9/2006 | Wilson et al. |
| 7,198,951 B2 | 4/2007 | Gao et al. |
| 7,201,898 B2 | 4/2007 | Monahan et al. |
| 7,214,786 B2 | 5/2007 | Kovalic et al. |
| 7,252,997 B1 | 8/2007 | Hallek et al. |
| 7,259,151 B2 | 8/2007 | Arbetman et al. |
| 7,282,199 B2 | 10/2007 | Gao et al. |
| 7,314,912 B1 | 1/2008 | Hallek et al. |
| 7,473,531 B1 | 1/2009 | Dornon |

(Continued)

FOREIGN PATENT DOCUMENTS

| | | |
|---|---|---|
| EP | 1033405 A2 | 9/2000 |
| EP | 1777296 A2 | 4/2007 |

(Continued)

OTHER PUBLICATIONS

Wilmott et al (A User's Guide to the Inverted Terminal Repeats of Adeno-Associated Virus. Human Gene Therapy Methods, vol. 30, 2019). (Year: 2019).*
Xu et al (SV40 intron, a potent strong intron element that effectively increases transgene expression in transfected Chinese hamster ovary cells. J. Cell. Mol. Med., vol. 22, 2018). (Year: 2018).*
Addgene AAV guide (Year: 2023).*
NPC1: NINDS (Year: 2023).*
Issa (Various AAV Serotypes and Their Applications in Gene Therapy: An Overview. Cells 2023, 12, 785) (Year: 2023).*

(Continued)

*Primary Examiner* — Emily A Cordas
*Assistant Examiner* — Matasha Dhar
(74) *Attorney, Agent, or Firm* — STERNE, KESSLER, GOLDSTEIN & FOX P.L.L.C.

(57) ABSTRACT

Described herein are AAV transfer cassettes and plasmids used in the production of recombinant adeno-associated viral (rAAV) vectors. The disclosed cassettes and plasmids comprise one or more transgenes having therapeutic efficacy in the amelioration, treatment and/or prevention of one or more diseases or disorders, such as Niemann-Pick Disease, type C1 (NPC1).

4 Claims, 4 Drawing Sheets

Specification includes a Sequence Listing.

(56) References Cited

U.S. PATENT DOCUMENTS

| | | |
|---|---|---|
| 7,588,772 B2 | 9/2009 | Kay et al. |
| 7,712,893 B2 | 5/2010 | Dobashi |
| 7,718,424 B2 | 5/2010 | Chiorini et al. |
| 7,749,492 B2 | 7/2010 | Bartlett et al. |
| 7,777,097 B2 | 8/2010 | Glazebrook et al. |
| 7,790,449 B2 | 9/2010 | Gao et al. |
| 7,867,484 B2 | 1/2011 | Samulski et al. |
| 7,892,809 B2 | 2/2011 | Bowles et al. |
| 7,906,111 B2 | 3/2011 | Wilson et al. |
| 8,067,014 B2 | 11/2011 | Kay et al. |
| 8,299,321 B2 | 10/2012 | Cao |
| 8,318,480 B2 | 11/2012 | Gao et al. |
| 8,343,764 B2 | 1/2013 | Abad et al. |
| 8,445,267 B2 | 5/2013 | Zhong et al. |
| 8,628,966 B2 | 1/2014 | Chatterjee et al. |
| 8,664,475 B2 | 3/2014 | Puzio et al. |
| 8,679,837 B2 | 3/2014 | Zolotukhin et al. |
| 8,734,809 B2 | 5/2014 | Gao et al. |
| 8,802,440 B2 | 8/2014 | Zhong et al. |
| 8,889,641 B2 | 11/2014 | Asokan et al. |
| 8,906,387 B2 | 12/2014 | Kay et al. |
| 8,906,675 B2 | 12/2014 | Gao et al. |
| 8,927,514 B2 | 1/2015 | Chatterjee et al. |
| 8,952,217 B2 | 2/2015 | Puzio et al. |
| 8,962,332 B2 | 2/2015 | Gao et al. |
| 9,012,224 B2 | 4/2015 | Bowles et al. |
| 9,066,966 B2 | 6/2015 | Puccio et al. |
| 9,157,098 B2 | 10/2015 | Zhong et al. |
| 9,409,953 B2 | 8/2016 | Asokan et al. |
| 9,441,244 B2 | 9/2016 | Schaffer et al. |
| 9,475,845 B2 | 10/2016 | Asokan et al. |
| 9,567,376 B2 | 2/2017 | Cronin et al. |
| 9,585,971 B2 | 3/2017 | Deverman et al. |
| 9,587,250 B2 | 3/2017 | Gao et al. |
| 9,598,468 B2 | 3/2017 | Weigel-Van Aken et al. |
| 9,611,302 B2 | 4/2017 | Srivastava et al. |
| 9,623,120 B2 | 4/2017 | Chatterjee et al. |
| 9,677,088 B2 | 6/2017 | Nakai et al. |
| 9,677,089 B2 | 6/2017 | Gao et al. |
| 9,683,268 B2 | 6/2017 | Barouch et al. |
| 9,695,220 B2 | 7/2017 | Vandenberghe et al. |
| 9,719,070 B2 | 8/2017 | Vandenberghe et al. |
| 9,725,485 B2 | 8/2017 | Srivastava et al. |
| 9,737,618 B2 | 8/2017 | Wilson et al. |
| 9,737,619 B2 | 8/2017 | Ansell et al. |
| 9,775,918 B2 | 10/2017 | Zhong et al. |
| 9,777,291 B2 | 10/2017 | Chatterjee et al. |
| 9,783,825 B2 | 10/2017 | Chatterjee et al. |
| 9,790,472 B2 | 10/2017 | Gao et al. |
| 9,803,218 B2 | 10/2017 | Chatterjee et al. |
| 9,834,789 B2 | 12/2017 | Chatterjee et al. |
| 9,839,696 B2 | 12/2017 | Chatterjee et al. |
| 9,879,275 B2 | 1/2018 | Nadzan et al. |
| 9,890,396 B2 | 2/2018 | Chatterjee et al. |
| 9,909,142 B2 | 3/2018 | Yazicioglu et al. |
| 9,920,097 B2 | 3/2018 | Zhong et al. |
| 9,944,908 B2 | 4/2018 | Vaten et al. |
| 9,976,157 B2 | 5/2018 | Poraty-Gavra et al. |
| 10,011,640 B2 | 7/2018 | Srivastava et al. |
| 10,072,251 B2 | 9/2018 | Gao et al. |
| 10,077,291 B2 | 9/2018 | Asokan et al. |
| 10,081,659 B2 | 9/2018 | Chiorini et al. |
| 10,119,125 B2 | 11/2018 | Vandenberghe et al. |
| 10,214,566 B2 | 2/2019 | Schaffer et al. |
| 10,337,027 B2 | 7/2019 | Puccio et al. |
| 10,369,193 B2 | 8/2019 | Passini et al. |
| 10,385,320 B2 | 8/2019 | Kay et al. |
| 10,392,632 B2 | 8/2019 | Wright et al. |
| 10,406,244 B2 | 9/2019 | Kay et al. |
| 10,414,803 B2 | 9/2019 | Nathwani et al. |
| 10,426,844 B2 | 10/2019 | Agbandje-Mckenna et al. |
| 10,526,627 B2 | 1/2020 | Skuratowicz et al. |
| 10,668,094 B2 | 6/2020 | Karlish |
| 10,745,447 B2 | 8/2020 | Asokan et al. |
| 10,907,176 B2 | 2/2021 | Asokan et al. |
| 11,077,128 B2 | 8/2021 | Karlish |
| 11,208,438 B2 | 12/2021 | Asokan et al. |
| 2002/0192189 A1 | 12/2002 | Xiao et al. |
| 2003/0017131 A1 | 1/2003 | Park et al. |
| 2003/0053990 A1 | 3/2003 | Rabinowitz et al. |
| 2003/0225017 A1 | 12/2003 | Murdin et al. |
| 2004/0013645 A1 | 1/2004 | Monahan et al. |
| 2004/0031072 A1 | 2/2004 | La Rosa et al. |
| 2004/0071659 A1 | 4/2004 | Chang et al. |
| 2004/0166519 A1 | 8/2004 | Cargill et al. |
| 2004/0214272 A1 | 10/2004 | La Rosa et al. |
| 2005/0287122 A1 | 12/2005 | Bartlett et al. |
| 2006/0107345 A1 | 5/2006 | Alexandrov et al. |
| 2006/0123505 A1 | 6/2006 | Kikuchi et al. |
| 2006/0171926 A1 | 8/2006 | Passini et al. |
| 2006/0236419 A1 | 10/2006 | La Rosa et al. |
| 2007/0015238 A1 | 1/2007 | Snyder et al. |
| 2007/0124833 A1 | 5/2007 | Abad et al. |
| 2007/0196338 A1 | 8/2007 | Samulski et al. |
| 2007/0243526 A1 | 10/2007 | Kay et al. |
| 2008/0229439 A1 | 9/2008 | La Rosa et al. |
| 2009/0215879 A1 | 8/2009 | Diprimio et al. |
| 2009/0221620 A1 | 9/2009 | Luke et al. |
| 2009/0275107 A1 | 11/2009 | Lock et al. |
| 2009/0317417 A1 | 12/2009 | Vandenberghe et al. |
| 2010/0037352 A1 | 2/2010 | Alexandrov et al. |
| 2010/0047174 A1 | 2/2010 | Kay et al. |
| 2010/0095387 A1 | 4/2010 | Smith et al. |
| 2011/0061124 A1 | 3/2011 | Nadzan et al. |
| 2011/0067143 A2 | 3/2011 | La et al. |
| 2011/0124048 A1 | 5/2011 | Yun |
| 2011/0131679 A2 | 6/2011 | La et al. |
| 2011/0209246 A1 | 8/2011 | Kovalic et al. |
| 2011/0214206 A1 | 9/2011 | La Rosa et al. |
| 2011/0236353 A1 | 9/2011 | Wilson et al. |
| 2011/0294218 A1 | 12/2011 | Chatterjee et al. |
| 2012/0009268 A1 | 1/2012 | Asokan et al. |
| 2012/0137379 A1 | 5/2012 | Gao et al. |
| 2012/0216318 A1 | 8/2012 | La Rosa et al. |
| 2012/0255046 A1 | 10/2012 | Kay et al. |
| 2012/0322861 A1 | 12/2012 | Byrne et al. |
| 2013/0096182 A1 | 4/2013 | Chatterjee et al. |
| 2013/0152224 A1 | 6/2013 | Abad et al. |
| 2013/0185831 A1 | 7/2013 | Kovalic et al. |
| 2013/0195801 A1 | 8/2013 | Gao et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0225666 A1 | 8/2013 | Kaspar et al. |
| 2013/0326723 A1 | 12/2013 | La Rosa et al. |
| 2014/0017212 A1 | 1/2014 | Rebar |
| 2014/0037585 A1 | 2/2014 | Wright et al. |
| 2014/0050701 A1 | 2/2014 | Zhong et al. |
| 2014/0056854 A1 | 2/2014 | Asokan et al. |
| 2014/0057969 A1 | 2/2014 | Frost et al. |
| 2014/0130203 A1 | 5/2014 | La Rosa et al. |
| 2014/0162319 A2 | 6/2014 | Hareendran et al. |
| 2014/0199313 A1 | 7/2014 | Plesch et al. |
| 2014/0223605 A1 | 8/2014 | Puzio et al. |
| 2014/0259218 A1 | 9/2014 | Kovalic et al. |
| 2014/0296486 A1 | 10/2014 | Gao et al. |
| 2014/0335054 A1 | 11/2014 | Gao et al. |
| 2014/0341852 A1 | 11/2014 | Srivastava et al. |
| 2015/0050302 A1 | 2/2015 | Thess |
| 2015/0079038 A1 | 3/2015 | Deverman et al. |
| 2015/0082481 A1 | 3/2015 | La Rosa et al. |
| 2015/0126588 A1 | 5/2015 | Nakai et al. |
| 2015/0133530 A1 | 5/2015 | Srivastava et al. |
| 2015/0184189 A1 | 7/2015 | Abad et al. |
| 2015/0191739 A1 | 7/2015 | La Rosa et al. |
| 2015/0197763 A1 | 7/2015 | La Rosa et al. |
| 2015/0238550 A1 | 8/2015 | Mccown |
| 2015/0344911 A1 | 12/2015 | Chatterjee et al. |
| 2016/0017295 A1 | 1/2016 | Schaffer et al. |
| 2016/0025657 A1 | 1/2016 | Shahbazmohamadi et al. |
| 2016/0106865 A1 | 4/2016 | Zhong et al. |
| 2016/0215024 A1 | 7/2016 | Vandenberghe et al. |
| 2016/0222067 A1 | 8/2016 | Gao et al. |
| 2016/0256571 A1 | 9/2016 | Corral-Debrinski et al. |

(56) References Cited

U.S. PATENT DOCUMENTS

| | | |
|---|---|---|
| 2016/0264984 A1 | 9/2016 | La Rosa et al. |
| 2016/0289275 A1 | 10/2016 | Chiorini et al. |
| 2016/0319294 A1 | 11/2016 | Kovalic et al. |
| 2016/0333372 A1 | 11/2016 | Srivastava et al. |
| 2016/0361439 A1 | 12/2016 | Agbandje-Mckenna et al. |
| 2016/0369299 A1 | 12/2016 | Boye et al. |
| 2017/0007720 A1 | 1/2017 | Boye et al. |
| 2017/0028082 A1 | 2/2017 | Wilson et al. |
| 2017/0049910 A1 | 2/2017 | Cronin et al. |
| 2017/0067908 A1 | 3/2017 | Nakai et al. |
| 2017/0088852 A1 | 3/2017 | Dangoor et al. |
| 2017/0088858 A1 | 3/2017 | Gao et al. |
| 2017/0096683 A1 | 4/2017 | Scaria et al. |
| 2017/0130245 A1 | 5/2017 | Kotin et al. |
| 2017/0159027 A1 | 6/2017 | Wilson et al. |
| 2017/0204144 A1 | 7/2017 | Deverman et al. |
| 2017/0211092 A1 | 7/2017 | Chatterjee et al. |
| 2017/0211093 A1 | 7/2017 | Chatterjee et al. |
| 2017/0211094 A1 | 7/2017 | Chatterjee et al. |
| 2017/0211095 A1 | 7/2017 | Chatterjee et al. |
| 2017/0240885 A1 | 8/2017 | Deverman et al. |
| 2017/0275337 A1 | 9/2017 | Srivastava et al. |
| 2017/0298323 A1 | 10/2017 | Vandenberghe et al. |
| 2017/0349911 A1 | 12/2017 | Gao et al. |
| 2018/0002722 A1 | 1/2018 | Asokan et al. |
| 2018/0030096 A1 | 2/2018 | Aslanidi et al. |
| 2018/0030479 A1 | 2/2018 | Gao et al. |
| 2018/0036428 A1 | 2/2018 | Zhong et al. |
| 2018/0066022 A1 | 3/2018 | Chalberg et al. |
| 2018/0066285 A1 | 3/2018 | Ojala et al. |
| 2018/0104289 A1* | 4/2018 | Venditti ............... A61K 48/005 |
| 2018/0105559 A1 | 4/2018 | Srivastava et al. |
| 2018/0112229 A1 | 4/2018 | Nadzan et al. |
| 2018/0119167 A1 | 5/2018 | Abad et al. |
| 2018/0135074 A1 | 5/2018 | Srivastava et al. |
| 2018/0135076 A1 | 5/2018 | Linden |
| 2018/0163227 A1 | 6/2018 | Chatterjee et al. |
| 2018/0214576 A1 | 8/2018 | Fitzgerald et al. |
| 2018/0244727 A1 | 8/2018 | Zhong et al. |
| 2018/0265863 A1 | 9/2018 | Esteves et al. |
| 2018/0311290 A1* | 11/2018 | Sena-Esteves ....... C12N 9/2471 |
| 2018/0355376 A1 | 12/2018 | Chiorini et al. |
| 2018/0362592 A1 | 12/2018 | Gao et al. |
| 2018/0371024 A1 | 12/2018 | Asokan et al. |
| 2019/0048041 A1 | 2/2019 | Asokan et al. |
| 2019/0055524 A1 | 2/2019 | Vandenberghe et al. |
| 2019/0085301 A1 | 3/2019 | Gao et al. |
| 2019/0100560 A1 | 4/2019 | Vandenberghe et al. |
| 2019/0249195 A1 | 8/2019 | Marsic et al. |
| 2019/0255192 A1 | 8/2019 | Kirn et al. |
| 2019/0262373 A1 | 8/2019 | Woodard et al. |
| 2019/0284576 A1 | 9/2019 | Qu et al. |
| 2019/0292561 A1 | 9/2019 | Qu et al. |
| 2019/0367562 A1 | 12/2019 | Asokan et al. |
| 2020/0109418 A1 | 4/2020 | Li et al. |
| 2020/0399321 A1 | 12/2020 | Asokan et al. |
| 2021/0115474 A1 | 4/2021 | Mccoy et al. |
| 2021/0324418 A1 | 10/2021 | Thomas et al. |
| 2021/0363191 A1 | 11/2021 | Mccoy et al. |
| 2021/0371469 A1 | 12/2021 | Mccoy et al. |
| 2021/0371471 A1 | 12/2021 | Mccoy et al. |
| 2022/0056478 A1 | 2/2022 | O'Banion |
| 2022/0064675 A1 | 3/2022 | McCoy et al. |
| 2022/0088152 A1 | 3/2022 | Mikati |
| 2022/0089651 A1 | 3/2022 | Asokan et al. |

FOREIGN PATENT DOCUMENTS

| | | |
|---|---|---|
| EP | 1887081 A2 | 2/2008 |
| EP | 2194140 A2 | 6/2010 |
| EP | 2359869 A2 | 8/2011 |
| EP | 2492347 A1 | 8/2012 |
| EP | 2660325 A2 | 11/2013 |
| EP | 2315833 B1 | 4/2015 |
| EP | 1453547 B1 | 9/2016 |
| EP | 2007795 B1 | 11/2016 |
| EP | 2675484 B1 | 5/2018 |
| EP | 2263692 B1 | 9/2018 |
| EP | 2206728 B9 | 10/2018 |
| EP | 3244931 B1 | 10/2018 |
| EP | 1633767 B1 | 11/2018 |
| EP | 3060575 B1 | 12/2018 |
| EP | 3250239 B1 | 12/2018 |
| EP | 3459965 A1 | 3/2019 |
| EP | 3511021 A1 | 7/2019 |
| EP | 3108000 B1 | 8/2019 |
| JP | 2014534245 A | 12/2014 |
| RU | 2457252 C2 | 7/2012 |
| WO | WO-9005142 A1 | 5/1990 |
| WO | WO 98/11244 A2 | 3/1998 |
| WO | WO-9901555 A1 | 1/1999 |
| WO | WO 99/61601 A2 | 12/1999 |
| WO | WO 00/028061 A1 | 1/2000 |
| WO | WO 00/17377 A2 | 3/2000 |
| WO | WO-0023477 A2 | 4/2000 |
| WO | WO 00/28004 A1 | 5/2000 |
| WO | WO-0111034 A2 | 2/2001 |
| WO | WO-0181581 A2 | 11/2001 |
| WO | WO 01/92551 A2 | 12/2001 |
| WO | WO-0210210 A2 | 2/2002 |
| WO | WO-03000906 A2 | 1/2003 |
| WO | WO-03008540 A2 | 1/2003 |
| WO | WO-03033515 A1 | 4/2003 |
| WO | WO-03042361 A2 | 5/2003 |
| WO | WO-03052051 A2 | 6/2003 |
| WO | WO 03/095647 A2 | 11/2003 |
| WO | WO-2004027019 A2 | 4/2004 |
| WO | WO 2005/033321 A2 | 4/2005 |
| WO | WO 2006/021724 A2 | 3/2006 |
| WO | WO 2006/029319 A2 | 3/2006 |
| WO | WO 2006/066066 A2 | 6/2006 |
| WO | WO 2006/073052 A1 | 7/2006 |
| WO | WO-2006119137 A1 | 11/2006 |
| WO | WO-2006119432 | 11/2006 |
| WO | WO-2007084773 A2 | 7/2007 |
| WO | WO-2007089632 A2 | 8/2007 |
| WO | WO-2007092563 A2 | 8/2007 |
| WO | WO 2007/100465 A2 | 9/2007 |
| WO | WO-2007120542 A2 | 10/2007 |
| WO | WO-2007127264 A2 | 11/2007 |
| WO | WO 2008/088895 A2 | 7/2008 |
| WO | WO-2009037279 A1 | 3/2009 |
| WO | WO-2009043936 A1 | 4/2009 |
| WO | WO-2009105612 A2 | 8/2009 |
| WO | WO-2009108274 A2 | 9/2009 |
| WO | WO 2010/093784 | 8/2010 |
| WO | WO-2010129021 A1 | 11/2010 |
| WO | WO-2010138263 A2 | 12/2010 |
| WO | WO-2011020118 A1 | 2/2011 |
| WO | WO-2011020710 A2 | 2/2011 |
| WO | WO-2011122950 A1 | 10/2011 |
| WO | WO-2011133890 A1 | 10/2011 |
| WO | WO-2011140279 A1 | 11/2011 |
| WO | WO-2012061744 A2 | 5/2012 |
| WO | WO-2012064960 A2 | 5/2012 |
| WO | WO-2012112578 A2 | 8/2012 |
| WO | WO-2012178173 A1 | 12/2012 |
| WO | WO-2013016315 A1 | 1/2013 |
| WO | WO-2013027223 A2 | 2/2013 |
| WO | WO-2013158879 A1 | 10/2013 |
| WO | WO-2013170078 A1 | 11/2013 |
| WO | WO-2013173129 A2 | 11/2013 |
| WO | WO-2013173512 A2 | 11/2013 |
| WO | WO-2013190059 A1 | 12/2013 |
| WO | WO-2014007858 A1 | 1/2014 |
| WO | WO-2014045674 A1 | 3/2014 |
| WO | WO-2014124282 A1 | 8/2014 |
| WO | WO 2014/144229 | 9/2014 |
| WO | WO-2014153083 A1 | 9/2014 |
| WO | WO-2014193716 A2 | 12/2014 |
| WO | WO-2014194132 A1 | 12/2014 |
| WO | WO-2015013313 A2 | 1/2015 |
| WO | WO-2015038958 A1 | 3/2015 |
| WO | WO-2015054653 A2 | 4/2015 |

(56) References Cited

FOREIGN PATENT DOCUMENTS

| | | |
|---|---|---|
| WO | WO-2015121501 A1 | 8/2015 |
| WO | WO-2015164757 A1 | 10/2015 |
| WO | WO-2015168666 A2 | 11/2015 |
| WO | WO-2015173308 A1 | 11/2015 |
| WO | WO-2015181823 A1 | 12/2015 |
| WO | WO-2015191508 A1 | 12/2015 |
| WO | WO-2016054557 A1 | 4/2016 |
| WO | WO-2016065001 A1 | 4/2016 |
| WO | WO-2016081811 A1 | 5/2016 |
| WO | WO-2016115382 A1 | 7/2016 |
| WO | WO-2016115503 A1 | 7/2016 |
| WO | WO-2016128558 A1 | 8/2016 |
| WO | WO-2016128559 A1 | 8/2016 |
| WO | WO-2016134338 A1 | 8/2016 |
| WO | WO-2016150964 A1 | 9/2016 |
| WO | WO-2016164642 A1 | 10/2016 |
| WO | WO-2016172008 A1 | 10/2016 |
| WO | WO-2016172155 A1 | 10/2016 |
| WO | WO-2016179644 A1 | 11/2016 |
| WO | WO-2017015102 A1 | 1/2017 |
| WO | WO 2017/058892 | 4/2017 |
| WO | WO-2017066764 A2 | 4/2017 |
| WO | WO-2017070516 A1 | 4/2017 |
| WO | WO-2017077451 A1 | 5/2017 |
| WO | WO-2017096164 A1 | 6/2017 |
| WO | WO-2017106236 A1 | 6/2017 |
| WO | WO 2017/143100 A1 | 8/2017 |
| WO | WO-2017139643 A1 | 8/2017 |
| WO | WO-2017147123 A1 | 8/2017 |
| WO | WO-2017180854 A1 | 10/2017 |
| WO | WO-2017180976 A1 | 10/2017 |
| WO | WO-2017192750 A1 | 11/2017 |
| WO | WO-2017201248 A1 | 11/2017 |
| WO | WO-2018022608 A2 | 2/2018 |
| WO | WO-2018035213 A1 | 2/2018 |
| WO | WO-2018049226 A1 | 3/2018 |
| WO | WO-2018064624 A1 | 4/2018 |
| WO | WO-2018075798 A1 | 4/2018 |
| WO | WO-2018119330 A2 | 6/2018 |
| WO | WO-2018152333 A1 | 8/2018 |
| WO | WO-2018160582 A1 | 9/2018 |
| WO | WO-2018170310 A1 | 9/2018 |
| WO | WO-2018-204764 A1 | 11/2018 |
| WO | WO-2018209154 A1 | 11/2018 |
| WO | WO-2018215613 A1 | 11/2018 |
| WO | WO-2018226785 A1 | 12/2018 |
| WO | WO-2018237066 A1 | 12/2018 |
| WO | WO-2019006418 A2 | 1/2019 |
| WO | WO-2019025984 A1 | 2/2019 |
| WO | WO-2019141765 A1 | 7/2019 |
| WO | WO-2019168961 A1 | 9/2019 |
| WO | WO-2019169004 A1 | 9/2019 |
| WO | WO-2019169132 A1 | 9/2019 |
| WO | WO-2019173434 A1 | 9/2019 |
| WO | WO-2019173538 A1 | 9/2019 |
| WO | WO-2019178412 A1 | 9/2019 |
| WO | WO 2019/195444 A1 | 10/2019 |
| WO | WO-2019195423 A1 | 10/2019 |
| WO | WO-2019195449 A1 | 10/2019 |
| WO | WO-2019222444 A2 | 11/2019 |
| WO | WO-2020016318 A1 | 1/2020 |
| WO | WO-2020142653 | 7/2020 |
| WO | WO 2020/191300 | 9/2020 |
| WO | WO-2020232297 A1 | 11/2020 |

OTHER PUBLICATIONS

Gérard, P. Metabolism of Cholesterol and Bile Acids by the Gut Microbiota. Pathogens 2014, 3, 14-24 (Year: 2014).*
Mingozzi et al (Therapeutic in vivo gene transfer for genetic disease using AAV: progress and challenges. Nature Reviews Genetics, vol. 12, May 2011) (Year: 2011).*
Hudry et al (Therapeutic AAV Gene Transfer to the Nervous System: A Clinical Reality. Neuron 101, Mar. 6, 2019) (Year: 2019).*

ACS on STN, BD Registry, 1182714-10-8 [online] [retrieved on Apr. 30, 2019], 2009215879, Aug. 27, 2009, SEQ ID No. 7, 1 page.
ACS on STN, BD Registry, 1182714-97-1 [online] [retrieved on Apr. 30, 2019], 2009215879, Aug. 27, 2009, SEQ ID No. 210, 1 page.
Adachi, et al., "Drawing a high-resolution functional map of adeno-associated virus capsid by massively parallel sequencing." Nat Commun. (Jan. 2014); 5(1): 3075.
Agbandje et al. "The Structure of Human Parvovirus B19 at 8 A; Resolution" Virology 203(1):106-115 (1994).
Agbandje-Mckenna et al. "AAV Capsid Structure and Cell Interactions" Methods in Molecular Biology, 807:47-92 (2011).
Albright et al., "Mapping the Structural Determinants Required for AAVrh.10 Transport across the Blood-Brain Barrier," Molecular Therapy 26(2), p. 1-14 (2017).
Albright, "Modulation of Sialic Acid Dependence Influences the Central Nervous System Transduction Profile of Adeno-associated Viruses," Journal of Virology 93(11), pp. 1-15 (2019).
Altschul et al. "Basic Local Alignment Search Tool" Journal of Molecular Biology 215:403-410 (1990).
Altschul et al. "Local Alignment Statistics" Methods in Enzymology 266:460-480 (1996).
Altschul, SF et al., 'Issues in searching molecular sequence databases,' Nat. Genet., vol. 6, pp. 119-129, (Feb. 1994).
Andino et al. "AAV-mediated knockdown of phospholamban leads to improved contractility and calcium handling in cardiomyocytes" The Journal of Gene Medicine 10:132-142 (2008).
Arnold et al., "A calcium responsive element that regulates expression of two calcium binding proteins in Purkinje cells," Proc Natl Acad Sci USA 94(16):8842-8847 (1997).
Askoan et al. "Adeno-Associated Virus Type 2 Contains an Integrin a5 1 Binding Domain Essential for Viral Cell Entry" Journal of Virology, 80(18):8961-8969 (2006).
Asokan, et al., "Reengineering a receptor footprint of adeno-associated virus enables selective and systemic gene transfer to muscle", Nat Biotechnol, (Jan. 2010); 28(1): 79-82.
Asuri et al., Directed Evolution of adeno-associated Virus for Enhanced Gene Delivery and Gene Targeting in Human Pluripotent Stem Cells, Molecular Therapy, Nature Publishing Group GB 20(2):329-338 (2013).
Ballabh et al. "The blood-brain barrier: an overview: structure, regulation, and clinical implications" Neurobiology of Disease, 16:1-13 (2004).
Bantel-Schaal et al., "Adeno-associated virus type 5 exploits two different entry pathways in human embryo fibroblast," J Virology 73:939 (1999).
Bartlett, JS et al., 'Selective and Rapid Uptake of Adeno-Associated Virus Type 2 in Brain,' Hum. Gene Ther., 9(8):1181-1186, (May 1998).
Bell et al. "Identification of the Galactose Binding Domain of the Adeno-Associated Virus Serotype 9 Capsid" Journal of Virology, 86(13):7326-7333 (2012).
Bleker et al. "Mutational Analysis of Narrow Pores at the Fivefold Symmetry Axes of Adeno-Associated Virus Type 2 Capsids Reveals a Dual Role in Genome Packaging and Activation of Phospholipase A2 Activity" Journal of Virology, 79(4):2528-2540 (2005).
Bordoli et al. "Protein structure homology modeling using SWISS-MODEL workspace" Nature Protocols, 4(1):1-13 (2008).
Bowie, et al., "Deciphering the Message in Protein Sequences: Tolerance to Amino Acid Substitutions." Science (1990); 247: 1306-1310.
Bowles et al. "Phase 1 Gene Therapy for Duchenne Muscular Dystrophy Using a Translational Optimized AAV Vector" Molecular Therapy, 20(2):443-455 (2012).
Brichard et al. "The Tyrosinase Gene Codes for an Antigen Recognized by Autologous Cytolytic T Lymphocytes on HLA-AZ Melanomas" Journal of Experimental Medicine178:489-495 (1993).
Brown et al. "Chimeric Parvovirus 19 Capsids for the Presentation of Foreign Epitopes" Virology 198(2):477-488 (1994).
Brown et al. "Erythrocyte P Antigen: Cellular Receptor for B19 Parvovirus" Science 262(5130):114-117 (1993).

(56)          References Cited

OTHER PUBLICATIONS

Carrillo-Tripp et al. "VIPERdb2: an enhanced and web API enabled relational database for structural virology" Nucleic Acids Research, 37:D436-D442 (2009).

Carstea, ED et al. 'Niemann-Pick C1 Disease Gene: Homology to Mediators of Cholesterol Homeostasis,' Science, 277(5323): 228-231 (Jul. 1997).

Cearley, C.N. et al. (2008). "Expanded repertoire of AAV vector serotypes mediate unique patterns of transduction in mouse brain," Mol. Ther. 16:1710-1718.

Cearley et al. "Transduction Characteristics of Adeno-associated Virus Vectors Expressing Cap Serotypes 7, 8, 9, and Rh10 in the Mouse Brain" Molecular Therapy, 13(3):528-537 (2006).

Chapman et al. "Structure, Sequence, and Function Correlations among Parvoviruses" Virology 194(2):491-508 (1993).

Chen et al. "Efficient Transduction of Vascular Endothelial Cells with Recombinant Adeno-Associated Virus Serotype 1 and 5 Vectors" Human Gene Therapy, 16(2):235-247 (2005).

Chen, SH et al., 'Gene therapy for brain tumors: Regression of experimental gliomas by adenovirus-mediated gene transfer in vivo,' Proc. Natl Acad. Sci. USA, vol. 91, pp. 3054-3057, (Apr. 1994).

Choi et al., "Optimization of AAV expression cassettes to improve packaging capacity and transgene expression in neurons," Molecular Brain, Biomed Central LTD, London UK, 7(1):17 p. f1729s 1-10 (2014).

Clark, KR et al., 'Highly Purified Recombinant Adeno-Associated Virus Vectors Are Biologically Active and Free of Detectable Helper and Wild-Type Viruses,' Hum. Gene Ther., 10(6):1031-1039, (Apr. 1999).

Corpet, F et al., 'Multiple sequence alignment with hierarchical clustering,' vol. 16 No. 22, pp. 10881-10890, (Oct. 1988).

Cotmore et al.,"The Family Parvoviridae," Archives of Virology 159:1239-1247 (2014).

DataBase GenBank: ABS91093.1, Aug. 10, 2007, [online] [retrieved on Feb. 14, 2020] Retrieved from Internet: https://www.ncbi.nlm.nih.gov/protein/ABS91093.1.

DataBase GenBank: ACW56705.1, Sep. 24, 2009, [online] [retrieved on May 7, 2019] Retrieved from Internet:https://www.ncbi.nlm.nih.gov/protein/ACW56705.1?report=genbank&log$=prottop&blast_rank= 1&RID=D2CZ8TP9014, 1 page.

De Jesus et al., "Telomerase gene therapy in adult and old mice delays aging and increases longevity without increasing cancer," EMBO Mol. Med. 4(8): 691-704 (2012).

Devereux et al. "A comprehensive set of sequence analysis programs for the VAX" Nucleic Acids Research 12(1):387-395 (1984).

Deverman, BE, Cre-dependent selection yields AAV variants for widespread gene transfer to the adult brain, Nat. Biotechnol., 34(2) :204-209. doi: 10.1038/nbt.3440. PubMed PMID: 26829320 (Epub Feb. 1, 2016).

Dipasquale et al. "Identification of PDGFR as a receptor for MV-5 transduction" Nature Medicine, 9:1306-1312 (2003). (Abstract only).

Diprimo, et al., "Surface loop dynamics in adeno-associated virus capsid assembly", Journal of Virology (2008); vol. 82, No. 11, pp. 5178-5189.

Emsley et al. "Features and development of Coot" Acta Crystallographica Section D: Biological Crystallography, D66:486-501 (2010).

European Search Report for European Application No. EP19760157.8 dated Nov. 18, 2021, 6 pages.

Extended European Search Report corresponding to European Patent Application No. 16737901.5 (6 pages). (dated May 15, 2018).

Extended European Search Report corresponding to European Patent Application No. 20212583.7, dated May 3, 2021, 10 pages.

Extended European Search Report issued by the European Patent Office for Application No. 16852471.8, dated Juy 29, 2019, 13 pages.

Extended European Search Report issued by the European Patent Office for U.S. Appl. No. 18/754,551, dated Jun. 4, 2021, 11 pages.

Felsenstein, Joseph "Confidence Limits on Phylogenies: An Approach Using the Bootstrap" Evolution, 39 (4):783-791 (1985).

Ferrari et al. "New developments in the generation of Ad-free high-titer rAAV gene therapy vectors" Nature Medicine 3(11):1295-1297 (1997).

Fisher, KJ et al., 'Transduction with Recombinant Adeno-Associated Virus for Gene Therapy Is Limited by Leading-Strand Synthesis,' J. Virol., 70(1):520-532 (LFU assay) (Jan. 1996).

Foster et al., "Emerging Immunotherapies for Authoimmune Kidney Disease," Hyman Vaccines & Immunotherapeutics 15(4):876-890 (2019).

Foust et al. "Intravascular AAV9 preferentially targets neonatal neurons and adult astrocytes" Nature Biotechnology, 27(1):59-65 (2009).

Gao et al. "Adeno-associated viruses undergo substantial evolution in primates during natural infections" Proceedings of the National Academy of Sciences, 100(10):6081-6086 (2003).

Gao et al. "Clades of adeno-Associated Vires are Widely Disseminated in Human Tissues" Journal of Virology 78(12):6381-6388 (2004).

Genbank Accession No. AF085716, Adeno-associated virus 5 DNA binding trs helicase (Rep22) and capsid protein (VP1) genes, complete cds., dated Feb. 9, 1999, 3 pages.

GenBank Accession No. AF258783.1 'Felis catus Niemann-Pick type C1 disease protein (NPC1) mRNA, complete eds' (2000).

Genbank Accession No. AY243001, Non-Human Primate Adeno-associated Virus Isolate AAVrh.34 capsid protein (VP1) gene, complete cds., dated May 14, 2003, 2 pages.

GenBank Accession No. BC045895 'Dania rerio Niemann-Pick disease, type C2, mRNA (cDNA clone MGC:56070 IMAGE:5409780), complete eds' (2003).

GenBank Accession No. BC054539 'Mus musculus Niemann Pick type C1, mRNA (cDNA clone MGC:62352 IMAGE:6405214), complete eds' (2006).

GenBank Accession No. BC090541 'Dania rerio Niemann-Pick disease, type C1, mRNA (cDNA clone IMAGE:7149020), partial eds' (2016).

GenBank Accession No. BC102504 'Bos taurus Niemann-Pick disease, type C2, mRNA (cDNA clone MGC: 127986 IMAGE:7954223), complete eds' (2007).

GenBank Accession No. BC117178 'Homo sapiens NPC1 (Niemann-Pick disease, type C1, gene)-like 1, mRNA (cDNA clone MGC:150787 IMAGE:40125729), complete eds' (2006).

GenBank Accession No. BC143756 'Homo sapiens NPC1 (Niemann-Pick disease, type C1, gene)-like 1, mRNA (cDNA clone MGC:177287 IMAGE:9052270), complete eds' (2009).

GenBank Accession No. BC151276 'Bos taurus Niemann-Pick disease, type C1, mRNA (cDNA clone MGC: 152602 IMAGE:8433293), complete eds '(2007).

GenBank Accession No. KJ893081 'Synthetic construct Homo sapiens clone ccsb Broad En_02475 NPC2 qene, encodes complete protein' (2015).

GenBank Accession No. NM 000271.4 'Homo sapiens cholesterol transporter 1 (NPC1), mRNA' (2017).

GenBank Accession No. NM 008720.2 'Mus musculus cholesterol transporter 1 (Npc1), mRNA' (2017).

GenBank Accession No. NM 023409.4 'Mus musculus NPC intracellular cholesterol transporter 2 (Npc2 mRNA' (2017).

GenBank Accession No. NM_006432.3 'Homo sapiens NPC intracellular cholesterol transporter 2 (NPC2), mRNA' (2017).

Gonzales, "Cross-Species Evolution of Synthetic AAV Strains for clinical Translation," ASGCT, 23 pages. (2020).

Gorman et al. "Stable alteration of pre-mRNA splicing patterns by modified U7 small nuclear RNAs" Proceedings of the National Academy of Sciences 95:4929:4934 (1998).

Gray et al. "Preclinical Differences of Intravascular MV9 Delivery to Neurons and Glia: A Comparative Study of Adult Mice and Nonhuman Primates" Molecular Therapy, 19(6):1058-1069 (2011).

Grieger, et al., "Separate Basic Region Motifs within the Adeno-Associated Virus Capsid Proteins Are Essential for Infectivity and Assembly." J. Virol. (2006), 80(11): 5199-5210.

(56) References Cited

OTHER PUBLICATIONS

Grimm D., et al., "In Vitro and in Vivo Gene Therapy Vector Evolution Via Multispecies Interbreeding and Retargeting of Adeno-Associated Viruses," Journal of Virology, Jun. 2008, vol. 82(12), pp. 5887-5911, XP002610286.

Gurda et al., "Mapping a Neutralizing Epitope onto the Capsid of Adeno-Associated Virus Serotype 8," Journal of Virology 86(15): 7739-7751 (2012).

Hadaczek et al. "Transduction of Nonhuman Primate Brain with Adeno-Associated Virus Serotype 1: Vector Trafficking and Immune Response" Human Gene Therapy, 20(3):225-237 (2009).

Hajitou et al., "Vascular targeting: recent advances and therapeutic perspectives," TCM 16:80-88 (2006).

Havlik, Engineering A Humanized AAV8 Capsid Through Iterative Structure-Guided Evolution ASGCT, 24 pages. (2019).

Havlik et al., "Co-Evolution of AAV Capsid Antigenicity and Tropism Through a Structure-Guided Approach," ASGCT, 39 pages (2020).

Higgins, Desmond G., and Sharp, Paul M. "Clustal: a package for performing multiple sequence alignment on a microcomputer." Gene (1988); 73.1: 237-244.

Higgins, DG et al., 'Fast and sensitive multiple sequence alignments on a microcomputer,' Comput Appl Biosci., 5(2):151-3, (Apr. 1989).

Hoshijima et al. "Chronic suppression of heart-failure progression by a pseudo phosphorylated mutant of phospholamban via in vivo cardiac rAAV gene delivery" Nature Medicine 8:864-871 (2002).

Huang et al. "Characterization of the adeno-Associated Virus 1 and 6 Sialic Acid Binding Site" Journal of Virology, 9 (11):5219-5230 (2016).

Huang, X et al., 'Dynamic programming algorithms for restriction map comparison,' Cabios, Vol.8, No. 5., pp. 511-520, (1992).

Hughes et al., "AAV9 intracerebroventricular gene therapy improves lifespan, locomotor function and pathology in a mouse model of Niemann-Pick type C1 disease," Human Molecular Genetics 27(17)3079-3098 (2018).

International Search Report and the Written Opinion of the International Searching Authority corresponding to International Patent Application No. PCT/2018/018381 (14 pages) (mailed Jul. 5, 2018).

International Search Report and the Written Opinion of the International Searching Authority corresponding to International Patent Application No. PCT/US2019/020053 (10 pages) (mailed Jun. 6, 2019).

International Search Report and Written Opinion issued by the International Searching Authority for Application No. PCT/2016/013460, dated May 12, 2016, 11 pages.

International Search Report and Written Opinion issued by the International Searching Authority for Application No. PCT/2016/054143, dated Mar. 23, 2017, 33 pages.

International Search Report and Written Opinion issued by the International Searching Authority for Application No. PCT/2020/023877, dated Aug. 3, 2020, 21 pages.

International Search Report and Written Opinion issued by the International Searching Authority for Application No. PCT/US20/15386, dated Apr. 27, 2020, 14 pages.

International Search Report and Written Opinion issued by the International Searching Authority for Application No. PCT/US2016/026524, dated Jan. 9, 2016, 10 pages.

International Search Report and Written Opinion issued by the International Searching Authority for Application No. PCT/US2018/038584 dated Aug. 24, 2018, 11 pages.

International Search Report and Written Opinion issued by the International Searching Authority for Application No. PCT/US2019/062531, dated Apr. 1, 2020, 12 pages.

International Search Report and Written Opinion issued by the International Searching Authority for Application No. PCT/US2020/032978, dated Oct. 15, 2020, 14 pages.

International Search Report and Written Opinion issued by the International Searching Authority for Application No. PCT/US2020/056015, dated Feb. 12, 2021, 17 pages.

International Search Report and Written Opinion issued by the International Searching Authority for Application No. PCT/US2020/056031, dated Feb. 15, 2021, 18 pages.

International Search Report and Written Opinion issued by the International Searching Authority for Application No. PCT/US2021/030937, dated Oct. 29, 2021, 14 pages.

International Search Report of International PCT/US2016/026524, mailed Sep. 1, 2016.

Invitation to Pay issued by the International Searching Authority for Application No. PCT/US21/30937, dated Aug. 16, 2021, 3 pages.

Invitation to Pay issued by the International Searching Authority for Application No. PCT/US2019/062531, dated Feb. 3, 2020, 2 pages.

Janson, C. et al., 'Clinical protocol. Gene therapy of Canavan disease: AAV-2 vector for neurosurgical delivery of aspartoacylase gene (ASPA) to the human brain,' Hum. Gene Ther., 13(11):1391-1412 (Jul. 2002).

Kaplitt, M.G. et al. (1994). "Long-term gene expression and phenotypic correction using adeno-associated virus vectors in the mammalian brain," Nature Genetics 6:148-154.

Kashiwakura et al. "Hepatocyte Growth Factor Receptor Is a Coreceptor for Adeno-Associated Virus Type 2 Infection" Journal of Virology, 79(1).609-614 (2005).

Kauffman et al., "Mechanism Matters: A Taxonomy of Cell Penetrating Peptides," Trends in Biochemical Sciences, Elsevier, Amsterdam, NL 40(12):749-764 (2015).

Krissinel et al. "Secondary-structure matching (SSM)., a new tool for fast protein structure alignment in three dimensions" Acta Crystallographica Section D: Biological Crystallography, D60:2256-2268 (2004).

Kumar et al. "MEGA7: Molecular Evolutionary Genetics Analysis Version 7.0 for Bigger Datasets" Molecular Biology and Evolution, 33(7):1870-1874 (2016).

Lein et al. "Genome-wide atlas of gene expression in the adult mouse brain" Nature, 445(7124):168-176 (2007). (Abstract only).

Levine et al. "The Tumor Suppressor Genes" Annual Review of Biochemistry 62:623-651 (1993).

Li et al. "Development of Patient-specific AAV Vectors After Neutralizing Antibody Selection for Enhanced Muscle Gene Transfer" Molecular Therapy, 24(1):53-65 (2016).

Li et al. "Engineering and Selection of Shuffled AAV Genomes: A New Strategy for Producing Targeted Biological Nanoparticles" Molecular Therapy, 16(7):1252-1260 (2008).

Li et al. "Single Amino Acid Modification of adeno-Associated Virus Capsid Changes Transduction and Humeral Immune Profiles" Journal of Virology, 86(15):7752-7759 (2012).

Lisowski L., et al., "Selection and Evaluation of Clinically Relevant AAV Variants in a Xenograft Liver Model," Nature, Feb. 2014, vol. 506 (7488), pp. 382-386, XP055573596.

Loftus, SK et al., 'Murine Model of Niemann-Pick C Disease: Mutation in a Cholesterol Homeostasis Gene,' Science, 277(5323):232-235 (Jul. 1997).

Madigan et al. "Engineering AAV receptor footprints for gene therapy" Current Opinion in Virology, 18:89-96 (2016).

Mauro et al., "A critical analysis of codon optimization in human therapeutics," Trends in Molecular Medicine, Nov. 2014, vol. 20, No. 11, pp. 604-613.

McLaughlin et al., "Adeno-associated virus general transduction vectors: analysis of proviral structures," J. Virol., (1988) 62:1963-1973.

Miller et al. "Production, purification and preliminary X-ray crystallographic studies of adeno-associated virus serotype 1" Acta Crystallographica Section F: Structural Biology and Crystallization Communications, 62(Pt 12):1271-1274 (2006).

Mingozzi et al. "Immune responses to AAV vectors: overcoming barriers to successful gene therapy" Blood, 122 (1):23-36 (2013).

Mller et al. "Random peptide libraries displayed on adeno-associated virus to select for targeted gene therapy vectors", Nat Biotechnol, Sep. 2003; 21(9):1040-6. Epub Aug. 3, 2003.

Murlidharan et al. "265. Polysialic Acid as a Novel Regulator of AAV Tropism in the Developing Brain" Molecular Therapy 23(Supplement 1):S106 (2015), 1 page.

(56) References Cited

OTHER PUBLICATIONS

Murlidharan et al. "Biology of adeno-associated viral vectors in the central nervous system" Frontiers in Molecular Neuroscience, 7(76):1-9 (2014).

Murlidharan et al. "CNS-restricted Transduction and CRISPR/Cas9-mediated Gene Deletion with an Engineered AAV Vector" Molecular Therapy: Nucleic Acids, 5:e338 (2016).

Murlidharan et al. "Glymphatic fluid transport controls paravascular clearance of MV vectors from the brain" JCI Insight, 1(14):e88034 (2016).

Murlidharan et al. "Unique Glycan Signatures Regulate adeno-Associated Virus Tropism in the Developing Brain" Journal of Virology 89(7):3976-3987 (2015).

Muzyczka, N. "Use of adeno-Associated Virus as a General Transduction Vector for Mammalian Cells," Current Topics in Microbiology and Immunology 158:97-129 (1992).

Nathwani et al. "Long-Term Safety and Efficacy of Factor IX Gene Therapy in Hemophilia B" The New England Journal of Medicine, 371(21):1994-2004 (2014).

Needleman and WUnsch, "A general method applicable to the search for similarities in the amino acid sequence of two proteins." J Mol Biol. (1970); 48(3): 443-453.

Newton & Deutscher, Phage Peptide Display in Handbook of Experimental Pharmacology, pp. 145-163, Springer-Verlag, Berlin (2008).

Nguyen Vu et al., "Cerebellar Purkinje cell activity drives motor learning", Nature Neuroscience 16(12):1734-1736 (2013).

Padron et al. "Structure of adeno-Associated Virus Type 4" Journal of Virology 79(8):5047-5058 (2005).

Palombo et al. "Site-Specific Integration in Mammalian Cells Mediated by a New Hybrid Baculovirus-Adeno-Associated Virus Vector" Journal of Virology72(6):5025-5034 (1998).

Papadakis, ED et al., 'Promoters and Control Elements: Designing Expression Cassettes for Gene Therapy,' Curr. Gene Therapy, vol. 4, No. 1, pp. 89-113, (Mar. 2004).

Partial Supplementary European Search Report issued by the European Patent Office for Application No. 16852471.8, dated Apr. 24, 2019, 17 pages.

Passini, MA et al., 'Distribution of a Lysosomal Enzyme in the Adult Brain by Axonal Transport and by Cells of the Rostral Migratory Stream,' J. Neuroscience, 22(15):6437-6446 (Aug. 2002).

Paul, CA et al., 'Adenovirus Expressing an NPCI-GFP Fusion Gene Corrects Neuronal and Nonneuronal Defects Associated With Niemann Pick Type C Disease,' J. Neurosci. Res., vol. 81, No. 5, pp. 706-719 (Sep. 2005).

Pillay et al. "An essential receptor for adeno-associated virus infection" Nature, 530(7588):108-112 (2016).

Pulicherla et al. "Engineering Liver-detargeted AAV9 Vectors for Cardiac and Musculoskeletal Gene Transfer" Molecular Therapy, 19(6):1070-1078 (2011).

Puttaraju et al. "Spliceosome-mediated RNA trans-splicing as a tool for gene therapy" Nature Biotechnology 17:246-252 (1999).

Rosenberg et al. "A New Era for Cancer Immunotherapy Based on the Genes that Encode Cancer Antigens" Immunity 10:281-287 (1999).

Rosenberg et al. "Comparative Efficacy and Safety of Multiple Routes of Direct CNS Administration of Adeno-Associated Virus Gene Transfer Vector Serotype rh. 10 Expressing the Human Arylsulfatase A cDNA to Nonhuman Primates" Human Gene Therapy Clinical Development, 25(3):164-177 (2014).

Rosenberg "The Immunotherapy of Solid Cancers Based on Cloning the Genes Encoding Tumor-Rejection Antigens" Annual Review of Medicine 47:481-491 (1996).

Saitou, N. et al. (1987). "The neighbor-joining method: A new method for reconstructing phylogenetic trees," Mol. Biol. Evol. 4:406-425.

Salinas et al. "A hitchhiker's guide to the nervous system: the complex journey of viruses and toxins" Nature Reviews Microbiology, 8(9):645-655 (2010). (Abstract only).

Sharp et al. "RNA Interference" Science 287(5462):2431-2433 (2000).

Shen et al. "Engraftment of a Galactose Receptor Footprint onto adeno-associated Viral Capsids Improves Transduction Efficiency" The Journal of Biological Chemistry, 288(40):28814-28823 (2013).

Shen et al., Multiple Roles for Sialylated Glycans in Determining the Cardiopulmonary Tropism of Adeno-Associated Virus 4, Journal of Virology 87(24):13206-13213 (2013).

Shi et al. "Insertional Mutagenesis at Positions 520 and 584 of adeno-Associated Virus Type 2 (AAV2). Capsid Gene and Generation of AAV2 Vectors with Eliminated Heparin-Binding Ability and Introduced Novel Tropism" Human Gene Therapy 17:353-361 (2006).

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.

Smith et al, "Comparison of Biosequences", Advanced in Applied Mathematics, vol. 2, Issue 4, Dec. 1981, pp. 482-489.

Smith, TF et al., 'Identification of Common Molecular Subsequences,' Journal of Molecular Biology, 147:195-197, PMID 7265238. doi: 10.1016/0022-2836(81)90087-5, (1981).

Sonntag et al. "Adeno-Associated Virus Type 2 Capsids with Externalized VP1NP2 Trafficking Domains Are Generated prior to Passage through the Cytoplasm and Are Maintained until Uncoating Occurs in the Nucleus" Journal of Virology, 80(22):11040-11054 (2006).

Summerford et al. "Membrane-Associated Heparan Sulfate Proteoglycan Is a Receptor for adeno-Associated Virus Type 2 Virions" Journal of Virology, 72(2):1438-1445 (1998).

Tellez et al. "Characterization of Naturally-Occurring Humoral Immunity to AAV in Sheep" PLoS One, 8(9):e75142 (2013).

Tinsley et al. "Amelioration of the dystrophic phenotype of mdx mice using a truncated utrophin transgene" Nature 384(6607):349-353 (1996).

Titeux et al., "SIN Retroviral Vectors Expressing col. 7A1 Under Human Promoters for Ex Vivo Gene Therapy of Recessive Dystrophic Epidermolysis Bullosa," Mol. Ther., 2010 18:1509-1518.

Tseng et al. "Adeno-Associated Virus Serotype 1 (AAV1).- and AAV5-Antibody Complex Structures Reveal Evolutionary Commonalities in Parvovirus Antigenic Reactivity" Journal of Virology, 89(3):1794-1808 (2015).

Tseng et al. "Generation and characterization of anti-adeno-associated Virus serotype 8 (AAV8). and anti-AAV9 monoclonal antibodies" Journal of Virological Methods, 236:105-110 (2016).

Tseng et al. "Mapping the AAV capsid host antibody response toward the development of second generation gene delivery vectors" Frontiers in Immunology, 5(9):1-11 (2014).

Urabe et al. "Insect Cells as a Factory to Produce adeno-Associated Virus Type 2 Vectors" Human Gene Therapy 13:1935-1943 (2002).

Various: Abstracts , 20th Annual Meeting of the American-Society-of-Gene-and-Cell-Therapy (ASGCT); Washington, DC, USA; May 10-13, 2017 , Molecular Therapy : The Journal of the American Society of Gene Therapy 25:1-363 (2017).

Veldwijk, MR et al., 'Development and optimization of a real-time quantitative PCR-based method for the titration of AAV-2 vector stocks,' Mal. Ther., 6(2):272-8 (Aug. 2002).

Vincent et al. "Long-term correction of mouse dystrophic degeneration by adenovirus-mediated transfer of a minidystrophin gene" Nature Genetics 5:130-134 (1993).

Walters et al. "Structure of adeno-Associated Virus Serotype 5" Journal of Virology 78(7):3361-3371 (2004).

Wang et al., "Selection of neutralizing antibody-resistant AAV8 variants with structure-guided site-specific saturated mutagenesis," Molecular Therapy, 2011, vol. 19 Suppl. 1, S129.

Wang et al. "Expanding the genetic code" Annual Review of Biophysics and Biomolecular Structure 35:225-249 (2006).

Wassif, CA et al., 'High Incidence of Unrecognized Visceral/Neurological Late onset Niemann-Pick Disease, type C1 Predicted by Analysis of Massively Parallel Sequencing Data Sets,' Genet Med., 18(1):41-48 (Jan. 2016).

Weller et al. "Epidermal growth factor receptor is a co-receptor for adeno-associated virus serotype 6" Nature Medicine, 16(6):662-664 (2010).

(56)        References Cited

OTHER PUBLICATIONS

Williams et al. "Monocyte maturation, HIV susceptibility, and transmigration across the blood brain barrier are critical in HIV neuropathogenesis" Journal of Leukocyte Biology, 91(3):401-415 (2012).

Winkler et al., "Changing the Antigen Binding Specificity by Single Point Mutations of an Anti-p24 (HIV-1) Antibody", The Journal of Immunology, 165: 4505-4514 (2000).

Work, et al., "Vascular bed-targeted in vivo gene delivery using tropism-modified adeno-associated viruses." Mol. Ther.; vol. 13, No. 4, pp. 683-693 (Apr. 2006).

Wu et al. "alpha2,3 and alpha2,6 N-Linked Sialic Acids Facilitate Efficient Binding and Transduction by Adeno-Associated Virus Types 1 and 6" Journal of Virology, 80(18):9093-9103 (2006).

Wu et al. "Single Amino Acid Changes Can Influence Titer, Heparin Binding, and Tissue Tropism in Different adeno-Associated Virus Serotypes" Journal of Virology, 80(22):11393-11397 (2006).

Xiao et al., "Gene transfer by adeno-associated virus vectors into the central nervous system," Exp. Neurobiol., (1997) 144:113-124.

Xiao et al. "Interpretation of Electron Density with Stereographic Roadmap Projections" Journal of Structural Biology, 158(2):182-187 (2007).

Xie et al. "Canine ParvoVirus Capsid Structure, Analyzed at 2.9 A Resolution" Journal of Molecular Biology 264(3):497-420 (1996).

Yang et al. "Global CNS Transduction of Adult Mice by Intravenously Delivered rAAVrh.8 and rAAVrh.10 and Nonhuman Primates by rAAVrh.1O" Molecular Therapy, 22(7):1299-1309 (2014).

Zhang, "Endocytic mechanisms and drug discovery in neurodegenerative diseases," Frontiers in Bioscience 13:6086-6105 (2008).

Zhang et al. "Several rAAV Vectors Efficiently Cross the Blood-brain Barrier and Transduce Neurons and Astrocytes in the Neonatal Mouse Central Nervous System" Molecular Therapy, 19(8):1440-1448 (2011).

Zinn, E. et al., "In Silico Reconstruction of the Viral Evolutionary Lineage Yields a Potent Gene Therapy Vector," Cell Reports, Aug. 2015; 12:1056-1068.

Zolotukhin, et al., "Recombinant adeno-associated virus purification using novel methods improves infectious titer and yield." Gene Therapy (1999); vol. 6, pp. 973-985.

Asokan et al., "The AVV Vector Toolkit: Poised at the Clinical Crossroads," Molecular Therapy 20(4):699-708 (2012).

Bennett et al. "AAV6 K531 serves a dual function in selective receptor and antibody ADK6 recognition" Virology, 18:369-376 (2018).

Clapcote SJ, et al., "Mutation 1810N in the alpha3 isoform of Na+,K+-ATPase causes impairments in the sodium pump and hyperexcitability in the CNS," Proc Natl Acad Sci USA. 106(33):14085-14090 (2009).

Conway et al. "High-titer recombinant adeno-associated virus production utilizing a recombinant herpes simplex virus type 1 vector expressing AAV-2 Rep and Cap" Gene Therapy 6:986-993 (1999).

Piguet Françoise et al., "Rapid and Complete Reversal of Sensory Ataxia by Gene Therapy in a Novel Model of Friedreich Ataxia", Molecular Therapy, Nature Publishing Group, GB 26(8), pp. 1-13 (2018).

Ghusayni R et al., "Magnetic resonance imaging volumetric analysis in patients with Alternating hemiplegia of childhood: A pilot study," Eur J Paediatr Neurol. 26:15-19 (2020).

Heinzen EL, et al., "De nova mutations in ATP1A3 cause alternating hemiplegia of childhood," Nat Genet. 44 (9):1030-1034 (2012).

Helseth AR, et al., "Novel E815K knock-in mouse model of alternating hemiplegia of childhood," Neurobiol Dis. 119:100-112 (2018).

Holm R et al., "B. Neurological disease mutations of a3 Na+,K+-ATPase: Structural and functional perspectives and rescue of compromised function," Biochim Biophys Acta. 1857(11):1807-1828 (2016).

Hunanyan AS, et al., Knock-in mouse model of alternating hemiplegia of childhood: behavioral and electrophysiologic characterization. Epilepsia. 56(1):82-93 (2015).

Hunanyan AS, et al., "Mechanisms of increased hippocampal excitability in the Mashl+/− mouse model of Na+ /K+-ATPase dysfunction," Epilepsia 59(7):1455-1468 (2018).

Ikeda K. et al., "Knockout of sodium pump a3 subunit gene(Atp1a3-/-) results in perinatal seizure and defective respiratory rhythm generation," Brain Res. 1666:27-37 (2017).

International Search Report and Written Opinion for International Application No. PCT/US2021/046699 dated Jan. 12, 2022, 17 pages.

International Search Report and Written Opinion issued by the International Searching Authority for Application No. PCT/US2022/012542, dated Jun. 3, 2022, 10 pages.

Isaksen TJ, et al., "Hypothermia-induced dystonia and abnormal cerebellar activity in a mouse model with a single disease-mutation in the sodium-potassium pump," PLoS Genet. 13(5):e1006763, pp. 1-23 (2017).

Kells, A.P., et al., "AAV-Mediated Gene Delivery of BDNF or GDNF is Neuroprotective in a Model of Huntington Disease," Molecular Therapy, May 2004, vol. 9(5), pp. 682-688.

Kirshenbaum GS, et al., "Alternating hemiplegia of childhood-related neural and behavioural phenotypes in Na+,K+-ATPase a3 missense mutant mice," PLoS One. 8(3):e60141, pp. 1-15 (2013).

Kuck et al. "Development of AAV serotype-specific ELISAs using novel monoclonal antibodies" Journal of Virological Methods, 140(1-2):17-24 (2007) (Abstract only).

Lux et al. "Green Fluorescent Protein-Tagged Adeno-Associated Virus Particles Allow the Study of Cytosolic and Nuclear Trafficking" Journal of Virology, 79{18):11776-11787 (2005).

Margolskee, R. F. "Epstein-Barr Virus Based Expression Vectors" Current Topics in Microbiology and Immunology 158:67-95 (1992).

Masoud M, et al., "Diagnosis and Treatment of Alternating Hemiplegia of Childhood," Curr Treat Options Neurol. 19(2):8 (2017).

Mccraw et al. "structurE of adeno-associated virus-2 In Complex with Neutralizing Monoclonal antibodY A20" Virology, 431(1-2):40-49 (2012).

Mikati MA, et al., "Alternating hemiplegia of childhood: clinical manifestations and long-term outcome," Pediatr Neurol. 23(2):134-141 (2000).

Pearson and Lipman, "Improved tools for biological sequence comparison," PNAS USA, Apr. 1988, 85:2444-2448.

Powell et al. Characterization of a Novel Adena-Associated Viral Vector with Preferential Oligodendrocyte Tropism. Gene Therapy, 2016. 23:807-814.

Severino M, et al., "White matter and cerebellar involvement in alternating hemiplegia of childhood," J Neurol. 267 (5):1300-1311 (2020).

Veron et al. "Humeral and Cellular Capsid-Specific Immune Responses to Adena-Associated Virus Type 1 in andomized Healthy Donors" The Journal of Immunology, 188:6418-6424 (2012).

Wang; Q. et al., "Identification of an adeno-associated Virus binding epitope for AVB sepharose affinity resin," Molecular Therapy—Methods & Clinical Development vol. 2, pp. 1-6 (2015).

Wobus et al. "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection," J. of Virology, 74(19):9281-9293 (2000).

Ye Q, et al., "The AAA+ ATPase TRIP13 remodels HORMA domains through N-terminal engagement and unfolding," EMBO J. 36(16):2419-2434 (2017).

Zhong et al. "Next generation of adeno-associated virus 2 vectors: Point mutations in tyrosines lead to high-efficienc ransduction at lower doses" Proceedings of the National Academy of Sciences USA, 105(22):7827-7832 (2008).

Zhong et al. "Tyrosine-phosphorylation of AAV2 vectors and its consequences on viral intracellular trafficking and transgene expression" Virology, 381(2):194-202 (2008).

Zolotukhin et al. "Production and purification of serotype 1, 2, and 5 recombinant adeno-associated viral vectors" Methods, 28(2):158-167 (2002) {Abstract only).

Adachi et al., "Drawing a high-resolution functional map of adeno-associated virus capsid by massively parallel sequencing," Nature Communications 5(1): 14 pages (2013).

(56)        References Cited

OTHER PUBLICATIONS

Altschul et al., "Gapped BLAST and PSI-BLAST: a new generation of protein database search programs" Nucleic Acids Research 25(17):3389-3402 (1997).
Arrunda et al., "Regional intravascular delivery of AAV-2-F.IX to skeletal muscle achieves long-term correction of hemophilia B in a large animal model," Blood 105:3458-3464 (2005).
Bantel-Schaal et al. "Human adeno-Associated Virus Type 5 Is Only Distantly Related to Other Known Primate Helper-Dependent Parvovirus" Journal of Virology 73(2):939-947 (1999).
Chao et al. "Several Log Increase in Therapeutic Transgene Delivery by Distinct Adeno-Associated Viral Serotype Vectors" Molecular Therapy 2(6):619-623 (2000).
Chiorini et al. "Cloning and Characterization of adeno-Associated VirUS Type 5" Journal of Virology 73(2):1309-1319 (1999).
Chiorini et al. "Cloning of adeno-Associated Virus Type 4 (AAV4). and Generation of Recombinant AAV4 Particles" Journal of Virology 71(9):6823-6833 (1997).
Chipman et al. "Cryo-electron microscopy studies of empty capsids of human parvovirus 819 complexed with its cellular receptor" Proceedings of the National Academy of Sciences 93:7502-7506 (1996).
Chirmule et al., "Humoral immunity to Adeno-Associated Virus type 2 vectors following administration to murine and nonhuman primate Muscle," Journal of Virology, The Ameriucan Society for Microbiology 74(5):2420-2425 (2000).
Cleves, "Protein transport: The nonclassical ins and outs," Current Biology 7:R318-R320 (1997).
Dimattia et al. "Structural Insight into the Unique Properties of Adeno-Associated Virus Serotype 9," Journal of Virology, 86(12):6947-6958 (2012).
Fang et al., "Stable antibody expression at therapeutic levels using the 2A peptide," Nature Biotechnology 23:584-590 (2005).
Gao et al. "Novel adeno-associated viruses from Rhesus Monkeys as Vectors for human gene therapy," Proceedings of the National Academy of Sciences 99(18): 11854-11859 (2002).
Genbank Accession No. DQ813647, Adeno-Associated Virus 12 Rep 78 and VP1 genes, complete cds., dated Feb. 20, 2008, 3 pages.
Genbank Accession No. AY243001, Non-Human Primate Adeno-associated Virus Isolate AAVrh.34 caapsidprotein (VP1) gene, complete cds., dated May 14, 2003, 2 pages.
Genbank Accession No. AY243002, Non-Human Primate Adeno-associated Virus Isolate AAVrh.33 caapsidprotein (VP1) gene, complete cds. dated May 14, 2003, 2 pages.
Genbank Accession No. AY243003, Non-Human Primate Adeno-associated Virus Isolate AAVrh.32 caapsidprotein (VP1) gene, complete cds, dated May 14, 2003, 2 pages.
Genbank Accession No. AAR26465, Bovine Adeno-Associated Virus, dated May 25, 2004, 2 pages.
Genbank Accession No. AAT46339, capsid protein [Adeno-associated virus 11], dated Nov. 30, 2004, 2 pages.
Genbank Accession No. ABI16639, VP1 [Adeno-associated virus 12, dated Feb. 20, 2008, 2 pages.
Genbank Accession No. AF063497, Adeno-associate virus 1, complete genome, dated Apr. 27, 1999, 3 pages.
Genbank Accession No. AY186198, Avian adeno-associated virus Atcc VR-865, complete genome, dated Jun. 5, 2003, 3 pages.
Genbank Accession No. AY242997, Non-Human primate Adeno-associated virus isolate AAVrh.8 capsid protein (VP1) gene, complete cds, dated May 14, 2003, 2 pages.
Genbank Accession No. AY242998, Non-Human primate Adeno-associated virus isolate AAVrh.37 capsid protein (VP1) gene, complete cds, dated May 14, 2003, 2 pages.
Genbank Accession No. AY242999, Non-Human primate Adeno-associated virus isolate AAVrh.36 capsid protein (VP1) gene, complete cds, dated May 14, 2003, 2 pages.
Genbank Accession No. AY243000, Non-Human primate Adeno-associated virus isolate AAVrh.35 capsid protein (VP1) gene, complete cds, dated May 14, 2003, 2 pages.

Genbank Accession No. AY243007, Non-Human Primate Adeno-associated Virus Isolate AAVrh.2 capsid protein (VP1) gene, complete cds, dated May 14, 2003, 2 pages.
Genbank Accession No. AY243013, Non-Human primate Adeno-associated virus isolate AAVrh. 13 capsid protein (VP1) gene, complete cds, dated May 14, 2003, 2 pages.
Genbank Accession No. AY243015, Non-Human primate Adeno-associated virus isolate AAVrh. 10 capsid protein (VP1) gene, complete cds dated May 14, 2003, 2 pages.
Genbank Accession No. AY243016, Non-Human primate Adeno-associated virus isolate AAVcy.6 capsid protein (VP1) gene, complete cds dated May 14, 2003, 2 pages.
Genbank Accession No. AY243017, Non-Human primate Adeno-associated virus isolate AAVcy.5 capsid protein (VP1) gene, complete cds, dated May 14, 2003, 2 pages.
Genbank Accession No. AY243018, Non-Human primate Adeno-associated virus isolate AAVcy.4 capsid protein (VP1) gene, complete cds, dated May 14, 2003, 2 pages.
Genbank Accession No. AY243019, Non-Human primate Adeno-associated virus isolate AAVcy.3 capsid protein (VP1) gene, complete cds, dated May 14, 2003, 2 pages.
Genbank Accession No. AY243020, Non-Human primate Adeno-associated virus isolate AAVcy.2 capsid protein (VP1) gene, complete cds, dated May 14, 2003, 2 pages.
Genbank Accession No. AY243021, Non-Human primate Adeno-associated virus isolate AAVch.5 capsid protein (VP1) gene, complete cds, dated May 14, 2003, 2 pages.
Genbank Accession No. AY243022, Non-Human primate Adeno-associated virus isolate AAVbb.2 capsid protein (VP1) gene, complete cds, dated May 14, 2003, 2 pages.
Genbank Accession No. AY243023, Non-Human primate Adeno-associated virus isolate AAVbb.1 capsid protein (VP1) gene, complete cds, dated May 14, 2003, 2 pages.
Genbank Accession No. AY388617, Bovine adeno-associated virus, complete genome, dated May 25, 2004, 3 pages.
Genbank Accession No. AY530553, Adeno-associated virus isolate pi.1 capsid protein VP1 (cap) gene, complete cds, dated Jun. 24, 2004, 2 pages.
Genbank Accession No. AY530554, Adeno-associated virus isolate pi.2 capsid protein VP1 (cap) gene, complete cds, dated Jun. 24, 2004, 2 pages.
Genbank Accession No. AY530555, Adeno-associated virus isolate pi.3 capsid protein VP1 (cap) gene, complete cds, dated Jun. 24, 2004, 2 pages.
Genbank Accession No. AY530556, Adeno-associated virus isolate rh.1 capsid protein VP1 (cap) gene, complete cds, dated Jun. 24, 2004, 2 pages.
Genbank Accession No. AY530557, Adeno-associated virus isolate rh.25 capsid protein VP1 (cap) gene, complete cds, dated Jun. 24, 2004, 2 pages.
Genbank Accession No. AY530558, Adeno-associated virus isolate rh.38 capsid protein VP1 (cap) gene, complete cds, dated Jun. 24, 2004, 2 pages.
Genbank Accession No. AY530559, Adeno-associated virus isolate rh.40 capsid protein VP1 (cap) gene, complete cds, dated Jun. 24, 2004, 2 pages.
Genbank Accession No. AY530560, Adeno-associated virus isolate rh.43 capsid protein VP1 (cap) gene, complete cds, dated Jun. 24, 2004, 2 pages.
Genbank Accession No. AY530561, Adeno-associated virus isolate rh.48 capsid protein VP1 (cap) gene, complete cds, dated Jun. 24, 2004, 2 pages.
Genbank Accession No. AY530562, Adeno-associated virus isolate rh.49 capsid protein VP1 (cap) gene, complete cds, dated Jun. 24, 2004, 2 pages.
Genbank Accession No. AY530563, Adeno-associated virus isolate rh.50 capsid protein VP1 (cap) gene, complete cds, dated Jun. 24, 2004, 2 pages.
Genbank Accession No. AY530564, Adeno-associated virus isolate rh.51 capsid protein VP1 (cap) gene, complete cds, dated Jun. 24, 2004, 2 pages.

(56)  References Cited

OTHER PUBLICATIONS

Genbank Accession No. AY530565, Adeno-associated virus isolate rh.52 capsid protein VP1 (cap) gene, complete cds, dated Jun. 24, 2004, 2 pages.

Genbank Accession No. AY530566, Adeno-associated virus isolate rh.53 capsid protein VP1 (cap) gene, complete cds, dated Jun. 24, 2004, 2 pages.

Genbank Accession No. AY530567, Adeno-associated virus isolate rh.54 capsid protein VP1 (cap) gene, complete cds, dated Jun. 24, 2004, 2 pages.

Genbank Accession No. AY530568, Adeno-associated virus isolate rh.55 capsid protein VP1 (cap) gene, complete cds, dated Jun. 24, 2004, 2 pages.

Genbank Accession No. AY530569, Adeno-associated virus isolate rh.57 capsid protein VP1 (cap) gene, complete cds, dated Jun. 24, 2004, 2 pages.

Genbank Accession No. AY530570, Adeno-associated virus isolate rh.58 capsid protein VP1 (cap) gene, complete cds, dated Jun. 24, 2004, 2 pages.

Genbank Accession No. AY530572, Adeno-associated virus isolate rh.61 capsid protein VP1 (cap) gene, complete cds, dated Jun. 24, 2004, 2 pages.

Genbank Accession No. AY530573, Adeno-associated virus isolate rh.62 capsid protein VP1 (cap) gene, complete cds, dated Jun. 24, 2004, 2 pages.

Genbank Accession No. AY530574, Adeno-associated virus isolate rh.64 capsid protein VP1 (cap) gene, complete cds, dated Jun. 24, 2004, 2 pages.

Genbank Accession No. AY530575, Adeno-associated virus isolate hu.1 capsid protein VP1 (cap) gene, complete cds, dated Jun. 24, 2004, 2 pages.

Genbank Accession No. AY530576, Adeno-associated virus isolate hu.10 capsid protein VP1 (cap) gene, complete cds, dated Jun. 24, 2004, 2 pages.

Genbank Accession No. AY530577, Adeno-associated virus isolate hu.11 capsid protein VP1 (cap) gene, complete cds, dated Jun. 24, 2004, 2 pages.

Genbank Accession No. AY530578, Adeno-associated virus isolate hu.13 capsid protein VP1 (cap) gene, complete cds, dated Jun. 24, 2004, 2 pages.

Genbank Accession No. AY530579, Adeno-associated virus isolate hu. 14 capsid protein VP1 (cap) gene, complete cds, dated Jun. 24, 2004, 2 pages.

Genbank Accession No. AY530580, Adeno-associated virus isolate hu.15 capsid protein VP1 (cap) gene, complete cds, dated Jun. 24, 2004, 2 pages.

Genbank Accession No. AY530581, Adeno-associated virus isolate hu.16 capsid protein VP1 (cap) gene, complete cds, dated Jun. 24, 2004, 2 pages.

Genbank Accession No. AY530582, Adeno-associated virus isolate hu.17 capsid protein VP1 (cap) gene, complete cds, dated Jun. 24, 2004, 2 pages.

Genbank Accession No. AY530583, Adeno-associated virus isolate hu.18 capsid protein VP1 (cap) gene, complete cds, dated Jun. 24, 2004, 2 pages.

Genbank Accession No. AY530584, Adeno-associated virus isolate hu.19 capsid protein VP1 (cap) gene, complete cds, dated Jun. 24, 2004, 2 pages.

Genbank Accession No. AY530585, Adeno-associated virus isolate hu.2 capsid protein VP1 (cap) gene, complete cds, dated Jun. 24, 2004, 2 pages.

Genbank Accession No. AY530586, Adeno-associated virus isolate hu.20 capsid protein VP1 (cap) gene, complete cds, dated Jun. 24, 2004, 2 pages.

Genbank Accession No. AY530587, Adeno-associated virus isolate hu.21 capsid protein VP1 (cap) gene, complete cds, dated Jun. 24, 2004, 2 pages.

Genbank Accession No. AY530588, Adeno-associated virus isolate hu.22 capsid protein VP1 (cap) gene, complete cds, dated Jun. 24, 2004, 2 pages.

Genbank Accession No. AY530589, Adeno-associated virus isolate hu.23 capsid protein VP1 (cap) gene, complete cds, dated Jun. 24, 2004, 2 pages.

Genbank Accession No. AY530590, Adeno-associated virus isolate hu.24 capsid protein VP1 (cap) gene, complete cds, dated Jun. 24, 2004, 2 pages.

Genbank Accession No. AY530591, Adeno-associated virus isolate hu.25 capsid protein VP1 (cap) gene, complete cds, dated Jun. 24, 2004, 2 pages.

Genbank Accession No. AY530592, Adeno-associated virus isolate hu.27 capsid protein VP1 (cap) gene, complete cds, dated Jun. 24, 2004, 2 pages.

Genbank Accession No. AY530593, Adeno-associated virus isolate hu.28 capsid protein VP1 (cap) gene, complete cds, dated Jun. 24, 2004, 2 pages.

Genbank Accession No. AY530594, Adeno-associated virus isolate hu.29 capsid protein VP1 (cap) gene, complete cds, dated Jun. 24, 2004, 2 pages.

Genbank Accession No. AY530595, Adeno-associated virus isolate hu.3 capsid protein VP1 (cap) gene, complete cds, dated Jun. 24, 2004, 2 pages.

Genbank Accession No. AY530596, Adeno-associated virus isolate hu.31 capsid protein VP1 (cap) gene, complete cds, dated Jun. 24, 2004, 2 pages.

Genbank Accession No. AY530597, Adeno-associated virus isolate hu.32 capsid protein VP1 (cap) gene, complete cds, dated Jun. 24, 2004, 2 pages.

Genbank Accession No. AY530598, Adeno-associated virus isolate hu.34 capsid protein VP1 (cap) gene, complete cds, dated Jun. 24, 2004, 2 pages.

Genbank Accession No. AY530599, Adeno-associated virus isolate hu.35 capsid protein VP1 (cap) gene, complete cds, dated Jun. 24, 2004, 2 pages.

Genbank Accession No. AY530600, Adeno-associated virus isolate hu.37 capsid protein VP1 (cap) gene, complete cds, dated Jun. 24, 2004, 2 pages.

Genbank Accession No. AY530601, Adeno-associated virus isolate hu.39 capsid protein VP1 (cap) gene, complete cds, dated Jun. 24, 2004, 2 pages.

Genbank Accession No. AY530602,Adeno-associated virus isolate hu.4 capsid protein VP1 (cap) gene, complete cds, dated Jun. 24, 2004, 2 pages.

Genbank Accession No. AY530603, Adeno-associated virus isolate hu.40 capsid protein VP1 (cap) gene, complete cds, dated Jun. 24, 2004, 2 pages.

Genbank Accession No. AY530604, Adeno-associated virus isolate hu.41 capsid protein VP1 (cap) gene, complete cds, dated Jun. 24, 2004, 2 pages.

Genbank Accession No. AY530605, Adeno-associated virus isolate hu.42 capsid protein VP1 (cap) gene, complete cds, dated Jun. 24, 2004, 2 pages.

Genbank Accession No. AY530606, Adeno-associated virus isolate hu.43 capsid protein VP1 (cap) gene, complete cds, dated Jun. 24, 2004, 2 pages.

Genbank Accession No. AY530607, Adeno-associated virus isolate hu.44 capsid protein VP1 (cap) gene, complete cds, dated Jun. 24, 2004, 2 pages.

Genbank Accession No. AY530608, Adeno-associated virus isolate hu.45 capsid protein VP1 (cap) gene, complete cds, dated Jun. 24, 2004, 2 pages.

Genbank Accession No. AY530609, Adeno-associated virus isolate hu.46 capsid protein VP1 (cap) gene, complete cds, dated Jun. 24, 2004, 2 pages.

Genbank Accession No. AY530610, Adeno-associated virus isolate hu.47 capsid protein VP1 (cap) gene, complete cds, dated Jun. 24, 2004, 2 pages.

Genbank Accession No. AY530611, Adeno-associated virus isolate hu.48 capsid protein VP1 (cap) gene, complete cds, dated Jun. 24, 2004, 4 pages.

Genbank Accession No. AY530612, Adeno-associated virus isolate hu.49 capsid protein VP1 (cap) gene, complete cds, dated Jun. 24, 2004, 2 pages.

(56)                References Cited

OTHER PUBLICATIONS

Genbank Accession No. AY530613, Adeno-associated virus isolate hu.51 capsid protein VP1 (cap) gene, complete cds, dated Jun. 24, 2004, 2 pages.
Genbank Accession No. AY530614, Adeno-associated virus isolate hu.52 capsid protein VP1 (cap) gene, complete cds, dated Jun. 24, 2004, 2 pages.
Genbank Accession No. AY530615, Adeno-associated virus isolate hu.53 capsid protein VP1 (cap) gene, complete cds, dated Jun. 24, 2004, 2 pages.
Genbank Accession No. AY530616, Adeno-associated virus isolate hu.54 capsid protein VP1 (cap) gene, complete cds, dated Jun. 24, 2004, 2 pages.
Genbank Accession No. AY530617, Adeno-associated virus isolate hu.55 capsid protein VP1 (cap) gene, complete cds, dated Jun. 24, 2004, 2 pages.
Genbank Accession No. AY530618, Adeno-associated virus isolate hu.56 capsid protein VP1 (cap) gene, complete cds, dated Jun. 24, 2004, 2 pages.
Genbank Accession No. AY530619, Adeno-associated virus isolate hu.57 capsid protein VP1 (cap) gene, complete cds, dated Jun. 24, 2004, 2 pages.
Genbank Accession No. AY530620, Adeno-associated virus isolate hu.58 capsid protein VP1 (cap) gene, complete cds, dated Jun. 24, 2004, 2 pages.
Genbank Accession No. AY530621, Adeno-associated virus isolate hu.6 capsid protein VP1 (cap) gene, complete cds, dated Jun. 24, 2004, 2 pages.
Genbank Accession No. AY530622, Adeno-associated virus isolate hu.60 capsid protein VP1 (cap) gene, complete cds, dated Jun. 24, 2004, 2 pages.
Genbank Accession No. AY530623, Adeno-associated virus isolate hu.61 capsid protein VP1 (cap) gene, complete cds, dated Jun. 24, 2004, 2 pages.
Genbank Accession No. AY530624, Adeno-associated virus isolate hu.63 capsid protein VP1 (cap) gene, complete cds, dated Jun. 24, 2004, 2 pages.
Genbank Accession No. AY530625, Adeno-associated virus isolate hu.64 capsid protein VP1 (cap) gene, complete cds, dated Jun. 24, 2004, 2 pages.
Genbank Accession No. AY530626, Adeno-associated virus isolate hu.66 capsid protein VP1 (cap) gene, complete cds, dated Jun. 24, 2004, 2 pages.
Genbank Accession No. AY530627, Adeno-associated virus isolate hu.67 capsid protein VP1 (cap) gene, complete cds, dated Jun. 24, 2004, 2 pages.
Genbank Accession No. AY530628, Adeno-associated virus isolate hu.7 capsid protein VP1 (cap) gene, complete cds, dated Jun. 24, 2004, 2 pages.
Genbank Accession No. AY530629, Adeno-associated virus isolate hu.9 capsid protein VP1 (cap) gene, complete cds, dated Jun. 24, 2004, 2 pages.
Genbank Accession No. AY629583, Avian adeno-associated virus strain DA-1, complete genome, dated Sep. 10, 2004, 3 pages.
Genbank Accession No. AY631966, Adeno-associated virus 11 nonstructural protein and capsid protein genes, complete cds, dated Nov. 30, 2004, 3 pages.
Genbank Accession No. AY695370, Adeno-associated virus isolate hu.T17 capsid protein VP1 (cap) gene, complete cds, dated Nov. 15, 2005, 3 pages.
Genbank Accession No. AY695371, Adeno-associated virus isolate hu.T32 Rep 78 protein and capsid protein VP1 (cap) genes, complete cds, dated Nov. 15, 2005, 3 pages.
Genbank Accession No. AY695372, Adeno-associated virus isolate hu.T40 Rep 78 protein and capsid protein VP1 (cap) genes, complete cds, dated Nov. 15, 2005, 3 pages.
Genbank Accession No. AY695373, Adeno-associated virus isolate hu.T70 Rep 78 protein and capsid protein VP1 (cap) genes, complete cds, dated Nov. 15, 2005, 3 pages.

Genbank Accession No. AY695374, Adeno-associated virus isolate hu.T32 Rep 71 protein and capsid protein VP1 (cap) genes, complete cds, dated Nov. 15, 2005, 3 pages.
Genbank Accession No. AY695375, Adeno-associated virus isolate hu.T88 Rep 78 protein and capsid protein VP1 (cap) genes, complete cds, dated Nov. 15, 2005, 3 pages.
Genbank Accession No. AY695376, Adeno-associated virus isolate hu.S17 Rep 78 protein and capsid protein VP1 (cap) genes, complete cds, dated Nov. 15, 2005, 3 pages.
Genbank Accession No. AY695377, Adeno-associated virus isolate hu.LG15 capsid protein VP1 (cap) gene, complete cds, dated Nov. 15, 2005, 3 pages.
Genbank Accession No. AY695378, Adeno-associated virus isolate hu.T41 capsid protein VP1 (cap) gene, complete cds, dated Nov. 15, 2005, 2 pages.
Genbank Accession No. MI332400.1, Sequence 20 from U.S. Pat. No. 9,839,696, dated Feb. 12, 2018, 2 pages.
Genbank Accession No. MI332401.1, Sequence 21 from U.S. Pat. No. 9,839,696, dated Feb. 12, 2018, 2 pages.
Genbank Accession No. MI332402.1, Sequence 22 from U.S. Pat. No. 9,839,696, dated Feb. 12, 2018, 2 pages.
Genbank Accession No. MI332403.1, Sequence 23 from U.S. Pat. No. 9,839,696, dated Feb. 12, 2018, 2 pages.
Genbank Accession No. MI332404.1, Sequence 24 from U.S. Pat. No. 9,839,696, dated Feb. 12, 2018, 2 pages.
Genbank Accession No. MI332405.1, Sequence 25 from U.S. Pat. No. 9,839,696, dated Feb. 12, 2018, 2 pages.
Genbank Accession No. MI332406.1, Sequence 26 from U.S. Pat. No. 9,839,696, dated Feb. 12, 2018, 2 pages.
Genbank Accession No. MI332407.1, Sequence 27 from U.S. Pat. No. 9,839,696, dated Feb. 12, 2018, 2 pages.
Genbank Accession No. MI332408.1, Sequence 28 from U.S. Pat. No. 9,839,696, dated Feb. 12, 2018, 2 pages.
Genbank Accession No. MI332409.1, Sequence 29 from U.S. Pat. No. 9,839,696, dated Feb. 12, 2018, 2 pages.
Genbank Accession No. MI332410.1, Sequence 30 from U.S. Pat. No. 9,839,696, dated Feb. 12, 2018, 2 pages.
Genbank Accession No. MI332411.1, Sequence 31 from U.S. Pat. No. 9,839,696, dated Feb. 12, 2018, 2 pages.
Genbank Accession No. MI332412.1, Sequence 32 from U.S. Pat. No. 9,839,696, dated Feb. 12, 2018, 2 pages.
Genbank Accession No. MI332413.1, Sequence 33 from U.S. Pat. No. 9,839,696, dated Feb. 12, 2018, 2 pages.
Genbank Accession No. MI332414.1, Sequence 34 from U.S. Pat. No. 9,839,696, dated Feb. 12, 2018, 2 pages.
Genbank Accession No. MI332415.1, Sequence 35 from U.S. Pat. No. 9,839,696, dated Feb. 12, 2018, 2 pages.
Genbank Accession No. NC_001729, Adeno-associated virus—3, complete genome, dated Aug. 13, 2018, 3 pages.
Genbank Accession No. NC_001829, Adeno-associated virus—4, complete genome, dated Aug. 13, 2018, 3 pages.
Genbank Accession No. NC_001862, Adeno-associated virus—6, complete genome, dated Jan. 12, 2004, 4 pages.
Genbank Accession No. NC_001863, Adeno-associated virus 3B, complete genome, dated Jan. 12, 2004, 4 pages.
Genbank Accession No. NC_004828, Avian adeno-associated virus ATCC VR-865, complete genome, dated Aug. 13, 2018, 3 pages.
Genbank Accession No. NC_005889, Bovine adeno-associated virus, complete genome, dated Aug. 13, 2018, 3 pages.
Genbank Accession No. NC_006148.1, Snake parvovirus 1, complete genome, dated Aug. 13, 2018, 3 pages.
Genbank Accession No. NC_006263, Avian adeno-associated virus strain DA-1, complete genome, dated Aug. 13, 2018, 3 pages.
Genbank Accession No. Y18065, adeno-associated virus type 5 partial genome (cap and rep genes complete), dated Jan. 15, 1999, 3 pages.
Genbank Accession No. NC_001401, Adeno-associated virus—2, complete genome, dated Aug. 13, 2018, 6 pages.
Genbank Accession No. NC_002077, Adeno-associated virus—1, dated Aug. 13, 2018, 3 pages.
GenBank Accession No. AF028704 "adeno-associated Virus 6, complete genome" NCBI (2 pages). (Jan. 12, 1998).

(56) References Cited

OTHER PUBLICATIONS

GenBank Accession No. AF028705 "adeno-associated Virus 3B, complete genome" NCBI (2 pages). (Jan. 12, 1998).
GenBank Accession No. AF043303 "adeno-Associated Virus 2, complete genome" NCBJ (4 pages). (May 20, 2010).
GenBank Accession No. AF063497 "adeno-associated Virus 1, complete genome" NCBI (2 pages). (Apr. 27, 1999).
GenBank Accession No. AF288061 "Hamster parvoVirus 5' terminal hairpin gene sequence" NCBI (1 page). (Apr. 13, 2001), replaced by AH009962.
GenBank Accession No. AF513851 "adeno-associated Virus 7 nonstructural protein and capsid protein genes, complete eds." NCBI (2 pages). (Sep. 5, 2002).
GenBank Accession No. AF513852 "adeno-associated Virus 8 nonstructural protein and capsid protein genes, complete eds" NCBI (2 pages). (Sep. 5, 2002).
GenBank Accession No. AH009962 "Hamster parvovir" NCBI (1 page). (Aug. 25, 2016), replaced AF288061.
GenBank Accession No. AY028223 "B19 Virus isolate patient_A. 1.1 genomic sequence" NCB/ (1 page). (Apr. 16, 2001).
GenBank Accession No. AY028226 "819 Virus isolate patient_A. 2.1 genomic sequence" NCB/ (1 page). (Apr. 16, 2001).
GenBank Accession No. AY530579 "adeno-associated Virus 9 isolate hu. 14 capsid protein VP1 (cap). gene, complete eds" NCBI (2 pages). (Jun. 24, 2004).
GenBank Accession No. J00306 "Human somatostatin I gene and flanks" NCBJ (2 pages). (Jan. 13, 1995).
GenBank Accession No. J01901 "adeno-associated Virus 2, complete genome" NCBJ (3 pages). (Apr. 27, 1993).
GenBank Accession No. J02275 "Minute Virus of mice, complete genome" NCBJ (4 pages). (May 22, 1995).
GenBank Accession No. NC_000883 "Human parvoVirus 819, complete genome" NCBI (4 pages). (Feb. 10, 2015).
GenBank Accession No. NC_001358 "ParvoVirus H1, complete genome" NCBI (3 pages). (Feb. 10, 2015).
GenBank Accession No. NC_001401 "adeno-associated Virus—2, complete genome" NCBI (5 pages). (Dec. 2, 2014).
GenBank Accession No. NC_001510 "Minute Virus of mice, complete genome" NCBI (5 pages). (Mar. 28, 2016).
GenBank Accession No. NC_001701 "Goose parvovir, complete genome" NCBI (4 pages). (Jan. 28, 2010).
GenBank Accession No. NC_001729 "adeno-associated vir-3, complete genome" NCBI (3 pages). (Jun. 28, 2010).
GenBank Accession No. NC_001829 "adeno-associated Virus—4, complete genome" NCBI (3 pages). (Jan. 28, 2010).
GenBank Accession No. NC_001862 "adeno-associated Virus 6, complete genome" NCBJ (3 pages). (Jan. 12, 2004).
GenBank Accession No. NC_001863 "adeno-associated Virus 38, complete genome" NCB/ (3 pages). (Jan. 12, 2014).
GenBank Accession No. NC_002077 "adeno-associated Virus—1, complete genome" NCBI (3 pages). (Mar. 11, 2010).
GenBank Accession No. NC_006152 "adeno-associated Virus 5, complete genome" NCBI (3 pages). (Dec. 8, 2008).
GenBank Accession No. P01166 "Somatostatin precursor [Contains:Somatostatin 28; Somatostatin—14]" NCBI (2 pages). (Sep. 15, 2003).
GenBank Accession No. U89790 "Adeno-associated Virus 4, complete genome" NCBI (2 pages). (Aug. 21, 1997).
GenBank Accession No. X01457 "ParvoVirus h-1, complete genome" NCBI (3 pages). (Apr. 18, 2005).
GenBank Accession No. NC_006261 "adeno-associated Virus—8, complete genome" NCBI (3 pages). (Mar. 11, 2010).
GenBankAccession No. NC_001540 "Bovine parvovir, complete genome" NCBI (4 pages). (Nov. 30, 2009).
Govindasamy et al., "Structurally mapping the diverse phenotype of adeno-associated virus serotype 4," J. Virol 80:11556-11570 (2006).
Govindasamy et al., "Structural Insights into Adeno-Associated Virus Serotype 5," J. Virology 87:11187-11199 (2013).

Gregorevic et al. "Systemic Microdystrophin Gene Delivery Improves Skeletal Muscle Structure and Function in Old Dystrophic mdx Mice," Molecular Therapy 16(4):657-664 (2008).
Grifman et al. "Incorporation of Tumor-Targeting Peptides into Recombinant Adeno- Associated Virus Capsids" Molecular Therapy 3(6):964-975 (2001).
Gurda et al. "Capsid Antibodies to Different adeno-Associated Virus Serotypes Bind Common Regions" Journal of Virology, 87(16):9111-9124 (2013).
Hauck et al. "Characterization of Tissue Tropism Determinants of Adeno-Associated Virus Type 1" Journal of Virology 77(4):2768-2774 (2003).
Huang et al. "ParvoVirus qlycan interactions" Current Opinion in Virology 7:108-118 (2014).
Kailasan et al., "Structure of an enteric pathogen, bovine parvovirus," Virology 89:2603-2614 (2015).
Karlin et al. "Applications and statistics for multiple high-scoring segments in molecular sequences" Proceedings of National Academy of Sciences 90:5873-5877 (1993).
Kawakami et al. "Cloning of the gene coding for a shared human melanoma antigen recognized by autologous T cells infiltrating into tumor," Proceedings of the National Academy of Sciences 91:3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" The Journal of Experimental Medicine 180:347-352 (1994).
Koivunen et al., "Identification of Receptor Ligands with Phase Display Peptide Libraries," J. Nucl. Med. 40:883-888 (1999).
Lerch et al., "The structure of adeno-associated virus serotype 3B (AAV-3B): insights into receptor binding and immune evasion," Virology 403(1):26-36 (2010).
Li et al. "Construction of phospholamban antisense RNA recombinant adeno-associated Virus vector and its effects in rat cardiomyocytes" Acta Pharmalogica Sinica 26(1).51-55 (2005).
McCarty, D.M., et al., "Self-complementary recombinant adeno-associated virus (scAAV) vectors promote efficient transduction independently of DNA synthesis," Gene Therapy 8, 1248-1254 (2001).
Mingozzi et al., "Overcoming the Host Immune Response to Adeno-Associated Virus Gene Delivery Vectors: The Race Between Clearance, Tolerance, Neutralization, and Escape," Annual Review of Virology 1(1):511-534 (2017).
Miyamura et al. "ParvoVirus particles at platforms for protein presentation" Proceedings of National Academy of Sciences 91:8507-8511 (1995).
Mori et al. "Two novel adeno-associated vires from cynomolgus monkey:pseudotyping characterization of capsid protein," Virology 330:375-383 (2004).
Muramatsu et al. "Nucleotide Sequencing and Generation of an Infectious Clone of Adeno-Associated Virus 3," Virology 22(0367):208-217 (1996).
Nam et al. "Structure of Adeno-Associated Virus Serotype 8, a Gene Therapy Vector" Journal of Virology, 81 (22):12260-12271 (2007).
Ng et al. "Structural Characterization of the Dual Glycan Binding adeno-Associated Virus Serotype 6" Journal of Virology, 84(24):12945-12957 (2010).
Robbins et al., "Recognition of tyrosinase by tumor-infiltrating lymphocytes from a patient responding to immunotherapy," Cancer Res. 54:3124-3126 (1994).
Selot et al., "Developing Immunologically Inert Adeno-Associated Virus (AAV). Vectors for Gene Therapy: Possibilities and Limitations," Current Pharmaceutical Biotechnology, Bentham Science Publishers, NL 14(12). 1072-1082 (2013).
Shade et al. "Nucleotide Sequence and Genome Organization of Human ParvoVirus B19 Isolated from the Serum of a Child during Aplastic Crisis" Journal of Virology 28(3):921-936 (1986).
Smith et al., "Structural Mapping of AAV9 Antigenic Sites and the Engineering of Immune Escape Variants," Molecular Therapy; 20th Annual Meeting of the American Society of Gene and Cell Therapy (ASGCT).; Washington, DC, A; May 10-13, 2017, Nature Publishing Group, GB vol. 25, No. 5, Suppl 1 (2017).

(56) References Cited

OTHER PUBLICATIONS

Srivastava et al. "Nucleotide Sequence and Organization of the adeno-Associated Virus 2 Genome" Journal of Virology 45(2):555-564 (1983).

Tsao et al. The Three-Dimensional Structure of Canine ParvoVirus and Its Functional Implications Science 251(5000):1456-1464 (1991).

Tse et al., "Structure-guided evolution of antigenically distinct adeno-associated Virus variants for immune evasion", Proceedings of the National Academy of Sciences of The United States of America 114(24):E4812-E4821 (2017).

Tse et al., "Strategies to Circumvent Humoral Immunity to Adeno-Associaged Viral Cextors," Expert Opinion on Biological Therapy 15(6):845-855 (2015).

UniProt Accession No. 015118, dated May 30, 2000, 21 pages.

Wang et al. "Adeno-associated Virus vector carrying human minidystrophin genes effectively ameliorates muscular dystrophy in mdx mouse model" Proceedings of the National Academy of Sciences 97(25):13714-13719 (2000).

Work et al., "Vascular bed-targeted in vivo gene delivery using tropism-modified adeno-associated viruses," Molecular Therapy 13(4):683-693 (2006).

Xiao et al. "Gene Therapy Vectors Based on adeno-Associated Virus Type 1" Journal of Virology 73(5):3994-4003 (1999).

Xie et al. "The atomic structure of adeno-associated Virus (AAV-2)., a vector for human gene therapy" Proceeding of the National Academy of Sciences 99(16):10405-1041O (2002).

Xie, J. et al., "Short DNA Hairpins Compromise Recombinant Adeno-Associated Virus Genome Homogeneity," Mol. Ther., 25(6): 1363-1374 (2017).

Zhang et al. "Recombinant AdenoVirus expressing adeno-associated Virus cap and rep proteins supports production of high-titer recombinant adeno-associated virus," Gene Therapy 8:704-712 (2001).

Chandler et al., "Systemic AAV9 gene therapy improves the lifespan of mice with Niemann-Pick disease, type C1," Human Molecular Genetics 26(1):52-64 (2017).

Extended European Search Report issued by the European Patent Office for Application No. 19887003.2, dated Jul. 12, 2022, 10 pages.

Frankel, A.E. et al. (2000). Characterization of diphtheria fusion proteins targeted to the human interleukin-3 receptor, Protein Engineering 13:575-581.

Pakula A.A., et al., "Genetic Analysis of Protein Stability and Function," Annual Review of Genetics, 1989, vol. 23, pp. 289-310.

Xu, D.-H., et al., "SV40 intron, a potent strong intron element that effectively increases transgene expression in transfected Chinese hamster ovary cells," J Cell Mol Med 22(4):2231-2239, Wiley, United States (Apr. 2018).

Protein Data Bank, 5U73, "Crystal structure of human Niemann-Pick C1 protein," published Sep. 27, 2017, 5 pages.

Written Opinion and Search Report for Singapore Application No. 11202203797R, dated Jun. 2, 2025, 13 pages.

* cited by examiner

AAV TRANSFER CASSETTE

CROSS-REFERENCE TO RELATED APPLICATIONS

This application claims priority to U.S. Provisional Application No. 62/923,253, filed on Oct. 18, 2019, and U.S. Provisional Application No. 62/916,749, filed on Oct. 17, 2019, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is STRD_015_02US_SeqList_ST25.txt. The file is ~67.6 kb, was created on Oct. 14, 2020, and is being submitted electronically.

FIELD

The instant disclosure relates to the fields of molecular biology and gene therapy. More specifically, disclosure relates to compositions and methods for producing recombinant viral vectors.

BACKGROUND

Niemann-Pick Disease, type C1 (NPC1) is a neurodegenerative disorder characterized by cholesterol accumulation in endolysosomal compartments. It is caused by mutations in the gene encoding NPC1, an endolysosomal protein mediating intracellular cholesterol trafficking.

NPC1 can present in infants, children, or adults. Neonates can present with ascites and severe liver disease from infiltration of the liver and/or respiratory failure from infiltration of the lungs. Other infants, without liver or pulmonary disease, have hypotonia and developmental delay. The classic presentation occurs in mid-to-late childhood with the insidious onset of ataxia, vertical supranuclear gaze palsy (VSGP), and dementia. Dystonia and seizures are common. Dysarthria and dysphagia eventually become disabling, making oral feeding impossible; death usually occurs in the late second or third decade from aspiration pneumonia. Adults are more likely to present with dementia or psychiatric symptoms.

2-hydroxypropyl-1-cyclodextrin (HPBCD) has been shown to reduce the cholesterol and lipid accumulation and prolongs survival in NPC1 animal models. However, there are no therapies for NPC1 approved by the Food and Drug Administration (FDA). Accordingly, there is an urgent need for compositions and methods for treating, curing, and/or preventing NPC1.

SUMMARY

Described herein are AAV transfer cassettes, nucleic acids and plasmids used in the production of recombinant adeno-associated viral (rAAV) vectors for the delivery of nucleic acids (e.g., nucleic acids comprising transgenes). The disclosed cassettes, nucleic acids and plasmids comprise sequences that may be used to express one or more transgenes having therapeutic efficacy in the amelioration, treatment and/or prevention of one or more diseases or disorders, such as NPC1.

In some embodiments, the disclosure provides an adeno-associated virus (AAV) transfer cassette comprising a 5' inverted terminal repeat (ITR), a promoter, a transgene, a polyadenylation signal, and a 3' ITR, wherein the transfer cassette comprises an intronic sequence. In some embodiments, the intronic sequence is located between the promoter and the transgene. In some embodiments, the transgene encodes the NPC1 protein. In some embodiments, the AAV transfer cassette comprises the sequence of any one of SEQ ID NO: 14-19.

In some embodiments, the disclosure provides a recombinant AAV vector comprising a protein capsid and a nucleic acid encapsidated by the protein capsid, wherein the nucleic acid comprises an transfer cassette comprising, from 5' to 3', a 5' inverted terminal repeat (ITR); a promoter; a transgene; a polyadenylation signal; and a 3' ITR. In some embodiments, the transfer cassette comprises an intronic sequence, such as an intronic sequence located between the promoter and the transgene. In some embodiments, the transgene encodes the NPC1 protein. In some embodiments, the AAV transfer cassette comprises the sequence of any one of SEQ ID NO: 14-19.

In some embodiments, at least one of the 5' ITR and the 3' ITR is about 110 to about 160 nucleotides in length. In some embodiments, the 5' ITR is the same length as the 3' ITR. In some embodiments, the 5' ITR and the 3' ITR have different lengths. At least one of the 5' ITR and the 3' ITR may be isolated or derived from, for example, the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, the 5' ITR comprises the sequence of SEQ ID NO: 3, or a sequence at least 95%, at least 96%, at least 97%, at least 98%, or at least 99% identical thereto. In some embodiments, the 3' ITR comprises the sequence of SEQ ID NO: 4, or a sequence that is at least 95%, at least 96%, at least 97%, at least 98%, or at least 99% identical thereto.

In some embodiments, the promoter is a constitutive promoter. In some embodiments, the promoter is an inducible promoter. In some embodiments, the promoter is a tissue-specific promoter. In some embodiments, the promoter may be selected from the group consisting of the CBA promoter, the GUSB240 promoter, the GUSB379 promoter, the HSVTK promoter, the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the EF-1 alpha promoter, the EF-1 short promoter, the dihydrofolate reductase (DHFR) promoter, and the phosphoglycerol kinase (PGK) promoter. In some embodiments, the promoter is selected from the group consisting of the CBA promoter, the GUSB240 promoter, the GUSB379 promoter, and the HSVTK promoter. In some embodiments, the promoter comprises a sequence at least 95%, at least 96%, at least 97%, at least 98% at least 99%, or 100% identical to any one of SEQ ID NO: 5-8.

In some embodiments, the intronic sequence is a chimeric sequence or a hybrid sequence. In some embodiments, the intronic sequence comprises sequences isolated or derived from SV40. In some embodiments, the intronic sequence comprises the sequence of any one of SEQ ID NO: 10-11.

The NPC1 protein may be, for example, the human NPC1 protein. In some embodiments, the NPC1 protein has a sequence that is at least 90%, at least 95%, at least 95%, at least 97%, at least 98%, or at least 99% identical to the sequence of the human NPC1 protein. In some embodiments, the NPC1 protein comprises the sequence of SEQ ID NO: 1, or a sequence at least 95%, at least 96%, at least 97%, at least 98%, or at least 99% identical thereto. In some embodiments, the NPC1 protein comprises the sequence of SEQ ID NO: 20, or a sequence at least 95%, at least 96%, at least 97%, at least 98%, or at least 99% identical thereto. In some embodiments, the NPC1 protein (Niemann-Pick intracellular cholesterol transporter 1) has a sequence as shown in UniProt Accession No. 015118, incorporated herein by reference in its entirety.

In some embodiments, the transgene comprises a sequence of SEQ ID NO: 2, or a sequence at least 95%, at least 96%, at least 97%, at least 98%, or at least 99% identical thereto.

In some embodiments, the polyadenylation signal is selected from simian virus 40 (SV40), rabbit beta globin (rBG), α-globin, β-globin, human collagen, human growth hormone (hGH), polyoma virus, human growth hormone (hGH) and bovine growth hormone (bGH). In some embodiments, the polyadenylation signal is the SV40 polyadenylation signal. In some embodiments, the polyadenylation signal is the rBG polyadenylation signal. In some embodiments, the polyadenylation signal comprises the sequence of SEQ ID NO: 12 or SEQ ID NO: 13. In some embodiments, the polyadenylation signal comprises a sequence at least 95%, at least 96%, at least 97%, at least 98%, or at least 99% identical to SEQ ID NO: 12 or 13.

In some embodiments, the AAV transfer cassette further comprises an enhancer. The enhancer may be, for example, the CMV enhancer. In some embodiments, the enhancer comprises the sequence of SEQ ID NO: 9, or a sequence at least 95%, at least 96%, at least 97%, at least 98%, or at least 99% identical thereto.

Also provided herein is a nucleic acid comprising an AAV transfer cassette of the disclosure. Also provided herein is a plasmid or bacmid comprising an AAV transfer cassette of the disclosure.

Also provided herein is a recombinant AAV vector comprising a protein capsid and a nucleic acid encapsidated by the protein capsid, wherein the nucleic acid comprises an AAV transfer cassette of the disclosure.

Also provided is a cell comprising the AAV transfer cassette of the disclosure.

Also provided is a method of producing a recombinant AAV vector, the method comprising contacting an AAV producer cell with an AAV transfer cassette or plasmid/bacmid of the disclosure. Also provided is a recombinant AAV vector produced by this method. The recombinant AAV vector may be of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV. The recombinant AAV vector may comprise a protein capsid comprising a capsid protein subunit, wherein the capsid protein subunit comprises one or more mutations compared to a capsid protein subunit of a wildtype AAV.

Also provided are compositions comprising an AAV transfer cassette, a nucleic acid (e.g., a plasmid or a bacmid), a cell, or a recombinant AAV vector of the disclosure.

Also provided is a method for treating a subject in need thereof comprising administering to the subject a therapeutically effective amount of an AAV transfer cassette, a nucleic acid (e.g., a plasmid), a cell, or a recombinant AAV vector of the disclosure. In some embodiments, the subject is a human subject. In some embodiments, the subject has NPC1.

These and other embodiments are addressed in more detail in the detailed description set forth below.

DETAILED DESCRIPTION

Figure 1B:
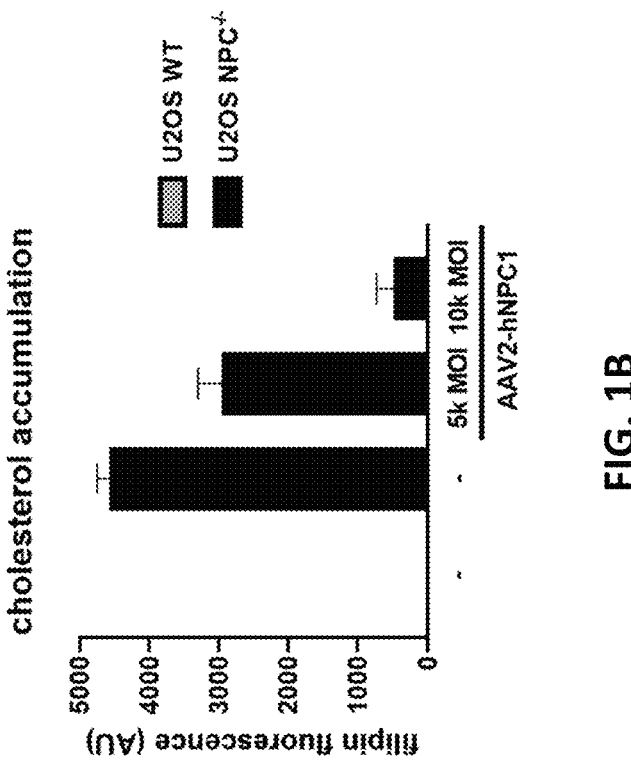
FIG. 1B is a graph that shows cholesterol accumulation, as determined using filipin staining, in wildtype U2OS cells, NPC1-deficient (NPC1$^{-/-}$) U2OS cells, and NPC1$^{-/-}$ cells transduced with AAV2-hNPC at a Multiplicity of Infection (MOI) of either $5 \times 10^3$ or $10 \times 10^3$. Statistical significance determined using one-way ANOVA. Error bars represent SEM.

Provided herein are gene therapy compositions and methods for treating, preventing, and/or curing NPC1. More specifically, the disclosure provides Adeno-associated virus (AAV) vectors for the delivery of nucleic acids, e.g. transgenes, and nucleic acids (including AAV transfer cassettes) for treating, preventing, and/or curing NPC1.

AAVs are useful as gene delivery agents, and are powerful tools for human gene therapy. Using AAVs, high-frequency DNA delivery and stable expression may be achieved in a variety of cells, both in vivo and in vitro. Unlike some other viral vector systems, AAV does not require active cell division for stable integration in target cells.

All papers, publications and patents cited in this specification are herein incorporated by reference as if each individual paper, publication or patent were specifically and individually indicated to be incorporated by reference and are incorporated herein by reference to disclose and describe the methods and/or materials in connection with which the publications are cited.

Unless the context indicates otherwise, it is specifically intended that the various features described herein can be used in any combination.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

Definitions

The following terms are used in the description herein and the appended claims:

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

A "nucleic acid" or "polynucleotide" is a sequence of nucleotide bases, for example RNA, DNA or DNA-RNA hybrid sequences (including both naturally occurring and non-naturally occurring nucleotides). In some embodiments, the nucleic acids of the disclosure are either single or double stranded DNA sequences. A nucleic acid may be 1-1,000, 1,000-10,000, 10,000-100,000, 100,000-1 million or greater than 1 million nucleotides in length. A nucleic acid will generally contain phosphodiester bonds, although in some cases nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include those with positive backbones, non-ionic backbones, and non-ribose backbones. Nucleic acids containing one or more carbocyclic sugars are also included within the definition of nucleic acids. These modifications of the ribose-phosphate backbone may facilitate the addition of labels, or to increase the stability and half-life of such molecules in physiological environments. Nucleic acids of the disclosure may be linear, or may be circular (e.g., a plasmid).

An "AAV transfer cassette" is a nucleic acid that may be used in the generation of an AAV vector.

As used herein, the terms "virus vector," or "viral vector" refer to a virus particle that functions as a nucleic acid delivery vehicle, and which comprises a nucleic acid (e.g., a nucleic acid comprising a transgene) packaged within a virion or virus-like particle. Exemplary virus vectors of the disclosure include adenovirus vectors, adeno-associated virus vectors (AAVs), lentivirus vectors, and retrovirus vectors.

An "adeno-associated virus vector" or "AAV vector" typically comprises a protein capsid, and a nucleic acid (e.g., a nucleic acid comprising a transgene) encapsidated by the protein capsid. The "protein capsid" is a near-spherical protein shell that comprises individual "capsid protein subunits" (e.g., about 60 capsid protein subunits) associated and arranged with T=1 icosahedral symmetry. The protein capsids of the AAV vectors described herein comprise a plurality of capsid protein subunits. When an AAV vector is described herein as comprising an AAV capsid protein subunit, it will be understood that the AAV vector comprises a protein capsid, wherein the protein capsid comprises one or more AAV capsid protein subunits. As used herein, the term "capsid protein" is sometimes used to refer to a capsid protein subunit. The term "viral-like particle" or "virus-like particle" refers to a protein capsid that does not comprise any vector genome or nucleic acid comprising a transfer cassette or transgene.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, AAV type rh74, AAV type hu.68, avian AAV, bovine AAV, canine AAV, equine AAV, ovine AAV, snake AAV, bearded dragon AAV, AAV2i8, AAV2g9, AAV-LK03, AAV7m8, AAV Anc80, AAV PHP.B, and any other AAV now known or later discovered. See, e.g., Table 1.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862, AAB95450.1 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AAT46339, AY631966 |
| AAV12 | ABI16639, DQ813647 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |

TABLE 1-continued

| GenBank Accession Number | |
| --- | --- |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| HSC1 | MI332400.1 |
| HSC2 | MI332401.1 |
| HSC3 | MI332402.1 |

TABLE 1-continued

| GenBank Accession Number | |
| --- | --- |
| HSC4 | MI332403.1 |
| HSC5 | MI332405.1 |
| HSC6 | MI332404.1 |
| HSC7 | MI332407.1 |
| HSC8 | MI332408.1 |
| HSC9 | MI332409.1 |
| HSC11 | MI332406.1 |
| HSC12 | MI332410.1 |
| HSC13 | MI332411.1 |
| HSC14 | MI332412.1 |
| HSC15 | MI332413.1 |
| HSC16 | MI332414.1 |
| HSC17 | MI332415.1 |
| Hu68 | |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |
| Others | |
| Rh74 | |
| Bearded Dragon AAV | |
| Snake AAV | NC_006148.1 |

Recombinant AAV (rAAV) vectors can be produced in culture using viral production cell lines. The terms "viral production cell", "viral production cell line," or "viral producer cell" refer to cells used to produce viral vectors. HEK293 and 239T cells are common viral production cell lines. Table 2, below, lists exemplary viral production cell lines for various viral vectors. Production of rAAVs typically requires the presence of three elements in the cells: 1) a transgene flanked by AAV inverted terminal repeat (ITR) sequences, 2) AAV rep and cap genes, and 3) helper virus protein sequences. These three elements may be provided on one or more plasmids, and transfected or transduced into the cells.

TABLE 2

| Exemplary viral production cell lines | |
| --- | --- |
| Virus Vector | Exemplary Viral Production Cell Line(s) |
| Adenovirus | HEK293, 911, pTG6559, PER.C6, GH329, N52.E6, HeLa-E1, UR, VLI-293 |
| Adeno-Associated Virus (AAV) | HEK293, Sf9 |
| Retrovirus | HEK293 |
| Lentivirus | 293T |

"HEK293" refers to a cell line originally derived from human embryonic kidney cells grown in tissue culture. The HEK293 cell line grows readily in culture, and is commonly used for viral production. As used herein, "HEK293" may also refer to one or more variant HEK293 cell lines, i.e., cell lines derived from the original HEK293 cell line that additionally comprise one or more genetic alterations. Many variant HEK293 lines have been developed and optimized for one or more particular applications. For example, the 293T cell line contains the SV40 large T-antigen that allows for episomal replication of transfected plasmids containing the SV40 origin of replication, leading to increased expression of desired gene products.

"Sf9" refers to an insect cell line that is a clonal isolate derived from the parental *Spodoptera frugiperda* cell line IPLB-Sf-21-AE. Sf9 cells can be grown in the absence of serum and can be cultured attached or in suspension.

A "transfection reagent" means a composition that enhances the transfer of nucleic acid into cells. Some transfection reagents commonly used in the art include one or more lipids that bind to nucleic acids and to the cell surface (e.g., Lipofectamine™).

As used herein, the term "multiplicity of infection" or "MOI" refers to number of virions contacted with a cell. For example, cultured cells may be contacted with AAVs at an MOI in the range of $1\times10^2$ to $1\times10^5$ virions per cell.

As used herein, an "effective amount" is the amount of an AAV vector, nucleic acid, or other agent provided herein that is effective to treat or prevent a disease or disorder in a subject or to ameliorate a sign or symptom thereof. The "effective amount" may vary depending, for example, on the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or may be capable of determination by routine experimentation.

Methods of determining sequence similarity or identity between two or more amino acid sequences are known in the art. Sequence similarity or identity may be determined for the entire length of a nucleic acid or an indicated portion of a nucleic acid. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48, 443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection.

Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al, (1997) Nucleic Acids Res. 25, 3389-3402.

For purposes of the instant disclosure, unless otherwise indicated, percent identity is calculated using the Basic Local Alignment Search Tool (BLAST) available online at blast.ncbi.nlm.nih.gov/Blast.cgi. The skilled artisan will understand that other algorithms may be substituted as appropriate.

Inverted Terminal Repeat

Inverted Terminal Repeat or ITR sequences are sequences that mediate AAV proviral integration and for packaging of AAV DNA into virions. ITRs are involved in a variety of activities in the AAV life cycle. For example, the ITR sequences, which can form a hairpin structure, play roles in excision from the plasmid after transfection, replication of the vector genome, and integration and rescue from a host cell genome.

The AAV transfer cassettes of the disclosure may comprise a 5' ITR and a 3' ITR. The ITR sequences may be about 110 to about 160 nucleotides in length, for example 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159 or 160 nucleotides in length. In some embodiments, the ITR sequences may be about 141 nucleotides in length. In some embodiments, the 5' ITR is the same length as the 3' ITR. In some embodiments, the 5' ITR and the 3' ITR have different lengths. In some embodiments, the 5' ITR is longer than the 3' ITR, and in other embodiments, the 3' ITR is longer than the 5' ITR.

The ITRs may be isolated or derived from the genome of any AAV, for example the AAVs listed in Table 1. In some embodiments, at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, at least one of the 5' ITR and the 3'ITR may be a wildtype or mutated ITR isolated derived from a member of another parvovirus species besides AAV. For example, in some embodiments, an ITR may be a wildtype or mutant ITR isolated or derived from bocavirus or parvovirus B19.

In some embodiments, the ITR comprises a modification to promote production of a scAAV. In some embodiments, the modification to promote production of a scAAV is deletion of the terminal resolution sequence (TRS) from the ITR. In some embodiments, the 5' ITR is a wildtype ITR, and the 3' ITR is a mutated ITR lacking the terminal resolution sequence. In some embodiments, the 3' ITR is a wildtype ITR, and the 5' ITR is a mutated ITR lacking the terminal resolution sequence. In some embodiments, the terminal resolution sequence is absent from both the 5' ITR and the 3'ITR. In other embodiments, the modification to promote production of a scAAV is replacement of an ITR with a different hairpin-forming sequence, such as a shRNA-forming sequence.

In some embodiments, the 5' ITR may comprise the sequence of SEQ ID NO: 3, or a sequence at least 95% identical thereto. In some embodiments, the 3' ITR may comprise the sequence of SEQ ID NO: 4, or a sequence at least 95% identical thereto. In some embodiments, the 5' ITR comprises the sequence of SEQ ID NO: 3, and the 3' ITR comprises the sequence of SEQ ID NO: 4.

In some embodiments, the AAV transfer cassettes comprise one or more "surrogate" ITRs, i.e., non-ITR sequences that serve the same function as ITRs. See, e.g., Xie, J. et al., Mol. Ther., 25(6): 1363-1374 (2017). In some embodiments, an ITR in an AAV transfer cassette is replaced by a surrogate ITR. In some embodiments, the surrogate ITR comprises a hairpin-forming sequence. In some embodiments, the surrogate ITR is a short hairpin (sh)RNA-forming sequence.

Promoters, Enhancers, Repressors and Other Regulatory Sequences

Gene expression may be controlled by nucleotide sequences called promoters and enhancers that flank the coding region for a given protein.

As used herein, the term "promoter" refers to one or more nucleic acid control sequences that direct transcription of an operably linked nucleic acid. Promoters may include nucleic acid sequences near the start site of transcription, such as a TATA element. Promoters may also include cis-acting poly- [5] nucleotide sequences that can be bound by transcription factors.

A "constitutive" promoter is a promoter that is active under most environmental and developmental conditions. An "inducible" promoter is a promoter that is active under [10] environmental or developmental regulation. The term "operably linked" refers to a functional linkage between a nucleic acid expression control sequence (such as a promoter, or array of transcription factor binding sites) and a second nucleic acid sequence, wherein the expression control [15] sequence directs transcription of the nucleic acid corresponding to the second sequence.

Gene expression may also be controlled by one or more distal "enhancer" or "repressor" elements, which can be located as much as several thousand base pairs from the start [20] site of transcription. Enhancer or repressor elements regulate transcription in an analogous manner to cis-acting elements near the start site of transcription, with the exception that enhancer elements can act from a distance from the start site of transcription. [25]

In some embodiments, the AAV transfer cassettes described herein comprise a promoter. They promoter may be, for example, a constitutive promoter or an inducible promoter. In some embodiments, the promoter is a tissue-specific promoter. [30]

Exemplary promoters that may be used in the AAV transfer cassettes described herein include the CMV promoter, the SV40 early promoter, the SV40 late promoter, the metallothionein promoter, the murine mammary tumor virus (MMTV) promoter, the Rous sarcoma virus (RSV) pro- [35] moter, the polyhedrin promoter, the chicken β-actin (CBA) promoter, the dihydrofolate reductase (DHFR) promoter, and the phosphoglycerol kinase (PGK) promoter. In some embodiments, the promoter is selected from the group consisting of the chicken β-actin (CBA) promoter the EF-1 [40] alpha promoter, and the EF-1 alpha short promoter. In some embodiments, the promoter comprises a sequence selected from any one of SEQ ID NO: 5-8, or a sequence at least 95% identical thereto.

In some embodiments, the AAV transfer cassettes [45] described herein comprise an enhancer. The enhancer may be, for example, the CMV enhancer. In some embodiments, the enhancer comprises the sequence of SEQ ID NO: 9, or a sequence at least 95% identical thereto.

A non-limiting list of exemplary tissue-specific promoters [50] and enhancers that may be used in the AAV transfer cassettes described herein includes: HMG-COA reductase promoter; sterol regulatory element 1 (SRE-1); phosphoenol pyruvate carboxy kinase (PEPCK) promoter; human C-reactive protein (CRP) promoter; human glucokinase promoter; choles- [55] terol 7-alpha hydroylase (CYP-7) promoter; beta-galactosidase alpha-2,6 sialyltransferase promoter; insulin-like growth factor binding protein (IGFBP-1) promoter; aldolase B promoter; human transferrin promoter; collagen type I promoter; prostatic acid phosphatase (PAP) promoter; pro- [60] static secretory protein of 94 (PSP 94) promoter; prostate specific antigen complex promoter; human glandular kallikrein gene promoter (hgt-1); the myocyte-specific enhancer binding factor MEF-2; muscle creatine kinase promoter; pancreatitis associated protein promoter (PAP); [65] elastase 1 transcriptional enhancer; pancreas specific amylase and elastase enhancer promoter; pancreatic cholesterol esterase gene promoter; uteroglobin promoter; cholesterol side-chain cleavage (SCC) promoter; gamma-gamma enolase (neuron-specific enolase, NSE) promoter; neurofilament heavy chain (NF-H) promoter; human CGL-1/granzyme B promoter; the terminal deoxy transferase (TdT), lambda 5, VpreB, and Ick (lymphocyte specific tyrosine protein kinase p561ck) promoter; the humans CD2 promoter and its 3' transcriptional enhancer; the human NK and T cell specific activation (NKGS) promoter; pp60c-src tyrosine kinase promoter; organ-specific neoantigens (OSNs), mw 40 kDa (p40) promoter; colon specific antigen-P promoter; human alpha-lactalbumin promoter; phosphoeholpyruvate carboxykinase (PEPCK) promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, alpha or beta globin promoter, T-cell receptor promoter, the osteocalcin promoter the IL-2 promoter, IL-2 receptor promoter, whey (wap) promoter, and the MHC Class II promoter.

Transgene

The AAV transfer cassettes described herein comprise a transgene for expression in a target cell.

The transgene may be any heterologous nucleic acid sequence(s) of interest. Such nucleic acids may include nucleic acids encoding polypeptides, including therapeutic (e.g., for medical or veterinary uses) or immunogenic (e.g., for vaccines) polypeptides or RNAs. Alternatively, the nucleic acid may encode an antisense nucleic acid, a ribozyme, RNAs that effect spliceosome-mediated/ramsplicing, interfering RNAs (RNAi) including siRNA, shRNA or miRNA that mediate gene silencing, and other non-translated RNAs. In some embodiments, the nucleic acid sequence may direct gene editing. For example, the nucleic acid may encode a gene-editing molecule such as a guide RNA or a nuclease. In some embodiments, the nucleic acid may encode a zinc-finger nuclease, a homing endonuclease, a TALEN (transcription activator-like effector nuclease), a NgAgo (agronaute endonuclease), a SGN (structure-guided endonuclease), or a RGN (RNA-guided nuclease) such as a Cas9 nuclease or a Cpf1 nuclease. In some embodiments, the nucleic acid may share homology with and recombine with a locus on a host chromosome. This approach can be utilized, for example, to correct a genetic defect in the host cell.

The virus vectors according to the present disclosure provide a means for delivering transgenes into a broad range of cells, including dividing and non-dividing cells. The virus vectors can be employed to deliver a transgene to a cell in vitro, e.g., to produce a polypeptide in vitro or for ex vivo gene therapy. The virus vectors are additionally useful in a method of delivering a transgene to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect. As used herein, the term "functional RNA" refers to any non-coding RNA sequence that has one or more functions in a cell, such as those described in the preceding paragraph.

The virus vectors can also be used to deliver nucleic acids for the production of a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present disclosure can be employed to deliver a transgene encoding a polypeptide or functional RNA to treat and/or prevent any disease state for which it is beneficial to deliver a therapeutic polypeptide or functional RNA.

In some embodiments, the transgene is useful for treating NPC1. In some embodiments, the transgene encodes the NPC1 protein. The NPC1 protein may be, for example, the human NPC1 protein. In some embodiments, the NPC1 protein has a sequence that is at least 90% identical, at least 95% identical, or at least 98% identical to the sequence of the human NPC1 protein. In some embodiments, the NPC1 protein comprises one or more of the single amino acid changes listed in Table 3 (numbering based on SEQ ID NO: 1). In some embodiments, the NPC1 protein comprises one or more of the amino acid changes listed in Table 3 (numbering based on SEQ ID NO: 20). In some embodiments, the NPC1 protein is a truncated form of the human NPC1 protein. In some embodiments, the NPC1 protein comprises the sequence of SEQ ID NO: 1, or a sequence at least 90% identical, at least 95% identical, at least 96% identical, at least 97% identical, at least 98% identical, or at least 99% identical thereto. In some embodiments, the NPC1 protein comprises the sequence of SEQ ID NO: 20, or a sequence at least 90% identical, at least 95% identical, at least 96% identical, at least 97% identical, at least 98% identical, or at least 99% identical thereto. In some embodiments, the NPC1 protein comprises the sequence of SEQ ID NO: 1 or 20, with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acid changes relative thereto. In some embodiments, the NPC1 protein comprises the sequence of SEQ ID NO: 1 or 20, with one or more of the amino acid changes listed in Table 3. In some embodiments, the transgene encodes the amino acid sequence of SEQ ID NO: 1. In some embodiments, the transgene encodes the amino acid sequence of SEQ ID NO: 20.

In some embodiments, the transgene comprises the sequence of SEQ ID NO: 2, or a sequence at least 90% identical, at least 95% identical, at least 96% identical, at least 97% identical, at least 98% identical, or at least 99% identical thereto. In some embodiments, the transgene comprises the sequence of SEQ ID NO: 2, or a sequence with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acid changes relative thereto.

TABLE 3

NPC1 Variant Sequences
Position numbering based on SEQ ID NO: 1 or SEQ ID NO: 20.

| Position | Mutation |
|---|---|
| 63 | C→R |
| 74 | C→Y |
| 92 | Q→R |
| 113 | C→R |
| 137 | T→M |
| 151 | S→G |
| 166 | P→S |
| 177 | C→G |
| 177 | C→Y |
| 215 | H→R |
| 222 | N→S |

14

TABLE 3-continued

NPC1 Variant Sequences
Position numbering based on SEQ ID NO: 1 or SEQ ID NO: 20.

| Position | Mutation |
|---|---|
| 231 | V→G |
| 237 | P→S |
| 242 | D→H |
| 242 | D→N |
| 247 | C→Y |
| 248 | G→V |
| 272 | M→R |
| 333 | G→D |
| 372 | R→W |
| 378 | V→A |
| 380 | L→F |
| 381 | W→C |
| 388 | A→P |
| 389 | R→C |
| 401 | P→T |
| 404 | R→P |
| 404 | R→Q |
| 404 | R→W |
| 433 | P→L |
| 434 | P→L |
| 434 | P→S |
| 451 | E→K |
| 472 | L→P |
| 473 | S→P |
| 474 | P→L |
| 479 | C→Y |
| 509 | Y→S |
| 510 | H→P |
| 511 | T→M |
| 512 | H→R |
| 518 | R→Q |
| 518 | R→W |
| 521 | A→S |
| 537 | F→L |
| 543 | P→L |
| 574 | T→K |
| 576 | K→R |
| 605 | A→V |
| 612 | E→D |
| 615 | R→C |
| 615 | R→L |
| 631 | M→R |
| 640 | G→R |
| 642 | M→I |
| 652 | S→W |
| 660 | G→S |
| 664 | V→M |
| 666 | S→N |
| 670 | C→W |
| 673 | G→V |
| 684 | L→F |
| 691 | P→L |
| 695 | L→V |
| 700 | D→N |
| 703 | F→S |
| 724 | L→P |
| 727 | V→F |
| 734 | S→I |
| 742 | E→K |
| 745 | A→E |
| 754 | M→K |
| 757 | V→A |
| 763 | F→L |
| 767 | A→V |
| 775 | Q→P |
| 789 | R→C |
| 789 | R→G |
| 825 | Y→C |
| 849 | S→I |
| 858 | I→V |
| 862 | Q→L |
| 865 | S→L |
| 871 | Y→C |
| 873 | V→A |
| 874 | D→V |

TABLE 3-continued

| NPC1 Variant Sequences Position numbering based on SEQ ID NO: 1 or SEQ ID NO: 20. | |
| --- | --- |
| Position | Mutation |
| 888 | P→S |
| 889 | V→M |
| 890 | Y→C |
| 899 | Y→D |
| 910 | G→S |
| 917 | D→Y |
| 926 | A→T |
| 927 | A→V |
| 928 | Q→P |
| 929 | L→P |
| 934 | R→Q |
| 940 | S→L |
| 942 | W→C |
| 943 | I→M |
| 944 | D→N |
| 945 | D→N |
| 948 | D→H |
| 948 | D→N |
| 948 | D→Y |
| 950 | V→M |
| 954 | S→L |
| 956 | C→Y |
| 958 | R→L |
| 958 | R→Q |
| 959 | V→E |
| 961-966 | NITDQF→S |
| 961 | N→S |
| 968 | N→S |
| 971 | V→G |
| 976 | C→R |
| 978 | R→C |
| 986 | G→S |
| 992 | G→A |
| 992 | G→R |
| 992 | G→W |
| 996 | M→R |
| 1004 | S→L |
| 1007 | P→A |
| 1012 | G→D |
| 1015 | G→V |
| 1016 | H→R |
| 1023 | V→G |
| 1034 | G→R |
| 1035 | A→V |
| 1036 | T→K |
| 1036 | T→M |
| 1049 | A→V |
| 1054 | A→T |
| 1059 | R→Q |
| 1061 | I→T |
| 1062 | A→V |
| 1066 | T→N |
| 1087 | F→L |
| 1088 | Y→C |
| 1089 | E→K |
| 1094 | I→T |
| 1097 | D→N |
| 1137 | N→I |
| 1140 | G→V |
| 1142 | M→T |
| 1150 | N→K |
| 1156 | N→I |
| 1156 | N→S |
| 1165 | V→M |
| 1167 | F→L |
| 1168 | C→Y |
| 1174 | A→V |
| 1186 | R→H |
| 1189 | E→G |
| 1205 | T→K |
| 1205 | T→R |
| 1212 | V→L |
| 1213 | L→F |
| 1213 | L→V |
| 1216 | A→V |

TABLE 3-continued

| NPC1 Variant Sequences Position numbering based on SEQ ID NO: 1 or SEQ ID NO: 20. | |
| --- | --- |
| Position | Mutation |
| 1220 | I→T |
| 1224 | F→L |
| 1236 | G→E |
| 1240 | G→R |
| 1249 | S→G |
| 1266 | R→Q |

Polyadenylation (PolyA) Signal

Polyadenylation signals are nucleotide sequences found in nearly all mammalian genes and control the addition of a string of approximately 200 adenosine residues (the poly(A) tail) to the 3' end of the gene transcript. The poly(A) tail contributes to mRNA stability, and mRNAs lacking the poly(A) tail are rapidly degraded. There is also evidence that the presence of the poly(A) tail positively contributes to the translatability of mRNA by affecting the initiation of translation.

In some embodiments, the AAV transfer cassettes of the disclosure comprise a polyadenylation signal. The polyadenylation signal may be selected from the polyadenylation signal of simian virus 40 (SV40), α-globin, β-globin, human collagen, human growth hormone (hGH), polyoma virus, human growth hormone (hGH) and bovine growth hormone (bGH). In some embodiments, the polyadenylation signal is the SV40 polyadenylation signal. In some embodiments, the polyadenylation signal is the rBG polyadenylation signal. In some embodiments, the polyadenylation signal comprises the sequence of SEQ ID NO: 12 or SEQ ID NO: 13. In some embodiments, the polyadenylation signal comprises a sequence at least 90%, at least 95%, at least 96%, at least 97%, at least 98%, or at least 99% identical to the sequence of SEQ ID NO: 12 or SEQ ID NO: 13.

Stuffer Sequences

AAV vectors typically accept inserts of DNA having a defined size range, generally in the range of about 4 kb to about 5.2 kb, or slightly more. Thus, for shorter transgene sequences, it may be necessary to include additional nucleic acids in order to achieve the required length which is acceptable for the AAV vector. Accordingly, in some embodiments, the AAV transfer cassettes of the disclosure may comprise a stuffer sequence. The stuffer sequence may be for example, a sequence between 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, to 4,500-5,000 nucleotides in length. The stuffer sequence can be located in the cassette at any desired position such that it does not prevent a function or activity of the vector.

Intronic Sequences

In some embodiments, the AAV transfer cassettes of the disclosure may comprise an intronic sequence. Inclusion of an intronic sequence may enhance expression compared with expression in the absence of the intronic sequence. In some the intronic sequence can increase gene expression without functioning as a binding site for transcription factors. For example, the intronic sequence can increase transcript levels by affecting the rate of transcription, nuclear export, and transcript stability. In some embodiments, the intronic sequence increases the efficiency of mRNA translation.

In some embodiments, the intronic sequence is a hybrid or chimeric sequence. In some embodiments, the intronic sequence is isolated or derived from an intronic sequence of one or more of SV40, β-globin, chicken beta-actin, minute virus of mice (MVM), factor IX, and/or human IgG (heavy or light chain). In some embodiments, the intronic sequence is isolated or derived from SV40. In some embodiments, the intronic sequence is chimeric. In some embodiments, the intronic sequence comprises the sequence of SEQ ID NO: 10 or SEQ ID NO: 11, or a sequence that is at least 90%, at least 95%, at least 96%, at least 97%, at least 98%, or at least 99% identical thereto.

The intronic sequence may be located anywhere in the transfer cassette where it doesn't interfere with production of the AAV vector. For example, in some embodiments, the intronic sequence may be located between the promoter and the transgene.

AAV Transfer Cassettes

In some embodiments, an adeno-associated virus (AAV) transfer cassette comprises a 5' inverted terminal repeat (ITR), a promoter, a transgene, a polyadenylation signal, and a 3' ITR. In some embodiments, the transfer cassette comprises an intronic sequence, such as an intronic sequence between the promoter and the transgene. In some embodiments, the transgene encodes the NPC1 protein. In some embodiments, the AAV transfer cassette comprises an enhancer. In some embodiments, the AAV transfer cassette comprises an intronic sequence. In some embodiments, the 5' ITR comprises the sequence of SEQ ID NO: 3 and the 3' ITR comprises the sequence of SEQ ID NO: 4. In some embodiments, the enhancer comprises the sequence of SEQ ID NO: 9. In some embodiments, the promoter comprises the sequence of any one of SEQ ID NO: 5-8. In some embodiments, the intronic sequence comprises the sequence of SEQ ID NO: 10 or 11. In some embodiments, the transgene comprises the sequence of SEQ ID NO: 2. In some embodiments, the polyA signal comprises the sequence of SEQ ID NO: 12 or 13. In some embodiments, the AAV transfer cassette comprises the sequence of any one of SEQ ID NO: 14-19. In some embodiments, the AAV transfer cassette comprises the sequence of SEQ ID NO: 14.

In some embodiments, an AAV transfer cassette comprises a 5' ITR, a CBA promoter, a SV40 intron, a transgene encoding the NPC1 protein, a SV40 polyadenylation signal, and a 3' ITR. In some embodiments, an AAV transfer cassette comprises a 5' ITR, a GUSB240 promoter, a chimeric intron, a transgene encoding the NPC1 protein, a rBG polyadenylation signal, and a 3' ITR. In some embodiments, an AAV transfer cassette comprises a 5' ITR, a GUSB379 promoter, a SV40 intron, a transgene encoding the NPC1 protein, a rBG polyadenylation signal, and a 3' ITR. In some embodiments, an AAV transfer cassette comprises a 5' ITR, a GUSB240 promoter, a chimeric intron, a transgene encoding the NPC1 protein, a SV40 polyadenylation signal, and a 3' ITR. In some embodiments, an AAV transfer cassette comprises a 5' ITR, a GUSB240 promoter, a SV40 intron, a transgene encoding the NPC1 protein, a SV40 polyadenylation signal, and a 3' ITR. In some embodiments, an AAV transfer cassette comprises a 5' ITR, a CMV enhancer, a HSVTK promoter, a transgene encoding the NPC1 protein, a rBG polyadenylation signal, and a 3' ITR.

In some embodiments, an AAV transfer cassette comprises a 5' ITR comprising the sequence of SEQ ID NO: 3, a CBA promoter comprising the sequence of SEQ ID NO: 5, a SV40 intron comprising the sequence of SEQ ID NO: 10, a transgene encoding the NPC1 protein (SEQ ID NO: 1), a SV40 polyadenylation signal comprising SEQ ID NO: 12, and a 3' ITR comprising the sequence of SEQ ID NO: 4.

In some embodiments, an AAV transfer cassette comprises a 5' ITR comprising the sequence of SEQ ID NO: 3, a GUSB240 promoter comprising the sequence of SEQ ID NO: 6, a chimeric intron comprising SEQ ID NO: 11, a transgene encoding the NPC1 protein (SEQ ID NO: 1), a rBG polyadenylation signal comprising SEQ ID NO: 13, and a 3' ITR comprising the sequence of SEQ ID NO: 4.

In some embodiments, an AAV transfer cassette comprises a 5' ITR comprising the sequence of SEQ ID NO: 3, a GUSB379 promoter comprising SEQ ID NO: 6, a SV40 intron comprising the sequence of SEQ ID NO: 10, a transgene encoding the NPC1 protein (SEQ ID NO: 1), a rBG polyadenylation signal comprising SEQ ID NO: 13, and a 3' ITR comprising the sequence of SEQ ID NO: 4.

In some embodiments, an AAV transfer cassette comprises a 5' ITR comprising the sequence of SEQ ID NO: 3, a GUSB240 promoter comprising SEQ ID NO: 7, a chimeric intron comprising the sequence of SEQ ID NO: 11, a transgene encoding the NPC1 protein (SEQ ID NO: 1), a SV40 polyadenylation signal comprising SEQ ID NO: 12, and a 3' ITR comprising the sequence of SEQ ID NO: 4.

In some embodiments, an AAV transfer cassette comprises a 5' ITR comprising the sequence of SEQ ID NO: 3, a GUSB240 promoter comprising SEQ ID NO: 6, a SV40 intron comprising the sequence of SEQ ID NO: 10, a transgene encoding the NPC1 protein (SEQ ID NO: 1), a SV40 polyadenylation signal comprising SEQ ID NO: 12, and a 3' ITR comprising the sequence of SEQ ID NO: 4.

In some embodiments, an AAV transfer cassette comprises a 5' ITR comprising the sequence of SEQ ID NO: 3, a CMV enhancer, a HSVTK promoter comprising SEQ ID NO: 8, a transgene encoding the NPC1 protein (SEQ ID NO: 1), a rBG polyadenylation signal comprising SEQ ID NO: 13, and a 3' ITR comprising the sequence of SEQ ID NO: 4.

In some embodiments, a nucleic acid comprises an AAV transfer cassette. In some embodiments, a nucleic acid comprises a transgene, wherein the transgene encodes the amino acid sequence of SEQ ID NO: 1. In some embodiments, a nucleic acid comprises a transgene, wherein the transgene encodes the amino acid sequence of SEQ ID NO: 20. In some embodiments, a nucleic acid comprises, from 5' to 3', a 5' inverted terminal repeat (ITR); a promoter; a transgene; a polyadenylation signal; and a 3' ITR; wherein the transgene encodes the amino acid sequence of SEQ ID NO: 1 or SEQ ID NO:20. In some embodiments, a nucleic acid comprises, from 5' to 3', a 5' inverted terminal repeat (ITR); a promoter; an intronic sequence; a transgene; a polyadenylation signal; and a 3' ITR; wherein the transgene encodes the amino acid sequence of SEQ ID NO: 1 or SEQ ID NO:20. In some embodiments, a nucleic acid comprises, from 5' to 3', a 5' inverted terminal repeat (ITR); a chicken beta-actin promoter; an intronic sequence; a transgene; a polyadenylation signal; and a 3' ITR; wherein the transgene encodes the amino acid sequence of SEQ ID NO: 1 or SEQ ID NO:20.

The AAV transfer cassettes described herein may be incorporated into a plasmid or a bacmid using standard molecular biology techniques. The plasmid or bacmid may further comprise one or more genetic elements used during production of AAV, including, for example, AAV rep and cap genes, and helper virus protein sequences.

AAV Production Methods

The AAV transfer cassettes, and nucleic acids (e.g., plasmids) comprising the AAV transfer cassettes described herein may be used to produce recombinant AAV vectors.

In some embodiments, a method for producing a recombinant AAV vector comprises contacting an AAV producer cell (e.g., an HEK293 cell) with an AAV transfer cassette or nucleic acid (e.g., plasmid) of the disclosure. In some embodiments, the method further comprises contacting the AAV producer cell with one or more additional plasmids encoding, for example, AAV rep and cap genes, and helper virus protein sequences.

In some embodiments, a method for producing a recombinant AAV vector comprises contacting an AAV producer cell (e.g., an insect cell such as a Sf9 cell) with at least one insect cell-compatible nucleic acid comprising an AAV transfer cassette of the disclosure. An "insect cell-compatible" nucleic acid is any nucleic acid which may be transformed or transfected into an insect cell, and which may be recognized by the transcription and/or translation machinery of the cell. In some embodiments, the insect cell-compatible nucleic acid is a baculoviral nucleic acid. In some embodiments, the method further comprises maintaining the insect cell under conditions such that AAV is produced.

The recombinant AAV vectors produced may be of any serotype, for example AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV. In some embodiments, the recombinant AAV vectors produced may comprise a protein capsid comprising a capsid protein subunit, wherein the capsid protein subunit comprises one or more amino acid modifications (e.g., substitutions and/or deletions) compared to the native AAV capsid protein subunit. For example, the recombinant AAV vectors may be modified AAV vectors derived from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV.

The recombinant AAV vectors may be used to transduce target cells with the transgene, for example by contacting the recombinant AAV vector with a target cell.

Compositions

Also provided are compositions comprising an AAV transfer cassette, a plasmid, a cell, or a recombinant AAV vector of the disclosure. In some embodiments, the compositions may further comprise a pharmaceutically acceptable carrier or excipient.

Methods of Treatment

The AAV vectors of the disclosure may be used to treat or prevent a disease, disorder, or other condition a subject in need thereof. The subject may be, for example a human or an animal. The human may be a pediatric subject, an adolescent subject, an adult subject, or a geriatric subject.

Thus, a further aspect of the disclosure is a method of administering the virus vector, virus particle and/or virus-like particle of the disclosure to a subject.

The present disclosure also provides a method of delivering a nucleic acid to a subject, comprising administering to the subject a virus vector and/or composition of this disclosure. Administration of the virus vectors, and/or compositions according to the present disclosure to a subject in need thereof can be by any means known in the art. Optionally, the virus vector and/or composition is delivered in an effective dose (e.g., a therapeutically effective dose) in a pharmaceutically acceptable carrier. In preferred embodiments, an effective amount of the virus vector and/or composition is delivered.

Dosages of the virus vector and/or virus-like particle to be administered to a subject depend upon the mode of administration, the disease or condition to be treated and/or prevented, the individual subject's condition, the particular virus vector or particle, and the nucleic acid to be delivered, and the like, and can be determined in a routine manner. In some embodiments, the dose of recombinant AAV is an effective dose. Exemplary effective doses may be, for example, a dose of at least about $10^5$, about $10^6$, about $10^7$, about $10^8$, about $10^9$, about $10^{10}$, about $10^{11}$, about $10^{12}$, about $10^{13}$, about $10^{14}$, about $10^{15}$ transducing units, optionally about $10^8$ to about $10^{13}$ transducing units. In some embodiments, an effective dose of recombinant AAV is a dose in the range of about $1\times10^{11}$ to about $1\times10^{15}$ vector genomes per kilogram body weight of the subject. For example, the effective dose may be about $1\times10^{11}$, about $5\times10^{11}$, about $1\times10^{12}$, about $5\times10^{12}$, about $1\times10^{13}$, about $5\times10^{13}$, about $1\times10^{14}$, about $5\times10^{14}$, or about $1\times10^{15}$ vector genomes per kilogram body weight of the subject.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a draining lymph node). The most suitable route in any given case will depend on the nature and severity of the condition being treated and/or prevented and on the nature of the particular AAV vector that is being used.

Delivery to a target tissue can also be achieved by delivering a depot comprising the virus vector and/or virus-like particle. As described herein, delivery of a "depot" refers to administration of a sustained-action formulation that allows slow release and/or gradual dissemination of the virus, so that the virus can act for longer periods than is possible with standard injections. In representative embodiments, a depot comprising the virus vector and/or virus-like particle is implanted into skeletal, cardiac and/or diaphragm muscle tissue or the tissue can be contacted with a film or other matrix comprising the virus vector and/or viral-like particle.

In some embodiments, a method for treating a subject in need thereof comprises administering to the subject an effective amount (e.g., a therapeutically effective amount) of an AAV transfer cassette, a plasmid, a cell, or a recombinant AAV of the disclosure. In some embodiments, the subject is a human subject. In some embodiments, the subject has NPC1.

EXAMPLES

The following examples, which are included herein for illustration purposes only, are not intended to be limiting.

Example 1: Preparation of a Recombinant AAV Vector in Mammalian Cells

Three plasmids are provided. The first plasmid comprises a transfer cassette comprising a transgene (SEQ ID NO: 2)

encoding NPC1 flanked by two ITRs (SEQ ID NO: 3 and 4). The first plasmid comprises the sequence of any one of SEQ ID NO: 14-19. The second plasmid comprises sequences encoding the Rep and Cap proteins. The third plasmid comprises various "helper" factors required for AAV production (E4, E2a, and VA).

The three plasmids are transfected into viral production cells (e.g., HEK293) using an appropriate transfection reagent (e.g., Lipofectamine™). After incubation at 37° C. for a predetermined period of time, AAV particles are collected from the media or the cells are lysed to release the AAV particles. The AAV particles are then purified and titered using either quantitative PCR (qPCR) or droplet digital PCR (ddPCR) according to standard methods. The AAV particles may be stored at −80° C. for later use.

Example 2: Preparation of a Recombinant AAV Vector in Insect Cells

A first recombinant baculoviral vector is provided. The first recombinant baculoviral vector comprises a nucleic acid comprising a transfer cassette comprising a transgene (SEQ ID NO: 2) encoding NPC1, wherein the transgene is flanked by two ITRs (SEQ ID NO: 3 and 4). The transfer cassette comprises the sequence of any one of SEQ ID NO: 14-19.

Insect cells (e.g., Sf9) are co-infected in suspension culture with the first recombinant baculoviral vector and a least one additional recombinant baculoviral vector comprising a nucleic acid encoding the AAV Rep and Cap proteins. After incubation at 28° C. for a predetermined period of time, AAV particles are collected from the media or the cells are lysed to release the AAV particles. The AAV particles are then purified and titered using either quantitative PCR (qPCR) or droplet digital PCR (ddPCR) according to standard methods. The AAV particles may be stored at −80° C. for later use.

Example 3: In Vitro Potency Assay

To determine whether the AAV transfer cassettes described herein are able to rescue the NPC1 lysosomal phenotype in cultured cells, a recombinant AAV2 vector packaging a hNPC1 transfer cassette (SEQ ID NO: 14) was prepared in HEK293 cells using a triple-transfection protocol (See, e.g., Example 1). The AAV2-hNPC1 vector was then used to transduce wildtype U2OS cells (osteosarcoma), and U2OS cells which do not express NPC1 (NPC$^{-/-}$) in vitro at a multiplicity of infection (MOI) of either $5\times10^3$ (5K) or $10\times10^3$ (10K). Cells were then incubated at 37° C. in a 5% $CO_2$ atmosphere.

NPC1 cells exhibit a characteristic accumulation of cholesterol in lysosomes, which can be monitored by observing the size and number of lysosomes in a cell. In this assay, lysosomal phenotype was monitored by measuring accumulation of a fluorescent organelle dye, LysoTracker® (ThermoFisher Scientific®), in the cells. 72 hours after transduction with the AAV2-hNPC1 vector, 50 mM of LysoTracker® was added to the cells. After 2 hours, the cells were fixed and LysoTracker® fluorescence was measured.

Figure 1A:
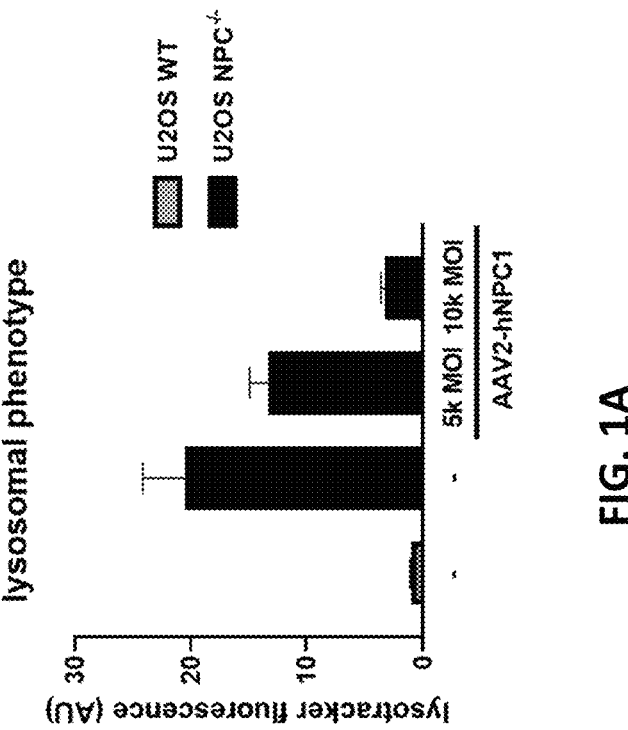
FIG. 1A is a graph that shows lysosomal phenotype, as determined by measuring LysoTracker® accumulation, in wildtype U2OS cells, NPC1-deficient (NPC1$^{-/-}$) U2OS cells, and NPC1$^{-/-}$ cells transduced with AAV2-hNPC at a Multiplicity of Infection (MOI) of either $5 \times 10^3$ or $10 \times 10^3$. Statistical significance determined using one-way ANOVA. Error bars represent standard error of the mean (SEM).

Results are shown in FIG. 1A. As expected, wildtype U2OS cells did not show significant accumulation of LysoTracker® fluorescence in lysosomes, whereas the NPC1$^{-/-}$ cells did. Cells transduced with AAV2-hNPC1 at a MOI of either 5K or 10K had significantly reduced accumulation of LysoTracker® fluorescence in lysosomes.

In a separate assay, cells transduced with hNPC1 were fixed and stained using filipin, a histochemical stain for cholesterol. The filipin stain, derived from *Streptomyces filipinensis*, was purchased from Polysciences, and was used at a final concentration of 50 µg/mL. The cells were visualized using a Pico Automated Cell Imaging System (ImageXpress®), and filipin stain was quantified. Results are shown in FIG. 1B. As expected, wildtype U2OS cells did not show significant cholesterol accumulation, whereas the NPC1$^{-/-}$ cells did. Cells transduced with AAV2-hNPC1 at a MOI of either 5K or 10K had significantly reduced cholesterol accumulation.

Taken together, these data show that transduction of cells using AAV2-hNPC successfully rescued lysosomal phenotype in NPC1-deficient U2OS cells.

Example 4: In Vivo Potency Assay

Figure 2:
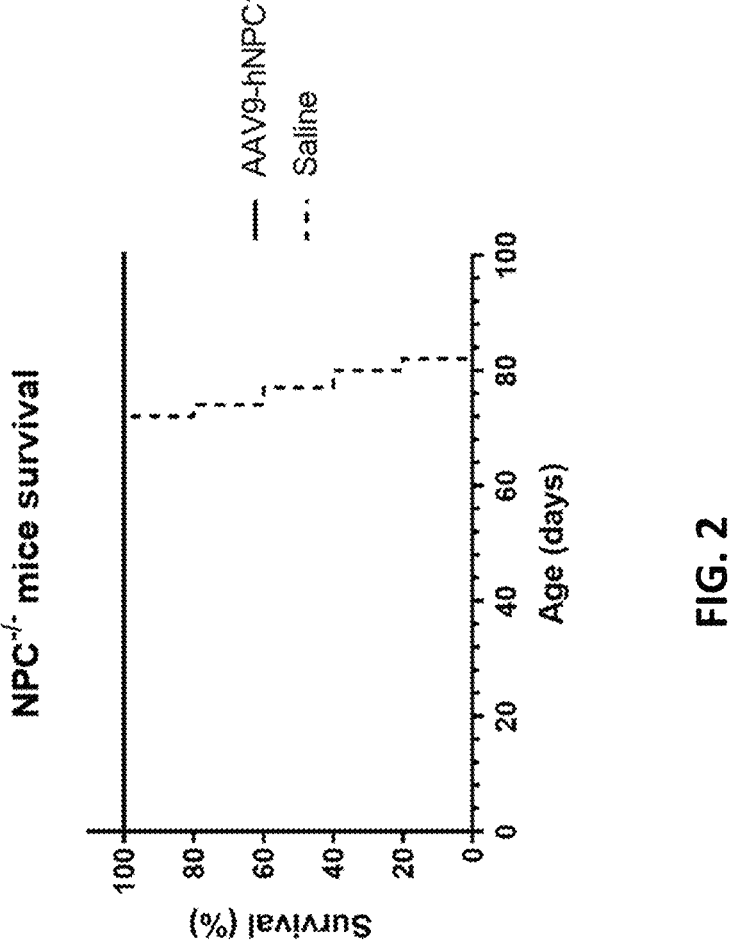
FIG. 2 is a Kaplan-Meier survival curve, showing survival of NPC1$^{-/-}$ mice after retro-orbital injection with saline or with AAV9-hNPC1. All AAV9-hNPC1-injected animals survived through the duration of the experiment, and were sacrificed around 100 days of age for histological analysis.

To determine whether the AAV transfer cassettes described herein are able to rescue the NPC1 phenotype in vivo, a recombinant AAV9 vector packaging a hNPC1 transfer cassette (SEQ ID NO: 14) was prepared in HEK293 cells using a triple-transfection protocol (See, e.g., Example 1). Mice deficient for NPC1 (i.e., NPC1$^{-/-}$ mice) were injected intravenously at a dose of $3.0\times10^{14}$ vector genomes per kilogram (vg/kg), by retro-orbital injection, with either saline or with the AAV9-hNPC1 vector around the age of 24-28 days. Results are shown in FIG. 2. All saline-treated mice died by the age of about 80 days. However, all AAV9-hNPC1-injected animals survived through the duration of experiment. The AAV9-hNPC1-injected mice were sacrificed around 100 days of age for analysis.

Figure 4:
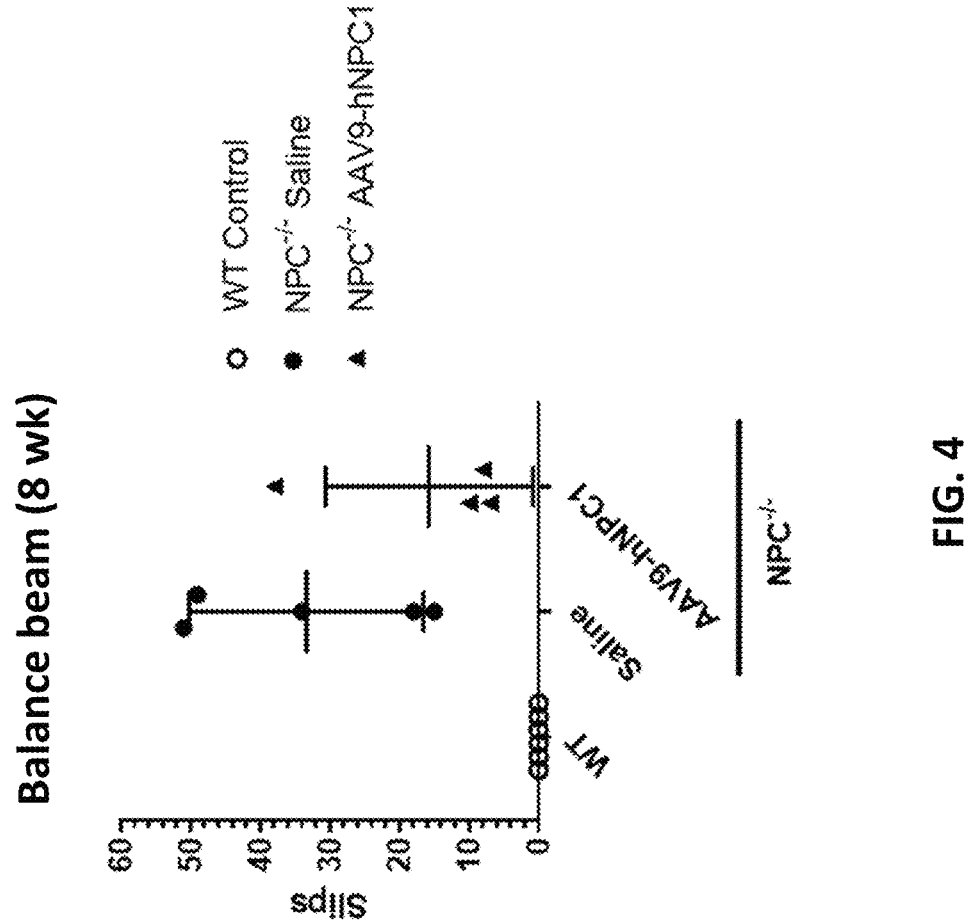
FIG. 4 shows number of slips in a balance beam walking test at about 8 weeks (56 days) of age in wildtype mice, saline-treated NPC1$^{-/-}$ mice, or NPC1$^{-/-}$ mice treated with AAV9-hNPC1. Error bars represent standard deviation.

Mice were also challenged in a balance beam walking test, wherein number of slips were measured as mice walked across a balance beam. The test was performed at about 8 weeks (56 days) of age. As shown in FIG. 4, wildtype mice did not slip off the balance beam. Although there was no statistically significant difference in the number of slips between NPC1$^{-/-}$ mice treated with AAV9-hNPC1 and saline-treated NPC1$^{-/-}$ mice, the average number of slips observed in the AAV9-hNPC1 group was less.

Figure 3:
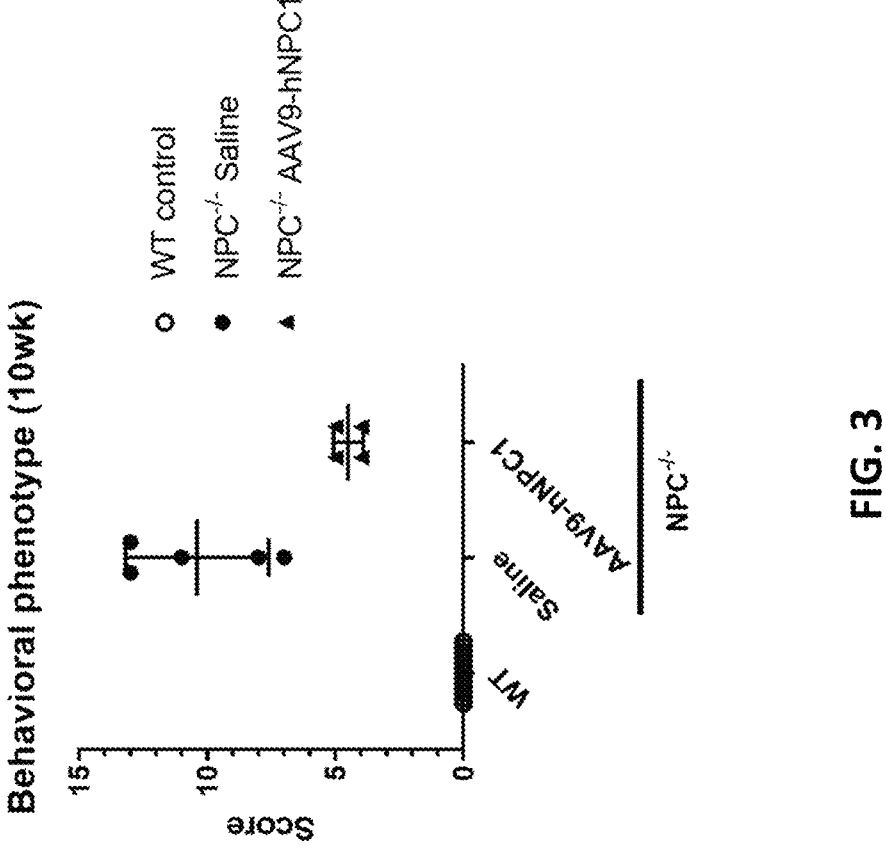
FIG. 3 shows behavioral phenotype score at about 10 weeks (70 days) of age in wildtype mice, saline-treated NPC1$^{-/-}$ mice, or NPC1$^{-/-}$ mice injected with AAV9-hNPC1. Statistical significance was determined using an unpaired T-test, and error bars represent SEM.

Behavioral phenotype score of the mice was also assessed at about 10 weeks (70 days) of age. The behavioral phenotype score is a composite score measuring various disease symptoms, including grooming, gait, kyphosis, ledge test, hindlimb clasp, and tremor. (See Alam et al, Sci Transl Med, 2016; Guyenet et al, J Vis Exp, 2010). As shown in FIG. 3, NPC1$^{-/-}$ mice treated with AAV9-hNPC1 had a significantly reduced score as compared to saline-treated NPC1$^{-/-}$ mice.

Taken together, these data demonstrate that AAV9-hNPC1 can at least partially rescue the disease phenotype of NPC1 deficient mice.

The foregoing is illustrative of the present invention, and is not to be construed as limiting thereof. The invention is defined by the following claims, with equivalents of the claims to be included therein.

NUMBERED EMBODIMENTS

Notwithstanding the appended claims, the following numbered embodiments also form part of the instant disclosure.

1. An Adeno-Associated Virus (AAV) transfer cassette comprising, from 5' to 3': a 5' inverted terminal repeat (ITR); a promoter; a transgene; a polyadenylation signal; and a 3' ITR; wherein the transgene encodes the NPC1 protein.

2. The AAV transfer cassette of embodiment 1, wherein at least one of the 5' ITR and the 3' ITR is about 110 to about 160 nucleotides in length.

3. The AAV transfer cassette of embodiment 1 or 2, wherein the 5' ITR is the same length as the 3' ITR.

4. The AAV transfer cassette of embodiment 1 or 2, wherein the 5' ITR and the 3' ITR have different lengths.

5. The AAV transfer cassette of any one of embodiments 1-4, wherein at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

6. The AAV transfer cassette of embodiment 1, wherein the 5' ITR comprises the sequence of SEQ ID NO: 3.

7. The AAV transfer cassette of embodiment 1, wherein the 3' ITR comprises the sequence of SEQ ID NO: 4.

8. The AAV transfer cassette of any one of embodiments 1-7, wherein the promoter is a constitutive promoter.

9. The AAV transfer cassette of any one of embodiments 1-7, wherein the promoter is an inducible promoter.

10. The AAV transfer cassette of any one of embodiments 1-9, wherein the promoter is a tissue-specific promoter.

11. The AAV transfer cassette of any one of embodiments 1-7, wherein the promoter is selected from the group consisting of the CBA promoter, the GUSB240 promoter, the GUSB379 promoter, the HSVTK promoter, the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the EF-1 alpha promoter, the dihydrofolate reductase (DHFR) promoter, and the phosphoglycerol kinase (PGK) promoter.

12. The AAV transfer cassette of embodiment 11, wherein the promoter is selected from the group consisting of the CBA promoter, the GUSB240 promoter, the GUSB379 promoter, and the HSVTK promoter.

13. The AAV transfer cassette of any one of embodiments 1-7, wherein the promoter comprises a sequence at least 95% or 100% identical to any one of SEQ ID NO: 5, SEQ ID NO: 6, SEQ ID NO: 7, or SEQ ID NO: 8.

14. The AAV transfer cassette of any one of embodiments 1-13, wherein the NPC1 protein is the human NPC1 protein.

15. The AAV transfer cassette of any one of embodiments 1-13, wherein the NPC1 protein has a sequence that is at least 90% identical to the sequence of the human NPC1 protein.

16. The AAV transfer cassette of embodiment 15, wherein the NPC1 protein has a sequence that is at least 95% identical to the sequence of the human NPC1 protein.

17. The AAV transfer cassette of embodiment 16, wherein the NPC1 protein has a sequence that is at least 98% identical to the sequence of the human NPC1 protein.

18. The AAV transfer cassette of any one of embodiments 1-13, wherein the NPC1 protein comprises the sequence of SEQ ID NO: 1.

19. The AAV transfer cassette of any one of embodiments 1-13, wherein the transgene comprises the sequence of SEQ ID NO: 2.

20. The AAV transfer cassette of any one of embodiments 1-18, wherein the polyadenylation signal is selected from simian virus 40 (SV40), rBG, α-globin, β-globin, human collagen, human growth hormone (hGH), polyoma virus, human growth hormone (hGH) and bovine growth hormone (bGH).

21. The AAV transfer cassette of embodiment 20, wherein the polyadenylation signal is the SV40 polyadenylation signal.

22. The AAV transfer cassette of embodiment 20, wherein the polyadenylation signal is the rBG polyadenylation signal.

23. The AAV transfer cassette of any one of embodiments 1-19, wherein the polyadenylation signal comprises the sequence at least 95% or 100% identical to SEQ ID NO: 12 or to SEQ ID NO: 13.

24. The AAV transfer cassette of any one of embodiments 1-23, wherein the cassette further comprises an enhancer.

25. The AAV transfer cassette of embodiment 24, wherein the enhancer is the CMV enhancer.

26. The AAV transfer cassette of embodiment 24, wherein the enhancer comprises the sequence of SEQ ID NO: 9, or a sequence at least 95% identical thereto. 27. The AAV transfer cassette of any one of embodiments 1-26, wherein the cassette further comprises an intronic sequence.

28. The AAV transfer cassette of embodiment 27, wherein the intronic sequence is a chimeric sequence.

29. The AAV transfer cassette of embodiment 27, wherein the intronic sequence is a hybrid sequence.

30. The AAV transfer cassette of embodiment 27, wherein the intronic sequence comprises sequences isolated or derived from SV40.

31. The AAV transfer cassette of embodiment 27, wherein the intronic sequence comprises the sequence of any one of SEQ ID NO: 10-11.

32. The AAV transfer cassette of embodiment 1, wherein the AAV transfer cassette comprises the sequence of any one of SEQ ID NO: 14-19.

33. A plasmid comprising the AAV transfer cassette of any one of embodiments 1-31.

34. A cell comprising the AAV transfer cassette of any one of embodiments 1-32 or the plasmid of embodiment 33.

35. A recombinant AAV vector comprising a protein capsid and a nucleic acid encapsidated by the protein capsid: wherein the nucleic acid comprises a transfer cassette comprising, from 5' to 3': a 5' inverted terminal repeat (ITR); a promoter; a transgene; a polyadenylation signal; and a 3' ITR; wherein the transgene encodes the NPC1 protein.

36. The recombinant AAV vector of embodiment 35, wherein at least one of the 5' ITR and the 3' ITR is about 110 to about 160 nucleotides in length.

37. The recombinant AAV vector of embodiment 36 or 36, wherein the 5' ITR is the same length as the 3' ITR.

38. The recombinant AAV vector of embodiment 35 or 36, wherein the 5' ITR and the 3' ITR have different lengths.

39. The recombinant AAV vector of any one of embodiments 35-38, wherein at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

40. The recombinant AAV vector of embodiment 35, wherein the 5' ITR comprises the sequence of SEQ ID NO: 3.

41. The recombinant AAV vector of embodiment 35, wherein the 3' ITR comprises the sequence of SEQ ID NO: 4.

42. The recombinant AAV vector of any one of embodiments 35-41, wherein the promoter is a constitutive promoter.

43. The recombinant AAV vector of any one of embodiments 35-41, wherein the promoter is an inducible promoter.

44. The recombinant AAV vector of any one of embodiments 35-41, wherein the promoter is a tissue-specific promoter.

45. The recombinant AAV vector of any one of embodiments 35-41, wherein the promoter is selected from the group consisting of the CBA promoter, the GUSB240 promoter, the GUSB379 promoter, the HSVTK promoter, the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the EF-1 alpha promoter, the dihydrofolate reductase (DHFR) promoter, and the phosphoglycerol kinase (PGK) promoter.

46. The recombinant AAV vector of embodiment 45, wherein the promoter is selected from the group consisting of the CBA promoter, the GUSB240 promoter, the GUSB379 promoter, and the HSVTK promoter.

47. The recombinant AAV vector of any one of embodiments 35-41, wherein the promoter comprises a sequence at least 95% or 100% identical to any one of SEQ ID NO: 5, SEQ ID NO: 6, SEQ ID NO: 7, or SEQ ID NO: 8.

48. The recombinant AAV vector of any one of embodiments 35-47, wherein the NPC1 protein is the human NPC1 protein.

49. The recombinant AAV vector of any one of embodiments 35-48, wherein the NPC1 protein has a sequence that is at least 90% identical to the sequence of the human NPC1 protein.

50. The recombinant AAV vector of embodiment 49, wherein the NPC1 protein has a sequence that is at least 95% identical to the sequence of the human NPC1 protein.

51. The recombinant AAV vector of embodiment 50, wherein the NPC1 protein has a sequence that is at least 98% identical to the sequence of the human NPC1 protein.

52. The recombinant AAV vector of any one of embodiments 35-48, wherein the NPC1 protein comprises the sequence of SEQ ID NO: 1.

53. The recombinant AAV vector of any one of embodiments 35-48, wherein the transgene comprises the sequence of SEQ ID NO: 2.

54. The recombinant AAV vector of any one of embodiments 35-53, wherein the polyadenylation signal is selected from simian virus 40 (SV40), rBG, α-globin, β-globin, human collagen, human growth hormone (hGH), polyoma virus, human growth hormone (hGH) and bovine growth hormone (bGH).

55. The recombinant AAV vector of embodiment 54, wherein the polyadenylation signal is the SV40 polyadenylation signal.

56. The recombinant AAV vector of embodiment 54, wherein the polyadenylation signal is the rBG polyadenylation signal.

57. The recombinant AAV vector of any one of embodiments 35-53, wherein the polyadenylation signal comprises the sequence at least 95% or 100% identical to SEQ ID NO: 12 or to SEQ ID NO: 13.

58. The recombinant AAV vector of any one of embodiments 35-57, wherein the cassette further comprises an enhancer.

59. The recombinant AAV vector of embodiment 58, wherein the enhancer is the CMV enhancer.

60. The recombinant AAV vector of embodiment 58, wherein the enhancer comprises the sequence of SEQ ID NO: 9, or a sequence at least 95% identical thereto.

61. The recombinant AAV vector of any one of embodiments 35-60, wherein the cassette further comprises an intronic sequence.

62. The recombinant AAV vector of embodiment 61, wherein the intronic sequence is a chimeric sequence.

63. The recombinant AAV vector of embodiment 61, wherein the intronic sequence is a hybrid sequence.

64. The recombinant AAV vector of embodiment 61, wherein the intronic sequence comprises sequences isolated or derived from SV40.

65. The recombinant AAV vector of embodiment 61, wherein the intronic sequence comprises the sequence of any one of SEQ ID NO: 10-11.

66. The recombinant AAV vector of embodiment 35, wherein the AAV transfer cassette comprises the sequence of any one of SEQ ID NO: 14-19.

67. The recombinant AAV vector of embodiment 35, wherein the AAV transfer cassette comprises the sequence of SEQ ID NO: 14.

68. The recombinant AAV vector of any one of embodiments 35-67, wherein the protein capsid comprises a capsid protein subunit from an AAV of any one of the following serotypes: AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

69. The recombinant AAV vector of any one of embodiments 35-67, wherein the protein capsid comprises a capsid protein subunit that has one or more amino acid mutations relative to a capsid protein subunit of any one of the following AAV serotypes: AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

70. A method of producing a recombinant AAV vector, the method comprising contacting an AAV producer cell with the AAV transfer cassette of any one of embodiments 1-32 or the plasmid of embodiment 33.

71. A recombinant AAV vector produced by the method of embodiment 35.

72. The recombinant AAV vector of embodiment 71, wherein the vector is of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV.

73. A composition comprising the AAV transfer cassette of any one of embodiments 1-32, the plasmid of embodiment 33, the cell of embodiment 34, or the recombinant AAV vector of any one of embodiments 35-69, 71, or 72.

74. A method for treating a subject in need thereof comprising administering to the subject an effective amount of the AAV transfer cassette of any one of embodiments 1-32, the plasmid of embodiment 33, the cell of embodiment 34, or the recombinant AAV vector of any one of embodiments 35-68, 70 or 71.

75. The method of embodiment 74, wherein the subject has NPC1.

76. The method of embodiment 74 or 75, wherein the subject is a human subject.

77. A nucleic acid encoding comprising, from 5' to 3', a 5' inverted terminal repeat (ITR); a promoter; a transgene; a polyadenylation signal; and a 3' ITR; wherein the transgene encodes the amino acid sequence of SEQ ID NO: 1 or SEQ ID NO:20.

78. An Adeno-Associated Virus (AAV) transfer cassette comprising, from 5' to 3': a 5' inverted terminal repeat (ITR); a chicken beta-actin promoter; a transgene; a polyadenylation signal; and a 3' ITR; wherein the transfer cassette comprises an intronic sequence; wherein the transgene encodes the NPC1 protein.

79. The AAV transfer cassette of embodiment 78, wherein the intronic sequence is located between the promoter and the transgene.

80. The AAV transfer cassette of embodiment 78 or 79, wherein the 5' ITR comprises the sequence of SEQ ID NO: 3.

81. The AAV transfer cassette of any one of embodiments 78-80, wherein the 3' ITR comprises the sequence of SEQ ID NO: 4.

82. The AAV transfer cassette of any one of embodiments 78-81, wherein the promoter comprises the sequence of SEQ ID NO: 5.

83. The AAV transfer cassette of any one of embodiments 78-82, wherein the intronic sequence is an SV40 intron.

84. The AAV transfer cassette of any one of embodiments 78-82, wherein the intronic sequence comprises the sequence of SEQ ID NO: 10.

85. The AAV transfer cassette of any one of embodiments 78-84, wherein the NPC1 protein is the human NPC1 protein.

86. The AAV transfer cassette of any one of embodiments 78-84, wherein the NPC1 protein comprises the sequence of SEQ ID NO: 1.

87. The AAV transfer cassette of any one of embodiments 78-84, wherein the transgene comprises the sequence of SEQ ID NO: 2.

88. The AAV transfer cassette of any one of embodiments 78-87, wherein the polyadenylation signal is the SV40 polyadenylation signal.

89. The AAV transfer cassette of any one of embodiments 78-87, wherein the polyadenylation signal comprises the sequence of SEQ ID NO: 12.

90. The AAV transfer cassette of any one of embodiments 78-89, wherein the cassette comprises an enhancer.

91. The AAV transfer cassette of embodiment 78, wherein the AAV transfer cassette comprises the sequence of SEQ ID NO: 14

92. The AAV transfer cassette of embodiment 78, wherein the AAV transfer cassette comprises the sequence of any one of SEQ ID NO: 15-19.

93. A plasmid comprising the AAV transfer cassette of any one of embodiments 78-92.

94. A nucleic acid comprising, from 5' to 3', a 5' inverted terminal repeat (ITR); a promoter; a transgene; a polyadenylation signal; and a 3' ITR; wherein the nucleic acid comprises an intronic sequence; wherein the transgene encodes the amino acid sequence of SEQ ID NO: 1.

95. The nucleic acid of embodiment 94, wherein the intronic sequence is located between the promoter and the transgene.

96. A cell comprising the AAV transfer cassette of any one of embodiments 78-92, the plasmid of embodiment 93, or the nucleic acid of embodiment 94 or 95.

97. A recombinant AAV vector comprising a protein capsid and a nucleic acid encapsidated by the protein capsid: wherein the nucleic acid comprises the AAV transfer cassette of any one of embodiments 78-92.

98. The recombinant AAV vector of embodiment 97, wherein the protein capsid comprises a capsid protein subunit from an AAV of any one of the following serotypes: AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

99. The recombinant AAV vector of embodiment 97, wherein the protein capsid comprises a capsid protein subunit that has one or more amino acid mutations relative to a capsid protein subunit of any one of the following AAV serotypes: AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

100. A method of producing a recombinant AAV vector, the method comprising contacting an AAV producer cell with the AAV transfer cassette of any one of embodiments 78-92, the plasmid of embodiment 93, or the nucleic acid of embodiment 93.

101. A recombinant AAV vector produced by the method of embodiment 100.

102. A composition comprising the AAV transfer cassette of any one of embodiments 78-92, the plasmid of embodiment 93, the nucleic acid of embodiment 94 or 95, the cell of embodiment 96, or the recombinant AAV vector of any one of embodiments 97-99 or 101.

103. A method for treating a subject in need thereof comprising administering to the subject an effective amount of the AAV transfer cassette of any one of embodiments 78-92, the plasmid of embodiment 93, the nucleic acid of embodiment 94 or 95, the cell of embodiment 96, or the recombinant AAV vector of any one of embodiments 97-99 or 101.

104. The method of embodiment 103, wherein the subject has NPC1.

105. The method of embodiment 103 or 104, wherein the subject is a human subject.

---

What is claimed is:

1. A method for treating a subject having Neimann-Pick Disease Type C1 (NPCI) in need thereof, comprising:

systemically administering to the subject a recombinant AAV vector comprising a protein capsid and a nucleic acid encapsidated by the protein capsid, wherein the nucleic acid comprises a transfer cassette comprising the sequence of SEQ ID NO: 14 and the protein capsid comprises a capsid protein subunit from an AAV9 serotype, and wherein treatment reduces cholesterol accumulation in cells of the subject transduced by the recombinant AAV vector.

2. The method of claim 1, wherein the subject is a human subject.

3. A method for treating a subject having Neimann-Pick Disease Type C1 (NPCI) in need thereof, comprising:

systemically administering to the subject a recombinant AAV vector comprising a protein capsid and a nucleic acid encapsidated by the protein capsid, wherein the nucleic acid comprises a transfer cassette comprising the sequence of any one of SEQ ID NOS: 15-19 and the protein capsid comprises a capsid protein subunit from an AAV9 serotype, and wherein treatment reduces cholesterol accumulation in cells of the subject transduced by the recombinant AAV vector.

4. The method of claim 3, wherein the subject is a human subject.

\* \* \* \* \*

SEQUENCE LISTING

```
<160> NUMBER OF SEQ ID NOS: 20

<210> SEQ ID NO 1
<211> LENGTH: 1278
<212> TYPE: PRT
<213> ORGANISM: Homo sapiens

<400> SEQUENCE: 1

Met Thr Ala Arg Gly Leu Ala Leu Gly Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45
```

-continued

```
Lys Pro Leu Pro Lys Asp Gly Tyr Asp Leu Val Gln Glu Leu Cys Pro
    50              55              60

Gly Phe Phe Phe Gly Asn Val Ser Leu Cys Cys Asp Val Arg Gln Leu
65              70              75              80

Gln Thr Leu Lys Asp Asn Leu Gln Leu Pro Leu Gln Phe Leu Ser Arg
            85              90              95

Cys Pro Ser Cys Phe Tyr Asn Leu Leu Asn Leu Phe Cys Glu Leu Thr
            100             105             110

Cys Ser Pro Arg Gln Ser Gln Phe Leu Asn Val Thr Ala Thr Glu Asp
            115             120             125

Tyr Val Asp Pro Val Thr Asn Gln Thr Lys Thr Asn Val Lys Glu Leu
    130             135             140

Gln Tyr Tyr Val Gly Gln Ser Phe Ala Asn Ala Met Tyr Asn Ala Cys
145             150             155             160

Arg Asp Val Glu Ala Pro Ser Ser Asn Asp Lys Ala Leu Gly Leu Leu
            165             170             175

Cys Gly Lys Asp Ala Asp Ala Cys Asn Ala Thr Asn Trp Ile Glu Tyr
            180             185             190

Met Phe Asn Lys Asp Asn Gly Gln Ala Pro Phe Thr Ile Thr Pro Val
            195             200             205

Phe Ser Asp Phe Pro Val His Gly Met Glu Pro Met Asn Asn Ala Thr
    210             215             220

Lys Gly Cys Asp Glu Ser Val Asp Glu Val Thr Ala Pro Cys Ser Cys
225             230             235             240

Gln Asp Cys Ser Ile Val Cys Gly Pro Lys Pro Gln Pro Pro Pro
            245             250             255

Pro Ala Pro Trp Thr Ile Leu Gly Leu Asp Ala Met Tyr Val Ile Met
            260             265             270

Trp Ile Thr Tyr Met Ala Phe Leu Leu Val Phe Phe Gly Ala Phe Phe
            275             280             285

Ala Val Trp Cys Tyr Arg Lys Arg Tyr Phe Val Ser Glu Tyr Thr Pro
    290             295             300

Ile Asp Ser Asn Ile Ala Phe Ser Val Asn Ala Ser Asp Lys Gly Glu
305             310             315             320

Ala Ser Cys Cys Asp Pro Val Ser Ala Ala Phe Glu Gly Cys Leu Arg
            325             330             335

Arg Leu Phe Thr Arg Trp Gly Ser Phe Cys Val Arg Asn Pro Gly Cys
            340             345             350

Val Ile Phe Phe Ser Leu Val Phe Ile Thr Ala Cys Ser Ser Gly Leu
            355             360             365

Val Phe Val Arg Val Thr Thr Asn Pro Val Asp Leu Trp Ser Ala Pro
    370             375             380

Ser Ser Gln Ala Arg Leu Glu Lys Glu Tyr Phe Asp Gln His Phe Gly
385             390             395             400

Pro Phe Phe Arg Thr Glu Gln Leu Ile Ile Arg Ala Pro Leu Thr Asp
            405             410             415

Lys His Ile Tyr Gln Pro Tyr Pro Ser Gly Ala Asp Val Pro Phe Gly
            420             425             430

Pro Pro Leu Asp Ile Gln Ile Leu His Gln Val Leu Asp Leu Gln Ile
            435             440             445

Ala Ile Glu Asn Ile Thr Ala Ser Tyr Asp Asn Glu Thr Val Thr Leu
    450             455             460

Gln Asp Ile Cys Leu Ala Pro Leu Ser Pro Tyr Asn Thr Asn Cys Thr
```

-continued

```
465                    470                    475                    480

Ile Leu Ser Val Leu Asn Tyr Phe Gln Asn Ser His Ser Val Leu Asp
                485                    490                    495

His Lys Lys Gly Asp Asp Phe Phe Val Tyr Ala Asp Tyr His Thr His
                500                    505                    510

Phe Leu Tyr Cys Val Arg Ala Pro Ala Ser Leu Asn Asp Thr Ser Leu
            515                    520                    525

Leu His Asp Pro Cys Leu Gly Thr Phe Gly Gly Pro Val Phe Pro Trp
        530                    535                    540

Leu Val Leu Gly Gly Tyr Asp Asp Gln Asn Tyr Asn Asn Ala Thr Ala
545                    550                    555                    560

Leu Val Ile Thr Phe Pro Val Asn Asn Tyr Tyr Asn Asp Thr Glu Lys
                565                    570                    575

Leu Gln Arg Ala Gln Ala Trp Glu Lys Glu Phe Ile Asn Phe Val Lys
            580                    585                    590

Asn Tyr Lys Asn Pro Asn Leu Thr Ile Ser Phe Thr Ala Glu Arg Ser
            595                    600                    605

Ile Glu Asp Glu Leu Asn Arg Glu Ser Asp Ser Asp Val Phe Thr Val
        610                    615                    620

Val Ile Ser Tyr Ala Ile Met Phe Leu Tyr Ile Ser Leu Ala Leu Gly
625                    630                    635                    640

His Ile Lys Ser Cys Arg Arg Leu Leu Val Asp Ser Lys Val Ser Leu
                645                    650                    655

Gly Ile Ala Gly Ile Leu Ile Val Leu Ser Ser Val Ala Cys Ser Leu
            660                    665                    670

Gly Val Phe Ser Tyr Ile Gly Leu Pro Leu Thr Leu Ile Val Ile Glu
            675                    680                    685

Val Ile Pro Phe Leu Val Leu Ala Val Gly Val Asp Asn Ile Phe Ile
        690                    695                    700

Leu Val Gln Ala Tyr Gln Arg Asp Glu Arg Leu Gln Gly Glu Thr Leu
705                    710                    715                    720

Asp Gln Gln Leu Gly Arg Val Leu Gly Glu Val Ala Pro Ser Met Phe
                725                    730                    735

Leu Ser Ser Phe Ser Glu Thr Val Ala Phe Phe Leu Gly Ala Leu Ser
                740                    745                    750

Val Met Pro Ala Val His Thr Phe Ser Leu Phe Ala Gly Leu Ala Val
            755                    760                    765

Phe Ile Asp Phe Leu Leu Gln Ile Thr Cys Phe Val Ser Leu Leu Gly
        770                    775                    780

Leu Asp Ile Lys Arg Gln Glu Lys Asn Arg Leu Asp Ile Phe Cys Cys
785                    790                    795                    800

Val Arg Gly Ala Glu Asp Gly Thr Ser Val Gln Ala Ser Glu Ser Cys
                805                    810                    815

Leu Phe Arg Phe Phe Lys Asn Ser Tyr Ser Pro Leu Leu Leu Lys Asp
            820                    825                    830

Trp Met Arg Pro Ile Val Ile Ala Ile Phe Val Gly Val Leu Ser Phe
            835                    840                    845

Ser Ile Ala Val Leu Asn Lys Val Asp Ile Gly Leu Asp Gln Ser Leu
        850                    855                    860

Ser Met Pro Asp Asp Ser Tyr Met Val Asp Tyr Phe Lys Ser Ile Ser
865                    870                    875                    880

Gln Tyr Leu His Ala Gly Pro Pro Val Tyr Phe Val Leu Glu Glu Gly
                885                    890                    895
```

-continued

```
His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
            915                 920                 925

Leu Asp Asn Tyr Thr Arg Ile Gly Phe Ala Pro Ser Ser Trp Ile Asp
            930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
            980                 985                 990

Gly Asp Phe Met Arg Phe Leu Pro  Met Phe Leu Ser Asp  Asn Pro Asn
            995                 1000                1005

Pro Lys  Cys Gly Lys Gly Gly  His Ala Ala Tyr Ser  Ser Ala Val
    1010                1015                1020

Asn Ile  Leu Leu Gly His Gly  Thr Arg Val Gly Ala  Thr Tyr Phe
    1025                1030                1035

Met Thr  Tyr His Thr Val Leu  Gln Thr Ser Ala Asp  Phe Ile Asp
    1040                1045                1050

Ala Leu  Lys Lys Ala Arg Leu  Ile Ala Ser Asn Val  Thr Glu Thr
    1055                1060                1065

Met Gly  Ile Asn Gly Ser Ala  Tyr Arg Val Phe Pro  Tyr Ser Val
    1070                1075                1080

Phe Tyr  Val Phe Tyr Glu Gln  Tyr Leu Thr Ile Ile  Asp Asp Thr
    1085                1090                1095

Ile Phe  Asn Leu Gly Val Ser  Leu Gly Ala Ile Phe  Leu Val Thr
    1100                1105                1110

Met Val  Leu Leu Gly Cys Glu  Leu Trp Ser Ala Val  Ile Met Cys
    1115                1120                1125

Ala Thr  Ile Ala Met Val Leu  Val Asn Met Phe Gly  Val Met Trp
    1130                1135                1140

Leu Trp  Gly Ile Ser Leu Asn  Ala Val Ser Leu Val  Asn Leu Val
    1145                1150                1155

Met Ser  Cys Gly Ile Ser Val  Glu Phe Cys Ser His  Ile Thr Arg
    1160                1165                1170

Ala Phe  Thr Val Ser Met Lys  Gly Ser Arg Val Glu  Arg Ala Glu
    1175                1180                1185

Glu Ala  Leu Ala His Met Gly  Ser Ser Val Phe Ser  Gly Ile Thr
    1190                1195                1200

Leu Thr  Lys Phe Gly Gly Ile  Val Val Leu Ala Phe  Ala Lys Ser
    1205                1210                1215

Gln Ile  Phe Gln Ile Phe Tyr  Phe Arg Met Tyr Leu  Ala Met Val
    1220                1225                1230

Leu Leu  Gly Ala Thr His Gly  Leu Ile Phe Leu Pro  Val Leu Leu
    1235                1240                1245

Ser Tyr  Ile Gly Pro Ser Val  Asn Lys Ala Lys Ser  Cys Ala Thr
    1250                1255                1260

Glu Glu  Arg Tyr Lys Gly Thr  Glu Arg Glu Arg Leu  Leu Asn Phe
    1265                1270                1275
```

<210> SEQ ID NO 2
<211> LENGTH: 3834

-continued

<212> TYPE: DNA
<213> ORGANISM: Artificial Sequence
<220> FEATURE:
<223> OTHER INFORMATION: NPC1 cDNA

<400> SEQUENCE: 2

```
atgaccgctc gcggcctggc ccttggcctc ctcctgctgc tactgtgtcc agcgcaggtg       60
ttttcacagt cctgtgtttg gtatggagag tgtggaattg catatgggga caagaggtac      120
aattgcgaat attctggccc accaaaacca ttgccaaagg atggatatga cttagtgcag      180
gaactctgtc caggattctt ctttggcaat gtcagtctct gttgtgatgt tcggcagctt      240
cagacactaa aagacaacct gcagctgcct ctacagtttc tgtccagatg tccatcctgt      300
ttttataacc tactgaacct gttttgtgag ctgacatgta gccctcgaca gagtcagttt      360
ttgaatgtta cagctactga agattatgtt gatcctgtta caaaccagac gaaaacaaat      420
gtgaaagagt tacaatacta cgtcggacag agttttgcca atgcaatgta caatgcctgc      480
cgggatgtgg aggcccctc aagtaatgac aaggccctgg gactcctgtg tgggaaggac      540
gctgacgcct gtaatgccac caactggatt gaatacatgt tcaataagga caatggacag      600 gcaccttta ccatcactcc tgtgtttca gattttccag tccatgggat ggagcccatg      660
aacaatgcca ccaaaggctg tgacgagtct gtggatgagg tcacagcacc atgtagctgc      720
caagactgct ctattgtctg tggccccaag ccccagcccc cacctcctcc tgctccctgg      780
acgatccttg gcttggacgc catgtatgtc atcatgtgga tcacctacat ggcgttttg      840 cttgtgtttt ttggagcatt ttttgcagtg tggtgctaca aaaacggta ttttgtctcc      900 gagtacactc ccatcgatag caatatagct ttttctgtta atgcaagtga caaaggagag      960
gcgtcctgct gtgaccctgt cagcgcagca tttgagggct gcttgaggcg gctgttcaca     1020
cgctgggggt ctttctgcgt ccgaaaccct ggctgtgtca ttttcttctc gctggtcttc     1080
attactgcgt gttcgtcagg cctggtgttt gtccgggtca caaccaatcc agttgacctc     1140
tggtcagccc ccagcagcca ggctcgcctg gaaaaagagt actttgacca gcactttggg     1200
cctttcttcc ggacggagca gctcatcatc cgggcccctc tcactgacaa acacatttac     1260
cagccatacc cttcgggagc tgatgtaccc tttggacctc cgcttgacat acagatactg     1320
caccaggttc ttgacttaca aatagccatc gaaaacatta ctgcctctta tgacaatgag     1380
actgtgacac ttcaagacat ctgcttggcc cctctttcac cgtataacac gaactgcacc     1440
attttgagtg tgttaaatta cttccagaac agccattccg tgctggacca caagaaaggg     1500
gacgacttct ttgtgtatgc cgattaccac acgcactttc tgtactgcgt acgggctcct     1560
gcctctctga atgatacaag tttgctccat gacccttgtc tgggtacgtt tggtggacca     1620
gtgttcccgt ggcttgtgtt gggaggctat gatgatcaaa actacaataa cgccactgcc     1680
cttgtgatta ccttccctgt caataattac tataatgata cagagaagct ccagagggcc     1740
caggcctggg aaaaagagtt tattaatttt gtgaaaaact acaagaatcc caatctgacc     1800
atttccttca ctgctgaacg aagtattgaa gatgaactaa atcgtgaaag tgacagtgat     1860
gtcttcaccg ttgtaattag ctatgccatc atgtttctat atatttccct agccttgggg     1920
cacatcaaaa gctgtcgcag gcttctggtg gattcgaagg tctcactagg catcgcgggc     1980
atcttgatcg tgctgagctc ggtggcttgc tccttgggtg tcttcagcta cattgggttg     2040
cccttgaccc tcattgtgat tgaagtcatc ccgttcctgg tgctggctgt ggagtggac     2100 aacatcttca ttctggtgca ggcctaccag agagatgaac gtcttcaagg ggaaaccctg     2160
```

-continued

```
gatcagcagc tgggcagggt cctaggagaa gtggctccca gtatgttcct gtcatccttt      2220
tctgagactg tagcattttt cttaggagca ttgtccgtga tgccagccgt gcacaccttc      2280
tctctctttg cgggattggc agtcttcatt gactttcttc tgcagattac ctgtttcgtg      2340
agtctcttgg ggttagacat taaacgtcaa gagaaaaatc ggctagacat cttttgctgt      2400
gtcagaggtg ctgaagatgg aacaagcgtc caggcctcag agagctgttt gtttcgcttc      2460
ttcaaaaact cctattctcc acttctgcta aaggactgga tgagaccaat tgtgatagca      2520
atatttgtgg gtgttctgtc attcagcatc gcagtcctga acaaagtaga tattggattg      2580
gatcagtctc tttcgatgcc agatgactcc tacatggtgg attatttcaa atccatcagt      2640
cagtacctgc atgcgggtcc gcctgtgtac tttgtcctgg aggaagggca cgactacact      2700
tcttccaagg ggcagaacat ggtgtgcggc ggcatgggct gcaacaatga ttccctggtg      2760
cagcagatat ttaacgcggc gcagctggac aactataccc gaataggctt cgccccctcg      2820
tcctggatcg acgattattt cgactgggtg aagccacagt cgtcttgctg tcgagtggac      2880
aatatcactg accagttctg caatgcttca gtggttgacc ctgcctgcgt tcgctgcagg      2940
cctctgactc cggaaggcaa acagaggcct caggggggag acttcatgag attcctgccc      3000
atgttccttt cggataaccc taaccccaag tgtggcaaag ggggacatgc tgcctatagt      3060
tctgcagtta acatcctcct tggccatggc accagggtcg gagccacgta cttcatgacc      3120
taccacaccg tgctgcagac ctctgctgac tttattgacg ctctgaagaa agcccgactt      3180
atagccagta atgtcaccga aaccatgggc attaacggca gtgcctaccg agtatttcct      3240
tacagtgtgt tttatgtctt ctacgaacag tacctgacca tcattgacga cactatcttc      3300
aacctcggtg tgtccctggg cgcgatattt ctggtgacca tggtcctcct gggctgtgag      3360
ctctggtctg cagtcatcat gtgtgccacc atcgccatgg tcttggtcaa catgtttgga      3420
gttatgtggc tctggggcat cagtctgaac gctgtatcct tggtcaacct ggtgatgagc      3480
tgtggcatct ccgtggagtt ctgcagccac ataaccagag cgttcacggt gagcatgaaa      3540
ggcagccgcg tggagcgcgc ggaagaggca cttgcccaca tgggcagctc cgtgttcagt      3600
ggaatcacac ttacaaaatt tggagggatt gtggtgttgg cttttgccaa atctcaaatt      3660
ttccagatat tctacttcag gatgtatttg gccatggtct tactgggagc cactcacgga      3720
ttaatatttc tccctgtctt actcagttac ataggggcat cagtaaataa agccaaaagt      3780
tgtgccactg aagagcgata caaaggaaca gagcgcgaac ggcttctaaa tttc          3834
```

<210> SEQ ID NO 3
<211> LENGTH: 141
<212> TYPE: DNA
<213> ORGANISM: Artificial Sequence
<220> FEATURE:
<223> OTHER INFORMATION: 5 prime Inverted Terminal Repeat

<400> SEQUENCE: 3

```
cctgcaggca gctgcgcgct cgctcgctca ctgaggccgc ccgggcaaag cccgggcgtc         60
gggcgacctt tggtcgcccg gcctcagtga gcgagcgagc gcgcagagag ggagtggcca        120
actccatcac tagggttcc t                                                   141
```

<210> SEQ ID NO 4
<211> LENGTH: 141
<212> TYPE: DNA
<213> ORGANISM: Artificial Sequence
<220> FEATURE:
<223> OTHER INFORMATION: 3 prime Inverted Terminal Repeat -continued

<400> SEQUENCE: 4
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g                                               141

<210> SEQ ID NO 5
<211> LENGTH: 278
<212> TYPE: DNA
<213> ORGANISM: Gallus gallus

<400> SEQUENCE: 5
tcgaggtgag ccccacgttc tgcttcactc tccccatctc cccccctcc ccaccccaa      60 ttttgtattt atttattttt taattatttt gtgcagcgat ggggcggggg gggggggggg     120
ggcgcgcgcc aggcggggcg gggcggggcg aggggcgggg cggggcgagg cggagaggtg     180
cggcggcagc caatcagagc ggcgcgctcc gaaagtttcc ttttatggcg aggcggcggc     240
ggcggcggcc ctataaaaag cgaagcgcgc ggcgggcg                            278

<210> SEQ ID NO 6
<211> LENGTH: 240
<212> TYPE: DNA
<213> ORGANISM: Artificial Sequence
<220> FEATURE:
<223> OTHER INFORMATION: GUSB240 Promoter

<400> SEQUENCE: 6
cggctggggc tgagggtgag ggtcccgttt ccccaaaggc ctagcctggg gttccagcca      60
caagccctac cgggcagcgc ccggccccgc ccctccaggc ctggcactcg tcctcaacca     120
agatggcgcg gatggcttca ggcgcatcac gacaccggcg cgtcacgcga cccgccctac     180
gggcacctcc cgcgcttttc ttagcgccgc agacggtggc cgagcggggg accgggaagc     240

<210> SEQ ID NO 7
<211> LENGTH: 379
<212> TYPE: DNA
<213> ORGANISM: Artificial Sequence
<220> FEATURE:
<223> OTHER INFORMATION: GUSB379 Promoter

<400> SEQUENCE: 7
attcctgctg ggaaaagcaa gtggaggtgc tccttgaaga aacaggggga tcccaccgat      60 ctcagggggtt ctgttctggc ctgcggccct ggatcgtcca gctgggtcg gggtggggag     120 cagacctcgc ccttatcggc tggggctgag ggtgagggtc ccgtttcccc aaaggcctag     180
cctggggttc cagccacaag ccctaccggg cagcgcccgg ccccgccccct ccaggcctgg     240 cactcgtcct caaccaagat ggcgcggatg gcttcaggcg catcacgaca ccggcgcgtc     300
acgcgacccg ccctacgggc acctcccgcg ctttttcttag cgccgcagac ggtggtcgag     360
cgggggaccg ggaagctta                                                 379

<210> SEQ ID NO 8
<211> LENGTH: 146
<212> TYPE: DNA
<213> ORGANISM: Unknown
<220> FEATURE:
<223> OTHER INFORMATION: Herpes simplex virus

<400> SEQUENCE: 8

```
atgacacaaa ccccgcccag cgtcttgtca ttggcgaatt cgaacacgca gatgcagtcg      60
gggcggcgcg gtcccaggtc cacttcgcat attaaggtga cgcgtgtggc ctcgaacacc     120
gagcgaccct gcagcgaccc gcttaa                                          146

<210> SEQ ID NO 9
<211> LENGTH: 301
<212> TYPE: DNA
<213> ORGANISM: Unknown
<220> FEATURE:
<223> OTHER INFORMATION: Cytomegalovirus sp.

<400> SEQUENCE: 9
tacataactt acggtaaatg gcccgcctgg ctgaccgccc aacgaccccc gcccattgac      60
gtcaataatg acgtatgttc ccatagtaac gccaataggg actttccatt gacgtcaatg     120
ggtggagtat ttacggtaaa ctgcccactt ggcagtacat caagtgtatc atatgccaag     180
tacgccccct attgacgtca atgacggtaa atggcccgcc tggcattatg cccagtacat     240
gaccttatgg gactttccta cttggcagta catctacgta ttagtcatcg ctattaccat     300
g                                                                     301

<210> SEQ ID NO 10
<211> LENGTH: 97
<212> TYPE: DNA
<213> ORGANISM: Unknown
<220> FEATURE:
<223> OTHER INFORMATION: simian virus 40

<400> SEQUENCE: 10
gtaagtttag tcttttgtc ttttatttca ggtcccggat ccggtggtgg tgcaaatcaa      60
agaactgctc ctcagtggat gttgccttta cttctag                              97

<210> SEQ ID NO 11
<211> LENGTH: 133
<212> TYPE: DNA
<213> ORGANISM: Artificial Sequence
<220> FEATURE:
<223> OTHER INFORMATION: Chimeric Intron

<400> SEQUENCE: 11
gtaagtatca aggttacaag acaggtttaa ggagaccaat agaaactggg cttgtcgaga      60
cagagaagac tcttgcgttt ctgataggca cctattggtc ttactgacat ccactttgcc     120
tttctctcca cag                                                        133

<210> SEQ ID NO 12
<211> LENGTH: 122
<212> TYPE: DNA
<213> ORGANISM: Unknown
<220> FEATURE:
<223> OTHER INFORMATION: simian virus 40

<400> SEQUENCE: 12
taagatacat tgatgagttt ggacaaacca caactagaat gcagtgaaaa aaatgcttta      60
tttgtgaaat ttgtgatgct attgctttat ttgtaaccat tataagctgc aataaacaag     120
tt                                                                    122

<210> SEQ ID NO 13
<211> LENGTH: 56
<212> TYPE: DNA
<213> ORGANISM: Oryctolagus cuniculus
```

<400> SEQUENCE: 13
aataaaggaa atttattttc attgcaatag tgtgttggaa ttttttgtgt ctctca          56

<210> SEQ ID NO 14
<211> LENGTH: 4685
<212> TYPE: DNA
<213> ORGANISM: Artificial Sequence
<220> FEATURE:
<223> OTHER INFORMATION: AAV transfer cassette 1

<400> SEQUENCE: 14
cctgcaggca gctgcgcgct cgctcgctca ctgaggccgc ccgggcaaag cccgggcgtc          60
gggcgacctt tggtcgcccg gcctcagtga gcgagcgagc gcgcagagag ggagtggcca         120
actccatcac taggggttcc ttgcgtcgac tcgaggtgag ccccacgttc tgcttcactc         180
tccccatctc ccccccctcc ccaccccaa tttttgtattt atttattttt taattatttt         240
gtgcagcgat ggggggcgggg gggggggggg ggcgcgcgcc aggcggggcg gggcggggcg         300
aggggcgggg cggggcgagg cggagaggtg cggcggcagc caatcagagc ggcgcgctcc         360
gaaagtttcc ttttatggcg aggcggcggc ggcggcggcc ctataaaaag cgaagcgcgc         420
ggcgggcgat gcatgtaagt ttagtctttt tgtctttat ttcaggtccc ggatccggtg         480
gtggtgcaaa tcaaagaact gctcctcagt ggatgttgcc tttacttcta gcaccggtcg         540
ccaccatgac cgctcgcggc ctggcccttg cctcctcct gctgctactg tgtccagcgc         600
aggtgttttc acagtcctgt gtttggtatg gagagtgtgg aattgcatat ggggacaaga         660
ggtacaattg cgaatattct ggcccaccaa aaccattgcc aaaggatgga tatgacttag         720
tgcaggaact ctgtccagga ttcttctttg gcaatgtcag tctctgttgt gatgttcggc         780
agcttcagac actaaaagac aacctgcagc tgcctctaca gtttctgtcc agatgtccat         840
cctgttttta taacctactg aacctgtttt gtgagctgac atgtagccct cgacagagtc         900
agtttttgaa tgttacagct actgaagatt atgttgatcc tgttacaaac cagacgaaaa         960
caaatgtgaa agagttacaa tactacgtcg gacagagttt tgccaatgca atgtacaatg        1020
cctgccggga tgtggaggcc ccctcaagta atgacaaggc cctgggactc ctgtgtggga        1080
aggacgctga cgcctgtaat gccaccaact ggattgaata catgttcaat aaggacaatg        1140
gacaggcacc ttttaccatc actcctgtgt tttcagattt tccagtccat gggatggagc        1200
ccatgaacaa tgccaccaaa ggctgtgacg agtctgtgga tgaggtcaca gcaccatgta        1260
gctgccaaga ctgctctatt gtctgtggcc ccaagcccca gccccacct cctcctgctc        1320 cctggacgat ccttggcttg gacgccatgt atgtcatcat gtggatcacc tacatggcgt        1380
ttttgcttgt gttttttgga gcattttttg cagtgtggtg ctacagaaaa cggtattttg        1440
tctccgagta cactcccatc gatagcaata tagcttttc tgttaatgca agtgacaaag        1500
gagaggcgtc ctgctgtgac cctgtcagcg cagcatttga gggctgcttg aggcggctgt        1560
tcacacgctg ggggtctttc tgcgtccgaa accctggctg tgtcattttc ttctcgctgg        1620
tcttcattac tgcgtgttcg tcaggcctgg tgtttgtccg ggtcacaacc aatccagttg        1680
acctctggtc agccccagc agccaggctc gcctggaaaa agagtacttt gaccagcact        1740
ttgggccttt cttccggacg gagcagctca tcatccgggc ccctctcact gacaaacaca        1800
tttaccagcc ataccccttcg ggagctgatg tacccttttgg acctccgctt gacatacaga        1860
tactgcacca ggttcttgac ttacaaatag ccatcgaaaa cattactgcc tcttatgaca        1920

-continued

```
atgagactgt gacacttcaa gacatctgct tggcccctct ttcaccgtat aacacgaact    1980
gcaccatttt gagtgtgtta aattacttcc agaacagcca ttccgtgctg gaccacaaga    2040
aaggggacga cttctttgtg tatgccgatt accacacgca ctttctgtac tgcgtacggg    2100
ctcctgcctc tctgaatgat acaagtttgc tccatgaccc ttgtctgggt acgtttggtg    2160
gaccagtgtt cccgtggctt gtgttgggag gctatgatga tcaaaactac aataacgcca    2220
ctgcccttgt gattaccttc cctgtcaata attactataa tgatacagag aagctccaga    2280
gggcccaggc ctgggaaaaa gagtttatta attttgtgaa aaactacaag aatcccaatc    2340
tgaccatttc cttcactgct gaacgaagta ttgaagatga actaaatcgt gaaagtgaca    2400
gtgatgtctt caccgttgta attagctatg ccatcatgtt tctatatatt tccctagcct    2460
tggggcacat caaaagctgt cgcaggcttc tggtggattc gaaggtctca ctaggcatcg    2520
cgggcatctt gatcgtgctg agctcggtgg cttgctcctt gggtgtcttc agctacattg    2580 ggttgcccatt gaccctcatt gtgattgaag tcatcccgtt cctggtgctg gctgttggag    2640
tggacaacat cttcattctg gtgcaggcct accagagaga tgaacgtctt caaggggaaa    2700
ccctggatca gcagctgggc agggtcctag gagaagtggc tcccagtatg ttcctgtcat    2760
ccttttctga gactgtagca ttttttctag gagcattgtc cgtgatgcca gccgtgcaca    2820
ccttctctct ctttgcggga ttggcagtct tcattgactt tcttctgcag attacctgtt    2880
tcgtgagtct cttggggtta gacattaaac gtcaagagaa aaatcggcta gacatctttt    2940
gctgtgtcag aggtgctgaa gatggaacaa gcgtccaggc ctcagagagc tgtttgtttc    3000
gcttcttcaa aaactcctat tctccacttc tgctaaagga ctggatgaga ccaattgtga    3060
tagcaatatt tgtgggtgtt ctgtcattca gcatcgcagt cctgaacaaa gtagatattg    3120
gattggatca gtctctttcg atgccagatg actcctacat ggtggattat ttcaaatcca    3180
tcagtcagta cctgcatgcg ggtccgcctg tgtactttgt cctggaggaa gggcacgact    3240
acacttcttc caaggggcag aacatggtgt gcggcggcat gggctgcaac aatgattccc    3300
tggtgcagca gatatttaac gcggcgcagc tggacaacta tacccgaata ggcttcgccc    3360
cctcgtcctg gatcgacgat tatttcgact gggtgaagcc acagtcgtct tgctgtcgag    3420
tggacaatat cactgaccag ttctgcaatg cttcagtggt tgaccctgcc tgcgttcgct    3480
gcaggcctct gactccggaa ggcaaacaga ggcctcaggg gggagacttc atgagattcc    3540
tgcccatgtt cctttcggat aaccctaacc ccaagtgtgg caaaggggga catgctgcct    3600
atagttctgc agttaacatc ctccttggcc atggcaccag ggtcggagcc acgtacttca    3660
tgacctacca caccgtgctg cagacctctg ctgactttat tgacgctctg aagaaagccc    3720 gactatagc cagtaatgtc accgaaacca tgggcattaa cggcagtgcc taccgagtat    3780
ttccttacag tgtgtttat gtcttctacg aacagtacct gaccatcatt gacgacacta    3840
tcttcaacct cggtgtgtcc ctgggcgcga tatttctggt gaccatggtc ctcctgggct    3900
gtgagctctg gtctgcagtc atcatgtgtg ccaccatcgc catggtcttg gtcaacatgt    3960
ttggagttat gtggctctgg ggcatcagtc tgaacgctgt atccttggtc aacctggtga    4020
tgagctgtgg catctccgtg gagttctgca gccacataac cagagcgttc acggtgagca    4080
tgaaaggcag ccgcgtggag cgcgcggaag aggcacttgc ccacatgggc agctccgtgt    4140
tcagtggaat cacacttaca aaatttggag ggattgtggt gttggctttt gccaaatctc    4200 aaatttttcca gatattctac ttcaggatgt atttggccat ggtcttactg ggagccactc    4260
acggattaat atttctccct gtcttactca gttacatagg gccatcagta aataaagcca    4320
```
aaagttgtgc cactgaagag cgatacaaag gaacagagcg cgaacggctt ctaaatttct      4380
aggtttaaac aagctttaag atacattgat gagtttggac aaaccacaac tagaatgcag      4440
tgaaaaaaat gctttatttg tgaaatttgt gatgctattg ctttatttgt aaccattata      4500
agctgcaata aacaagttct cgagccatgg gcgcgccatc gatgaggaac ccctagtgat      4560
ggagttggcc actccctctc tgcgcgctcg ctcgctcact gaggccgggc gaccaaaggt      4620
cgcccgacgc ccgggctttg cccgggcggc ctcagtgagc gagcgagcgc gcagctgcct      4680
gcagg                                                                  4685

<210> SEQ ID NO 15
<211> LENGTH: 4617
<212> TYPE: DNA
<213> ORGANISM: Artificial Sequence
<220> FEATURE:
<223> OTHER INFORMATION: AAV transfer cassette 2

<400> SEQUENCE: 15
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc ttgcgtcgac cggctggggc tgagggtgag ggtcccgttt       180
ccccaaaggc ctagcctggg gttccagcca caagccctac cgggcagcgc ccggccccgc       240
ccctccaggc ctggcactcg tcctcaacca agatggcgcg gatggcttca ggcgcatcac       300
gacaccggcg cgtcacgcga cccgccctac gggcacctcc cgcgcttttc ttagcgccgc       360
agacggtggc cgagcggggg accgggaagc atgcatgtaa gtatcaaggt tacaagacag       420
gtttaaggag accaatagaa actgggcttg tcgagacaga gaagactctt gcgtttctga       480
taggcaccta ttggtcttac tgacatccac tttgcctttc tctccacagc accggtcgcc       540
accatgaccg ctcgcggcct ggcccttggc ctcctcctgc tgctactgtg tccagcgcag       600 gtgtttttcac agtcctgtgt ttggtatgga gagtgtggaa ttgcatatgg ggacaagagg       660
tacaattgcg aatattctgg cccaccaaaa ccattgccaa aggatggata tgacttagtg       720
caggaactct gtccaggatt cttctttggc aatgtcagtc tctgttgtga tgttcggcag       780
cttcagacac taaaagacaa cctgcagctg cctctacagt ttctgtccag atgtccatcc       840
tgtttttata acctactgaa cctgtttgt gagctgacat gtagccctcg acagagtcag       900
tttttgaatg ttacagctac tgaagattat gttgatcctg ttacaaacca gacgaaaaca       960
aatgtgaaag agttacaata ctacgtcgga cagagttttg ccaatgcaat gtacaatgcc      1020
tgccgggatg tggaggcccc ctcaagtaat gacaaggccc tgggactcct gtgtgggaag      1080
gacgctgacg cctgtaatgc caccaactgg attgaataca tgttcaataa ggacaatgga      1140
caggcacctt ttaccatcac tcctgtgttt tcagattttc agtccatgg gatggagccc      1200 atgaacaatg ccaccaaagg ctgtgacgag tctgtggatg aggtcacagc accatgtagc      1260
tgccaagact gctctattgt ctgtggcccc aagccccagc ccccacctcc tcctgctccc      1320
tggacgatcc ttggcttgga cgccatgtat gtcatcatgt ggatcaccta catggcgttt      1380
ttgcttgtgt ttttttggagc attttttgca gtgtggtgct acagaaaacg gtattttgtc      1440
tccgagtaca ctcccatcga tagcaatata gctttttctg ttaatgcaag tgacaaagga      1500
gaggcgtcct gctgtgaccc tgtcagcgca gcatttgagg gctgcttgag gcggctgttc      1560
acacgctggg ggtctttctg cgtccgaaac cctggctgtg tcattttctt ctcgctggtc      1620

-continued

```
ttcattactg cgtgttcgtc aggcctggtg tttgtccggg tcacaaccaa tccagttgac      1680
ctctggtcag cccccagcag ccaggctcgc ctggaaaaag agtactttga ccagcacttt      1740
gggcctttct tccggacgga gcagctcatc atccgggccc ctctcactga caaacacatt      1800
taccagccat acccttcggg agctgatgta ccctttggac ctccgcttga catacagata      1860
ctgcaccagg ttcttgactt acaaatagcc atcgaaaaca ttactgcctc ttatgacaat      1920
gagactgtga cacttcaaga catctgcttg gcccctcttt caccgtataa cacgaactgc      1980
accattttga gtgtgttaaa ttacttccag aacagccatt ccgtgctgga ccacaagaaa      2040
ggggacgact tctttgtgta tgccgattac cacacgcact ttctgtactg cgtacgggct      2100
cctgcctctc tgaatgatac aagtttgctc catgacccctt gtctgggtac gtttggtgga      2160
ccagtgttcc cgtggcttgt gttgggaggc tatgatgatc aaaactacaa taacgccact      2220
gcccttgtga ttaccttccc tgtcaataat tactataatg atacagagaa gctccagagg      2280
gcccaggcct gggaaaaaga gtttattaat tttgtgaaaa actacaagaa tcccaatctg      2340
accatttcct tcactgctga acgaagtatt gaagatgaac taaatcgtga aagtgacagt      2400
gatgtcttca ccgttgtaat tagctatgcc atcatgtttc tatatatttc cctagccttg      2460
gggcacatca aaagctgtcg caggcttctg gtggattcga aggtctcact aggcatcgcg      2520
ggcatcttga tcgtgctgag ctcggtggct tgctccttgg gtgtcttcag ctacattggg      2580
ttgcccttga ccctcattgt gattgaagtc atcccgttcc tggtgctggc tgttggagtg      2640
gacaacatct tcattctggt gcaggcctac cagagagatg aacgtcttca aggggaaacc      2700
ctggatcagc agctgggcag ggtcctagga gaagtggctc ccagtatgtt cctgtcatcc      2760
ttttctgaga ctgtagcatt tttcttagga gcattgtccg tgatgccagc cgtgcacacc      2820
ttctctctct ttgcgggatt ggcagtcttc attgactttc ttctgcagat tacctgtttc      2880
gtgagtctct gggggttaga cattaaacgt caagagaaaa atcggctaga catcttttgc      2940
tgtgtcagag gtgctgaaga tggaacaagc gtccaggcct cagagagctg tttgtttcgc      3000
ttcttcaaaa actcctattc tccacttctg ctaaaggact ggatgagacc aattgtgata      3060
gcaatatttg tgggtgttct gtcattcagc atcgcagtcc tgaacaaagt agatattgga      3120
ttggatcagt ctctttcgat gccagatgac tcctacatgg tggattattt caaatccatc      3180
agtcagtacc tgcatgcggg tccgcctgtg tactttgtcc tggaggaagg cacgactac      3240 acttcttcca aggggcagaa catggtgtgc ggcggcatgg gctgcaacaa tgattccctg      3300
gtgcagcaga tatttaacgc ggcgcagctg gacaactata cccgaatagg cttcgccccc      3360
tcgtcctgga tcgacgatta tttcgactgg gtgaagccac agtcgtcttg ctgtcgagtg      3420
gacaatatca ctgaccagtt ctgcaatgct tcagtggttg accctgcctg cgttcgctgc      3480
aggcctctga ctccggaagg caaacagagg cctcagggg gagacttcat gagattcctg      3540
cccatgttcc tttcggataa ccctaacccc aagtgtggca aggggggaca tgctgcctat      3600
agttctgcag ttaacatcct ccttggccat ggcaccaggg tcggagccac gtacttcatg      3660
acctaccaca ccgtgctgca gacctctgct gactttattg acgctctgaa gaaagcccga      3720
cttatagcca gtaatgtcac cgaaaccatg ggcattaacg gcagtgccta ccgagtattt      3780
ccttacagtg tgttttatgt cttctacgaa cagtacctga ccatcattga cgacactatc      3840
ttcaacctcg gtgtgtccct gggcgcgata tttctggtga ccatggtcct cctgggctgt      3900
gagctctggt ctgcagtcat catgtgtgcc accatcgcca tggtcttggt caacatgttt      3960
ggagttatgt ggctctgggg catcagtctg aacgctgtat ccttggtcaa cctggtgatg      4020
```

-continued

```
agctgtggca tctccgtgga gttctgcagc cacataacca gagcgttcac ggtgagcatg    4080
aaaggcagcc gcgtggagcg cgcggaagag gcacttgccc acatgggcag ctccgtgttc    4140
agtggaatca cacttacaaa atttggaggg attgtggtgt tggctttttgc caaatctcaa    4200 attttccaga tattctactt caggatgtat ttggccatgg tcttactggg agccactcac    4260
ggattaatat ttctccctgt cttactcagt tacatagggc catcagtaaa taaagccaaa    4320
agttgtgcca ctgaagagcg atacaaagga acagagcgcg aacggcttct aaatttctag    4380
gtttaaacaa gcttaataaa ggaaatttat tttcattgca atagtgtgtt ggaattttttt    4440 gtgtctctca ctcgagccat gggcgcgcca tcgatgagga accccctagtg atggagttgg    4500 ccactccctc tctgcgcgct cgctcgctca ctgaggccgg gcgaccaaag gtcgcccgac    4560
gcccgggctt tgcccgggcg gcctcagtga gcgagcgagc gcgcagctgc ctgcagg      4617
```

<210> SEQ ID NO 16
<211> LENGTH: 4720
<212> TYPE: DNA
<213> ORGANISM: Artificial Sequence
<220> FEATURE:
<223> OTHER INFORMATION: AAV Transfer Cassette 3

<400> SEQUENCE: 16

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc ttgcgtcgac attcctgctg ggaaaagcaa gtggaggtgc     180
tccttgaaga aacaggggga tcccaccgat ctcaggggtt ctgttctggc ctgcggccct     240
ggatcgtcca gcctgggtcg gggtggggag cagacctcgc ccttatcggc tggggctgag     300
ggtgagggtc ccgtttcccc aaaggcctag cctggggttc cagccacaag ccctaccggg     360
cagcgcccgg ccccgccct ccaggcctgg cactcgtcct caaccaagat ggcgcggatg     420
gcttcaggcg catcacgaca ccggcgcgtc acgcgacccg ccctacgggc acctcccgcg     480 ctttttcttag cgccgcagac ggtggtcgag cgggggaccg ggaagcttaa tgcatgtaag     540
tttagtcttt ttgtctttta tttcaggtcc cggatccggt ggtggtgcaa atcaaagaac     600
tgctcctcag tggatgttgc ctttacttct agcaccggtc gccaccatga ccgctcgcgg     660
cctggccctt ggcctcctcc tgctgctact gtgtccagcg caggtgtttt cacagtcctg     720
tgtttggtat ggagagtgtg gaattgcata tggggacaag aggtacaatt gcgaatattc     780
tggcccacca aaaccattgc caaaggatgg atatgactta gtgcaggaac tctgtccagg     840
attcttcttt ggcaatgtca gtctctgttg tgatgttcgg cagcttcaga cactaaaaga     900
caacctgcag ctgcctctac agtttctgtc cagatgtcca tcctgttttt ataacctact     960
gaacctgttt tgtgagctga catgtagccc tcgacagagt cagtttttga atgttacagc    1020
tactgaagat tatgttgatc ctgttacaaa ccagacgaaa acaaatgtga aagagttaca    1080
atactacgtc ggacagagtt ttgccaatgc aatgtacaat gcctgccggg atgtggaggc    1140
cccctcaagt aatgacaagg ccctgggact cctgtgtggg aaggacgctg acgcctgtaa    1200
tgccaccaac tggattgaat acatgttcaa taaggacaat ggacaggcac cttttaccat    1260
cactcctgtg ttttcagatt ttccagtcca tgggatggag cccatgaaca atgccaccaa    1320 aggtgtgac gagtctgtgg atgaggtcac agcaccatgt agctgccaag actgctctat    1380
tgtctgtggc cccaagcccc agcccccacc tcctcctgct ccctggacga tccttggctt    1440
```

-continued

```
ggacgccatg tatgtcatca tgtggatcac ctacatggcg tttttgcttg tgttttttgg    1500
agcatttttt gcagtgtggt gctacagaaa acggtatttt gtctccgagt acactcccat    1560
cgatagcaat atagcttttt ctgttaatgc aagtgacaaa ggagaggcgt cctgctgtga    1620
ccctgtcagc gcagcatttg agggctgctt gaggcggctg ttcacacgct gggggtcttt    1680
ctgcgtccga aaccctggct gtgtcatttt cttctcgctg gtcttcatta ctgcgtgttc    1740
gtcaggcctg gtgtttgtcc gggtcacaac caatccagtt gacctctggt cagcccccag    1800
cagccaggct cgcctggaaa aagagtactt tgaccagcac tttgggcctt tcttccggac    1860
ggagcagctc atcatccggg cccctctcac tgacaaacac atttaccagc cataccttc     1920 gggagctgat gtacccttg gacctccgct tgacatacag atactgcacc aggttcttga     1980
cttacaaata gccatcgaaa acattactgc ctcttatgac aatgagactg tgacacttca    2040
agacatctgc ttggcccctc tttcaccgta taacacgaac tgcaccattt tgagtgtgtt    2100
aaattacttc cagaacagcc attccgtgct ggaccacaag aaagggggacg acttctttgt   2160 gtatgccgat taccacacgc actttctgta ctgcgtacgg gctcctgcct ctctgaatga    2220
tacaagtttg ctccatgacc cttgtctggg tacgtttggt ggaccagtgt cccgtggct    2280 tgtgttggga ggctatgatg atcaaaacta caataacgcc actgcccttg tgattacctt    2340
ccctgtcaat aattactata atgatacaga gaagctccag agggcccagg cctgggaaaa    2400
agagtttatt aattttgtga aaaactacaa gaatcccaat ctgaccattt ccttcactgc    2460
tgaacgaagt attgaagatg aactaaatcg tgaaagtgac agtgatgtct tcaccgttgt    2520
aattagctat gccatcatgt ttctatatat ttccctagcc ttggggcaca tcaaaagctg    2580
tcgcaggctt ctggtggatt cgaaggtctc actaggcatc gcgggcatct tgatcgtgct    2640
gagctcggtg gcttgctcct tgggtgtctt cagctacatt gggttgccct tgaccctcat    2700
tgtgattgaa gtcatcccgt cctggtgct ggctgttgga gtggacaaca tcttcattct     2760
ggtgcaggcc taccagagag atgaacgtct tcaaggggaa accctggatc agcagctggg    2820
cagggtccta ggagaagtgg ctcccagtat gttcctgtca tcctttttctg agactgtagc    2880 attttttctta ggagcattgt ccgtgatgcc agccgtgcac accttctctc tctttgcggg    2940
attggcagtc ttcattgact ttcttctgca gattacctgt ttcgtgagtc tcttggggtt    3000
agacattaaa cgtcaagaga aaaatcggct agacatcttt tgctgtgtca gaggtgctga    3060
agatggaaca agcgtccagg cctcagagag ctgtttgttt cgcttcttca aaaactccta    3120
ttctccactt ctgctaaagg actggatgag accaattgtg atagcaatat ttgtgggtgt    3180
tctgtcattc agcatcgcag tcctgaacaa agtagatatt ggattggatc agtctctttc    3240
gatgccagat gactcctaca tggtggatta tttcaaatcc atcagtcagt acctgcatgc    3300
gggtccgcct gtgtactttg tcctggagga aagggcacgac tacacttctt ccaaggggca    3360
gaacatggtg tgcggcggca tgggctgcaa caatgattcc ctggtgcagc agatatttaa    3420
cgcggcgcag ctggacaact atacccgaat aggcttcgcc ccctcgtcct ggatcgacga    3480
ttatttcgac tgggtgaagc acagtcgtc ttgctgtcga gtggacaata tcactgacca     3540
gttctgcaat gcttcagtgg ttgaccctgc ctgcgttcgc tgcaggcctc tgactccgga    3600
aggcaaacag aggcctcagg ggggagactt catgagattc ctgcccatgt ccttttcgga    3660
taaccctaac cccaagtgtg caaagggggg acatgctgcc tatagttctg cagttaacat    3720
cctccttggc catggcacca gggtcggagc cacgtacttc atgacctacc acaccgtgct    3780
gcagacctct gctgacttta ttgacgctct gaagaaagcc cgacttatag ccagtaatgt    3840
```

-continued

```
caccgaaacc atgggcatta acggcagtgc ctaccgagta tttccttaca gtgtgtttta    3900
tgtcttctac gaacagtacc tgaccatcat tgacgacact atcttcaacc tcggtgtgtc    3960
cctgggcgcg atatttctgg tgaccatggt cctcctgggc tgtgagctct ggtctgcagt    4020
catcatgtgt gccaccatcg ccatggtctt ggtcaacatg tttggagtta tgtggctctg    4080
gggcatcagt ctgaacgctg tatccttggt caacctggtg atgagctgtg gcatctccgt    4140
ggagttctgc agccacataa ccagagcgtt cacggtgagc atgaaaggca gccgcgtgga    4200
gcgcgcggaa gaggcacttg cccacatggg cagctccgtg ttcagtggaa tcacacttac    4260
aaaatttgga gggattgtgg tgttggcttt tgccaaatct caaattttcc agatattcta    4320
cttcaggatg tatttggcca tggtcttact gggagccact cacggattaa tatttctccc    4380
tgtcttactc agttacatag ggccatcagt aaataaagcc aaaagttgtg ccactgaaga    4440
gcgatacaaa ggaacagagc gcgaacggct tctaaatttc taggtttaaa caagcttaat    4500
aaaggaaatt tattttcatt gcaatagtgt gttggaattt tttgtgtctc tcactcgagc    4560
catgggcgcg ccatcgatga ggaacccta gtgatggagt tggccactcc ctctctgcgc    4620
gctcgctcgc tcactgaggc cgggcgacca aaggtcgccc gacgcccggg ctttgcccgg    4680
gcggcctcag tgagcgagcg agcgcgcagc tgcctgcagg              4720
```

<210> SEQ ID NO 17
<211> LENGTH: 4683
<212> TYPE: DNA
<213> ORGANISM: Artificial Sequence
<220> FEATURE:
<223> OTHER INFORMATION: AAV transfer casette 4

<400> SEQUENCE: 17

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc ttgcgtcgac cggctggggc tgagggtgag ggtcccgttt     180
ccccaaaggc ctagcctggg gttccagcca caagccctac cgggcagcgc ccggccccgc     240
ccctccaggc ctggcactcg tcctcaacca agatggcgcg gatggcttca ggcgcatcac     300
gacaccggcg cgtcacgcga cccgccctac gggcacctcc cgcgcttttc ttagcgccgc     360
agacggtggc cgagcggggg accgggaagc atgcatgtaa gtatcaaggt tacaagacag     420
gtttaaggag accaatagaa actgggcttg tcgagacaga gaagactctt gcgtttctga     480
taggcaccta ttggtcttac tgacatccac tttgcctttc tctccacagc accggtcgcc     540
accatgaccg ctcgcggcct ggccttggc ctcctcctgc tgctactgtg tccagcgcag     600
gtgttttcac agtcctgtgt ttggtatgga gagtgtggaa ttgcatatgg ggacaagagg     660
tacaattgcg aatattctgg cccaccaaaa ccattgccaa aggatggata tgacttagtg     720
caggaactct gtccaggatt cttctttggc aatgtcagtc tctgttgtga tgttcggcag     780
cttcagacac taaaagacaa cctgcagctg cctctacagt ttctgtccag atgtccatcc     840 tgttttttata acctactgaa cctgtttttgt gagctgacat gtagccctcg acagagtcag     900
tttttgaatg ttacagctac tgaagattat gttgatcctg ttacaaacca gacgaaaaca     960
aatgtgaaag agttacaata ctacgtcgga cagagttttg ccaatgcaat gtacaatgcc    1020
tgccgggatg tggaggcccc ctcaagtaat gacaaggccc tgggactcct gtgtgggaag    1080
gacgctgacg cctgtaatgc caccaactgg attgaataca tgttcaataa ggacaatgga    1140
```

-continued

```
caggcacctt ttaccatcac tcctgtgttt tcagattttc cagtccatgg gatggagccc   1200
atgaacaatg ccaccaaagg ctgtgacgag tctgtggatg aggtcacagc accatgtagc   1260
tgccaagact gctctattgt ctgtggcccc aagccccagc ccccacctcc tcctgctccc   1320
tggacgatcc ttggcttgga cgccatgtat gtcatcatgt ggatcaccta catggcgttt   1380
ttgcttgtgt ttttttggagc atttttttgca gtgtggtgct acagaaaacg gtattttgtc   1440
tccgagtaca ctcccatcga tagcaatata gcttttttctg ttaatgcaag tgacaaagga   1500
gaggcgtcct gctgtgaccc tgtcagcgca gcatttgagg gctgcttgag gcggctgttc   1560
acacgctggg ggtctttctg cgtccgaaac cctggctgtg tcattttctt ctcgctggtc   1620
ttcattactg cgtgttcgtc aggcctggtg tttgtccggg tcacaaccaa tccagttgac   1680
ctctggtcag cccccagcag ccaggctcgc ctggaaaaag agtactttga ccagcacttt   1740 gggccttttct tccggacgga gcagctcatc atccgggccc ctctcactga caaacacatt   1800
taccagccat acccttcggg agctgatgta ccctttggac ctccgcttga catacagata   1860
ctgcaccagg ttcttgactt acaaatagcc atcgaaaaca ttactgcctc ttatgacaat   1920
gagactgtga cacttcaaga catctgcttg gccctctttt caccgtataa cacgaactgc   1980 accatttttga gtgtgttaaa ttacttccag aacagccatt ccgtgctgga ccacaagaaa   2040
ggggacgact tctttgtgta tgccgattac cacacgcact ttctgtactg cgtacgggct   2100
cctgcctctc tgaatgatac aagtttgctc catgaccctt gtctgggtac gtttggtgga   2160
ccagtgttcc cgtggcttgt gttgggaggc tatgatgatc aaaactacaa taacgccact   2220
gcccttgtga ttaccttccc tgtcaataat tactataatg atacagagaa gctccagagg   2280
gcccaggcct gggaaaaaga gtttattaat tttgtgaaaa actacaagaa tcccaatctg   2340
accatttcct tcactgctga acgaagtatt gaagatgaac taaatcgtga aagtgacagt   2400
gatgtcttca ccgttgtaat tagctatgcc atcatgtttc tatatatttc cctagccttg   2460
gggcacatca aaagctgtcg caggcttctg gtggattcga aggtctcact aggcatcgcg   2520
ggcatcttga tcgtgctgag ctcggtggct tgctccttgg gtgtcttcag ctacattggg   2580
ttgcccttga ccctcattgt gattgaagtc atcccgttcc tggtgctggc tgttggagtg   2640
gacaacatct tcattctggt gcaggcctac cagagagatg aacgtcttca aggggaaacc   2700
ctggatcagc agctgggcag ggtcctagga gaagtggctc ccagtatgtt cctgtcatcc   2760
ttttctgaga ctgtagcatt tttcttagga gcattgtccg tgatgccagc cgtgcacacc   2820
ttctctctct ttgcgggatt ggcagtcttc attgactttc ttctgcagat tacctgtttc   2880
gtgagtctct ggggttaga cattaaacgt caagagaaaa atcggctaga catcttttgc   2940
tgtgtcagag gtgctgaaga tggaacaagc gtccaggcct cagagagctg tttgtttcgc   3000
ttcttcaaaa actcctattc tccacttctg ctaaaggact ggatgagacc aattgtgata   3060
gcaatatttg tgggtgttct gtcattcagc atcgcagtcc tgaacaaagt agatattgga   3120
ttggatcagt ctctttcgat gccagatgac tcctacatgg tggattattt caaatccatc   3180
agtcagtacc tgcatgcggg tccgcctgtg tactttgtcc tggaggaagg gcacgactac   3240
acttcttcca aggggcagaa catggtgtgc ggcggcatgg gctgcaacaa tgattccctg   3300
gtgcagcaga tatttaacgc ggcgcagctg gacaactata cccgaatagg cttcgcccc   3360 tcgtcctgga tcgacgatta tttcgactgg gtgaagccac agtcgtcttg ctgtcgagtg   3420
gacaatatca ctgaccagtt ctgcaatgct tcagtggttg accctgcctg cgttcgctgc   3480
aggcctctga ctccggaagg caaacagagg cctcagggg gagacttcat gagattcctg   3540
```

```
cccatgttcc tttcggataa ccctaacccc aagtgtggca aagggggaca tgctgcctat   3600
agttctgcag ttaacatcct ccttggccat ggcaccaggg tcggagccac gtacttcatg   3660
acctaccaca ccgtgctgca gacctctgct gactttattg acgctctgaa gaaagcccga   3720
cttatagcca gtaatgtcac cgaaaccatg ggcattaacg gcagtgccta ccgagtattt   3780
ccttacagtg tgttttatgt cttctacgaa cagtacctga ccatcattga cgacactatc   3840
ttcaacctcg gtgtgtccct gggcgcgata tttctggtga ccatggtcct cctgggctgt   3900
gagctctggt ctgcagtcat catgtgtgcc accatcgcca tggtcttggt caacatgttt   3960
ggagttatgt ggctctgggg catcagtctg aacgctgtat ccttggtcaa cctggtgatg   4020
agctgtggca tctccgtgga gttctgcagc cacataacca gagcgttcac ggtgagcatg   4080
aaaggcagcc gcgtggagcg cgcggaagag gcacttgccc acatgggcag ctccgtgttc   4140
agtggaatca cacttacaaa atttggaggg attgtggtgt tggctttttgc caaatctcaa   4200 attttccaga tattctactt caggatgtat ttggccatgg tcttactggg agccactcac   4260
ggattaatat ttctccctgt cttactcagt tacatagggc catcagtaaa taaagccaaa   4320
agttgtgcca ctgaagagcg atacaaagga acagagcgcg aacggcttct aaatttctag   4380
gtttaaacaa gctttaagat acattgatga gtttggacaa accacaacta gaatgcagtg   4440
aaaaaaatgc tttatttgtg aaatttgtga tgctattgct ttatttgtaa ccattataag   4500
ctgcaataaa caagttctcg agccatgggc gcgccatcga tgaggaaccc ctagtgatgg   4560
agttggccac tccctctctg cgcgctcgct cgctcactga ggccgggcga ccaaaggtcg   4620
cccgacgccc gggctttgcc cggcggcct cagtgagcga gcgagcgcgc agctgcctgc   4680
agg                                                                4683
```

```
<210> SEQ ID NO 18
<211> LENGTH: 4663
<212> TYPE: DNA
<213> ORGANISM: Artificial Sequence
<220> FEATURE:
<223> OTHER INFORMATION: AAV Transfer Casette 5

<400> SEQUENCE: 18
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc ttgcgtcgac cggctggggc tgagggtgag ggtcccgttt    180
ccccaaaggc ctagcctggg gttccagcca caagccctac cgggcagcgc ccggccccgc    240
ccctccaggc ctggcactcg tcctcaacca agatggcgcg gatggcttca ggcgcatcac    300
gacaccggcg cgtcacgcga cccgccctac gggcacctcc cgcgctttttc ttagcgccgc    360 agacggtggc cgagcggggg accgggaagc atgcatgtaa gtttagtctt tttgtctttt    420
atttcaggtc ccggatccgg tggtggtgca aatcaaagaa ctgctcctca gtggatgttg    480
cctttacttc tagcaccggt cgccaccatg accgctcgcg gcctggccct tatgaccgct    540
cgcggccggc ctcctcctgc tgctactgtg tccagcgcag gtgttttcac agtcctgtgt    600
ttggtatgga gagtgtggaa ttgcatatgg ggacaagagg tacaattgcg aatattctgg    660
cccaccaaaa ccattgccaa aggatggata tgacttagtg caggaactct gtccaggatt    720
cttctttggc aatgtcagtc tctgttgtga tgttcggcag cttcagacac taaaagacaa    780
cctgcagctg cctctacagt ttctgtccag atgtccatcc tgttttttata acctactgaa    840
```

-continued

```
cctgttttgt gagctgacat gtagccctcg acagagtcag tttttgaatg ttacagctac      900
tgaagattat gttgatcctg ttacaaacca gacgaaaaca aatgtgaaag agttacaata      960
ctacgtcgga cagagttttg ccaatgcaat gtacaatgcc tgccgggatg tggaggcccc     1020
ctcaagtaat gacaaggccc tgggactcct gtgtgggaag gacgctgacg cctgtaatgc     1080
caccaactgg attgaataca tgttcaataa ggacaatgga caggcacctt ttaccatcac     1140
tcctgtgttt tcagattttc cagtccatgg gatggagccc atgaacaatg ccaccaaagg     1200
ctgtgacgag tctgtggatg aggtcacagc accatgtagc tgccaagact gctctattgt     1260
ctgtggcccc aagccccagc ccccacctcc tcctgctccc tggacgatcc ttggcttgga     1320
cgccatgtat gtcatcatgt ggatcaccta catggcgttt ttgcttgtgt tttttggagc     1380
attttttgca gtgtggtgct acagaaaacg gtattttgtc tccgagtaca ctcccatcga     1440
tagcaatata gctttttctg ttaatgcaag tgacaaagga gaggcgtcct gctgtgaccc     1500
tgtcagcgca gcatttgagg gctgcttgag gcggctgttc acacgctggg ggtctttctg     1560
cgtccgaaac cctggctgtg tcattttctt ctcgctggtc ttcattactg cgtgttcgtc     1620
aggcctggtg tttgtccggg tcacaaccaa tccagttgac ctctggtcag cccccagcag     1680
ccaggctcgc ctggaaaaag agtactttga ccagcacttt gggcctttct tccggacgga     1740
gcagctcatc atccgggccc ctctcactga caaacacatt taccagccat acccttcggg     1800
agctgatgta ccctttggac ctccgcttga catacagata ctgcaccagg ttcttgactt     1860
acaaatagcc atcgaaaaca ttactgcctc ttatgacaat gagactgtga cacttcaaga     1920
catctgcttg gcccctcttt caccgtataa cacgaactgc accattttga gtgtgttaaa     1980
ttacttccag aacagccatt ccgtgctgga ccacaagaaa ggggacgact tctttgtgta     2040
tgccgattac cacacgcact ttctgtactg cgtacgggct cctgcctctc tgaatgatac     2100
aagtttgctc catgacccctt gtctgggtac gtttggtgga ccagtgttcc cgtggcttgt     2160
gttgggaggc tatgatgatc aaaactacaa taacgccact gcccttgtga ttaccttccc     2220
tgtcaataat tactataatg atacagagaa gctccagagg gcccaggcct gggaaaaaga     2280
gtttattaat tttgtgaaaa actacaagaa tcccaatctg accatttcct tcactgctga     2340
acgaagtatt gaagatgaac taaatcgtga aagtgacagt gatgtcttca ccgttgtaat     2400
tagctatgcc atcatgtttc tatatatttc cctagccttg gggcacatca aaagctgtcg     2460
caggcttctg gtggattcga aggtctcact aggcatcgcg ggcatcttga tcgtgctgag     2520
ctcggtggct tgctccttgg gtgtgtcttcag ctacattggg ttgcccttga ccctcattgt     2580
gattgaagtc atcccgttcc tggtgctggc tgttggagtg gacaacatct tcattctggt     2640
gcaggcctac cagagagatg aacgtcttca aggggaaacc ctggatcagc agctgggcag     2700
ggtcctagga gaagtggctc ccagtatgtt cctgtcatcc ttttctgaga ctgtagcatt     2760
tttcttagga gcattgtccg tgatgccagc cgtgcacacc ttctctctct ttgcgggatt     2820
ggcagtcttc attgactttc ttctgcagat tacctgtttc gtgagtctct ggggttaga     2880 cattaaacgt caagagaaaa atcggctaga catcttttgc tgtgtcagag gtgctgaaga     2940
tggaacaagc gtccaggcct cagagagctg tttgtttcgc ttcttcaaaa actcctattc     3000
tccacttctg ctaaaggact ggatgagacc aattgtgata gcaatatttg tgggtgttct     3060
gtcattcagc atcgcagtcc tgaacaaagt agatattgga ttggatcagt ctctttcgat     3120
gccagatgac tcctacatgg tggattattt caaatccatc agtcagtacc tgcatgcggg     3180
tccgcctgtg tactttgtcc tggaggaagg gcacgactac acttcttcca aggggcagaa     3240
```

-continued

```
catggtgtgc ggcggcatgg gctgcaacaa tgattccctg gtgcagcaga tatttaacgc      3300
ggcgcagctg gacaactata cccgaatagg cttcgccccc tcgtcctgga tcgacgatta      3360
tttcgactgg gtgaagccac agtcgtcttg ctgtcgagtg acaatatca ctgaccagtt      3420 ctgcaatgct tcagtggttg accctgcctg cgttcgctgc aggcctctga ctccggaagg      3480
caaacagagg cctcaggggg gagacttcat gagattcctg cccatgttcc tttcggataa      3540
ccctaacccc aagtgtggca aaggggggaca tgctgcctat agttctgcag ttaacatcct      3600
ccttggccat ggcaccaggg tcggagccac gtacttcatg acctaccaca ccgtgctgca      3660
gacctctgct gactttattg acgctctgaa gaaagcccga cttatagcca gtaatgtcac      3720
cgaaaccatg ggcattaacg gcagtgccta ccgagtattt ccttacagtg tgtttatgt      3780 cttctacgaa cagtacctga ccatcattga cgacactatc ttcaacctcg gtgtgtccct      3840
gggcgcgata tttctggtga ccatggtcct cctgggctgt gagctctggt ctgcagtcat      3900
catgtgtgcc accatcgcca tggtcttggt caacatgttt ggagttatgt ggctctgggg      3960
catcagtctg aacgctgtat ccttggtcaa cctggtgatg agctgtggca tctccgtgga      4020
gttctgcagc cacataacca gagcgttcac ggtgagcatg aaaggcagcc gcgtggagcg      4080
cgcggaagag gcacttgccc acatgggcag ctccgtgttc agtggaatca cacttacaaa      4140
atttggaggg attgtggtgt tggcttttgc caaatctcaa attttccaga tattctactt      4200
caggatgtat ttggccatgg tcttactggg agccactcac ggattaatat ttctccctgt      4260
cttactcagt tacataggc catcagtaaa taaagccaaa agttgtgcca ctgaagagcg      4320
atacaaagga acagagcgcg aacggcttct aaatttctag gtttaaacaa gctttaagat      4380
acattgatga gtttggacaa accacaacta gaatgcagtg aaaaaaatgc tttatttgtg      4440
aaatttgtga tgctattgct ttatttgtaa ccattataag ctgcaataaa caagttctcg      4500
agccatgggc gcgccatcga tgaggaaccc ctagtgatgg agttggccac tccctctctg      4560
cgcgctcgct cgctcactga ggccgggcga ccaaaggtcg cccgacgccc gggctttgcc      4620
cgggcggcct cagtgagcga gcgagcgcgc agctgcctgc agg      4663
```

<210> SEQ ID NO 19
<211> LENGTH: 4691
<212> TYPE: DNA
<213> ORGANISM: Artificial Sequence
<220> FEATURE:
<223> OTHER INFORMATION: AAV Transfer Casette 6

<400> SEQUENCE: 19

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc ttgcgtcgac tacataactt acggtaaatg gcccgcctgg       180
ctgaccgccc aacgacccccc gcccattgac gtcaataatg acgtatgttc ccatagtaac       240
gccaataggg actttccatt gacgtcaatg ggtggagtat ttacggtaaa ctgcccactt       300
ggcagtacat caagtgtatc atatgccaag tacgccccct attgacgtca atgacggtaa       360
atggcccgcc tggcattatg cccagtacat gaccttatgg gactttccta cttggcagta       420
catctacgta ttagtcatcg ctattaccat ggatgacaca aaccccgccc agcgtcttgt       480
cattggcgaa ttcgaacacg cagatgcagt cggggcggcg cggtcccagg tccacttcgc       540
atattaaggt gacgcgtgtg gcctcgaaca ccgagcgacc ctgcagcgac ccgcttaaat       600
```

-continued

```
gcataccggt cgccaccatg accgctcgcg gcctggccct tggcctcctc ctgctgctac     660
tgtgtccagc gcaggtgttt tcacagtcct gtgtttggta tggagagtgt ggaattgcat     720
atggggacaa gaggtacaat tgcgaatatt ctggcccacc aaaaccattg ccaaaggatg     780
gatatgactt agtgcaggaa ctctgtccag gattcttctt tggcaatgtc agtctctgtt     840
gtgatgttcg gcagcttcag acactaaaag acaacctgca gctgcctcta cagtttctgt     900
ccagatgtcc atcctgtttt tataacctac tgaacctgtt ttgtgagctg acatgtagcc     960
ctcgacagag tcagtttttg aatgttacag ctactgaaga ttatgttgat cctgttacaa    1020
accagacgaa aacaaatgtg aaagagttac aatactacgt cggacagagt tttgccaatg    1080
caatgtacaa tgcctgccgg gatgtggagg ccccctcaag taatgacaag gccctgggac    1140
tcctgtgtgg gaaggacgct gacgcctgta atgccaccaa ctggattgaa tacatgttca    1200
ataaggacaa tggacaggca cctttttacca tcactcctgt gttttcagat tttccagtcc    1260
atgggatgga gcccatgaac aatgccacca aaggctgtga cgagtctgtg gatgaggtca    1320
cagcaccatg tagctgccaa gactgctcta ttgtctgtgg ccccaagccc cagccccac     1380 ctcctcctgc tccctggacg atccttggct tggacgccat gtatgtcatc atgtggatca    1440
cctacatggc gtttttgctt gtgtttttttg gagcattttt tgcagtgtgg tgctacagaa    1500
aacggtattt tgtctccgag tacactccca tcgatagcaa tatagctttt tctgttaatg    1560
caagtgacaa aggagaggcg tcctgctgtg accctgtcag cgcagcattt gagggctgct    1620
tgaggcggct gttcacacgc tgggggtctt tctgcgtccg aaaccctggc tgtgtcattt    1680
tcttctcgct ggtcttcatt actgcgtgtt cgtcaggcct ggtgtttgtc cgggtcacaa    1740
ccaatccagt tgacctctgg tcagccccca gcagccaggc tcgcctggaa aaagagtact    1800
ttgaccagca ctttgggcct ttcttccgga cggagcagct catcatccgg gccctctca     1860 ctgacaaaca catttaccag ccatacctt cgggagctga tgtacccttt ggacctccgc     1920
ttgacataca gatactgcac caggttcttg acttacaaat agccatcgaa aacattactg    1980
cctcttatga caatgagact gtgacacttc aagacatctg cttggcccct ctttcaccgt    2040
ataacacgaa ctgcaccatt ttgagtgtgt taaattactt ccagaacagc cattccgtgc    2100
tggaccacaa gaaaggggac gacttctttg tgtatgccga ttaccacacg cactttctgt    2160
actgcgtacg ggctcctgcc tctctgaatg atacaagttt gctccatgac ccttgtctgg    2220
gtacgtttgg tggaccagtg ttcccgtggc ttgtgttggg aggctatgat gatcaaaact    2280
acaataacgc cactgccctt gtgattacct tccctgtcaa taattactat aatgatacag    2340
agaagctcca gagggcccag gcctgggaaa aagagtttat taattttgtg aaaaactaca    2400
agaatcccaa tctgaccatt tccttcactg ctgaacgaag tattgaagat gaactaaatc    2460
gtgaaagtga cagtgatgtc ttcaccgttg taattagcta tgccatcatg tttctatata    2520
tttccctagc cttggggcac atcaaaagct gtcgcaggct tctggtggat tcgaaggtct    2580
cactaggcat cgcgggcatc ttgatcgtgc tgagctcggt ggcttgctcc ttgggtgtct    2640
tcagctacat ggggttgccc ttgaccctca ttgtgattga agtcatcccg ttcctggtgc    2700
tggctgttgg agtggacaac atcttcattc tggtgcaggc ctaccagaga gatgaacgtc    2760
ttcaagggga aaccctggat cagcagctgg gcagggtcct aggagaagtg gctcccagta    2820
tgttcctgtc atccttttct gagactgtag cattttttctt aggagcattg tccgtgatgc    2880
cagccgtgca caccttctct ctctttgcgg gattggcagt cttcattgac tttcttctgc    2940
agattacctg tttcgtgagt ctcttggggt tagacattaa acgtcaagag aaaaatcggc    3000
```

```
tagacatctt ttgctgtgtc agaggtgctg aagatggaac aagcgtccag gcctcagaga    3060
gctgtttgtt tcgcttcttc aaaaactcct attctccact tctgctaaag gactggatga    3120
gaccaattgt gatagcaata tttgtgggtg ttctgtcatt cagcatcgca gtcctgaaca    3180
aagtagatat tggattggat cagtctcttt cgatgccaga tgactcctac atggtggatt    3240
atttcaaatc catcagtcag tacctgcatg cgggtccgcc tgtgtacttt gtcctggagg    3300
aagggcacga ctacacttct tccaaggggc agaacatggt gtgcggcggc atgggctgca    3360
acaatgattc cctggtgcag cagatattta cgcggcgca gctggacaac tatacccgaa    3420
taggcttcgc cccctcgtcc tggatcgacg attatttcga ctgggtgaag ccacagtcgt    3480
cttgctgtcg agtggacaat atcactgacc agttctgcaa tgcttcagtg gttgaccctg    3540
cctgcgttcg ctgcaggcct ctgactccgg aaggcaaaca gaggcctcag gggggagact    3600
tcatgagatt cctgcccatg ttcctttcgg ataaccctaa ccccaagtgt ggcaaagggg    3660
gacatgctgc ctatagttct gcagttaaca tcctccttgg ccatggcacc agggtcggag    3720
ccacgtactt catgacctac cacaccgtgc tgcagacctc tgctgacttt attgacgctc    3780
tgaagaaagc ccgacttata gccagtaatg tcaccgaaac catgggcatt aacggcagtg    3840
cctaccgagt atttccttac agtgtgtttt atgtcttcta cgaacagtac ctgaccatca    3900
ttgacgacac tatcttcaac ctcggtgtgt ccctgggcgc gatatttctg gtgaccatgg    3960
tcctcctggg ctgtgagctc tggtctgcag tcatcatgtg tgccaccatc gccatggtct    4020
tggtcaacat gtttggagtt atgtggctct ggggcatcag tctgaacgct gtatccttgg    4080
tcaacctggt gatgagctgt ggcatctccg tggagttctg cagccacata accagagcgt    4140
tcacggtgag catgaaaggc agccgcgtgg agcgcgcgga gaggcactt gcccacatgg    4200 gcagctccgt gttcagtgga atcacactta caaaatttgg agggattgtg gtgttggctt    4260
ttgccaaatc tcaaatttc cagatattct acttcaggat gtatttggcc atggtcttac    4320
tgggagccac tcacggatta atatttctcc ctgtcttact cagttacata gggccatcag    4380
taaataaagc caaaagttgt gccactgaag agcgatacaa aggaacagag cgcgaacggc    4440
ttctaaattt ctaggtttaa acaagcttaa taaaggaaat ttattttcat tgcaatagtg    4500
tgttggaatt ttttgtgtct ctcactcgag ccatgggcgc gccatcgatg aggaacccct    4560
agtgatggag ttggccactc cctctctgcg cgctcgctcg ctcactgagg ccgggcgacc    4620
aaaggtcgcc cgacgcccgg gctttgcccg ggcggcctca gtgagcgagc gagcgcgcag    4680
ctgcctgcag g                                                          4691
```

```
<210> SEQ ID NO 20
<211> LENGTH: 1278
<212> TYPE: PRT
<213> ORGANISM: Artificial Sequence
<220> FEATURE:
<223> OTHER INFORMATION: Variant NPC1 protein

<400> SEQUENCE: 20

Met Thr Ala Arg Gly Leu Ala Leu Gly Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
```

-continued

```
           50                    55                    60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
                100                 105                 110

Cys Ser Pro Arg Gln Ser Gln Phe Leu Asn Val Thr Ala Thr Glu Asp
            115                 120                 125

Tyr Val Asp Pro Val Thr Asn Gln Thr Lys Thr Asn Val Lys Glu Leu
    130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
            245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285

Ala Val Trp Cys Tyr Arg Lys Arg Tyr Phe Val Ser Glu Tyr Thr Pro
    290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
            325                 330                 335

Arg Leu Phe Thr Arg Trp Gly Ser Phe Cys Val Arg Asn Pro Gly Cys
        340                 345                 350

Val Ile Phe Phe Ser Leu Val Phe Ile Thr Ala Cys Ser Ser Gly Leu
        355                 360                 365

Val Phe Val Arg Val Thr Thr Asn Pro Val Asp Leu Trp Ser Ala Pro
    370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
            435                 440                 445

Ala Ile Glu Asn Ile Thr Ala Ser Tyr Asp Asn Glu Thr Val Thr Leu
    450                 455                 460

Gln Asp Ile Cys Leu Ala Pro Leu Ser Pro Tyr Asn Thr Asn Cys Thr
465                 470                 475                 480
```

-continued

```
Ile Leu Ser Val Leu Asn Tyr Phe Gln Asn Ser His Ser Val Leu Asp
            485             490             495

His Lys Lys Gly Asp Asp Phe Phe Val Tyr Ala Asp Tyr His Thr His
            500             505             510

Phe Leu Tyr Cys Val Arg Ala Pro Ala Ser Leu Asn Asp Thr Ser Leu
            515             520             525

Leu His Asp Pro Cys Leu Gly Thr Phe Gly Gly Pro Val Phe Pro Trp
            530             535             540

Leu Val Leu Gly Gly Tyr Asp Asp Gln Asn Tyr Asn Asn Ala Thr Ala
545             550             555             560

Leu Val Ile Thr Phe Pro Val Asn Asn Tyr Tyr Asn Asp Thr Glu Lys
            565             570             575

Leu Gln Arg Ala Gln Ala Trp Glu Lys Glu Phe Ile Asn Phe Val Lys
            580             585             590

Asn Tyr Lys Asn Pro Asn Leu Thr Ile Ser Phe Thr Ala Glu Arg Ser
            595             600             605

Ile Glu Asp Glu Leu Asn Arg Glu Ser Asp Ser Asp Val Phe Thr Val
            610             615             620

Val Ile Ser Tyr Ala Ile Met Phe Leu Tyr Ile Ser Leu Ala Leu Gly
625             630             635             640

His Met Lys Ser Cys Arg Arg Leu Leu Val Asp Ser Lys Val Ser Leu
            645             650             655

Gly Ile Ala Gly Ile Leu Ile Val Leu Ser Ser Val Ala Cys Ser Leu
            660             665             670

Gly Val Phe Ser Tyr Ile Gly Leu Pro Leu Thr Leu Ile Val Ile Glu
            675             680             685

Val Ile Pro Phe Leu Val Leu Ala Val Gly Val Asp Asn Ile Phe Ile
            690             695             700

Leu Val Gln Ala Tyr Gln Arg Asp Glu Arg Leu Gln Gly Glu Thr Leu
705             710             715             720

Asp Gln Gln Leu Gly Arg Val Leu Gly Glu Val Ala Pro Ser Met Phe
            725             730             735

Leu Ser Ser Phe Ser Glu Thr Val Ala Phe Phe Leu Gly Ala Leu Ser
            740             745             750

Val Met Pro Ala Val His Thr Phe Ser Leu Phe Ala Gly Leu Ala Val
            755             760             765

Phe Ile Asp Phe Leu Leu Gln Ile Thr Cys Phe Val Ser Leu Leu Gly
            770             775             780

Leu Asp Ile Lys Arg Gln Glu Lys Asn Arg Leu Asp Ile Phe Cys Cys
785             790             795             800

Val Arg Gly Ala Glu Asp Gly Thr Ser Val Gln Ala Ser Glu Ser Cys
            805             810             815

Leu Phe Arg Phe Phe Lys Asn Ser Tyr Ser Pro Leu Leu Leu Lys Asp
            820             825             830

Trp Met Arg Pro Ile Val Ile Ala Ile Phe Val Gly Val Leu Ser Phe
            835             840             845

Ser Ile Ala Val Leu Asn Lys Val Asp Ile Gly Leu Asp Gln Ser Leu
            850             855             860

Ser Met Pro Asp Asp Ser Tyr Met Val Asp Tyr Phe Lys Ser Ile Ser
865             870             875             880

Gln Tyr Leu His Ala Gly Pro Pro Val Tyr Phe Val Leu Glu Glu Gly
            885             890             895
```

-continued

```
His Asp Tyr Thr Ser Ser Lys Gly Gln Asn Met Val Cys Gly Gly Met
        900             905             910

Gly Cys Asn Asn Asp Ser Leu Val Gln Gln Ile Phe Asn Ala Ala Gln
    915             920             925

Leu Asp Asn Tyr Thr Arg Ile Gly Phe Ala Pro Ser Ser Trp Ile Asp
    930             935             940

Asp Tyr Phe Asp Trp Val Lys Pro Gln Ser Ser Cys Cys Arg Val Asp
945             950             955             960

Asn Ile Thr Asp Gln Phe Cys Asn Ala Ser Val Val Asp Pro Ala Cys
            965             970             975

Val Arg Cys Arg Pro Leu Thr Pro Glu Gly Lys Gln Arg Pro Gln Gly
            980             985             990

Gly Asp Phe Met Arg Phe Leu Pro  Met Phe Leu Ser Asp  Asn Pro Asn
            995             1000                1005

Pro Lys  Cys Gly Lys Gly Gly  His Ala Ala Tyr Ser  Ser Ala Val
    1010            1015            1020

Asn Ile  Leu Leu Gly His Gly  Thr Arg Val Gly Ala  Thr Tyr Phe
    1025            1030            1035

Met Thr  Tyr His Thr Val Leu  Gln Thr Ser Ala Asp  Phe Ile Asp
    1040            1045            1050

Ala Leu  Lys Lys Ala Arg Leu  Ile Ala Ser Asn Val  Thr Glu Thr
    1055            1060            1065

Met Gly  Ile Asn Gly Ser Ala  Tyr Arg Val Phe Pro  Tyr Ser Val
    1070            1075            1080

Phe Tyr  Val Phe Tyr Glu Gln  Tyr Leu Thr Ile Ile  Asp Asp Thr
    1085            1090            1095

Ile Phe  Asn Leu Gly Val Ser  Leu Gly Ala Ile Phe  Leu Val Thr
    1100            1105            1110

Met Val  Leu Leu Gly Cys Glu  Leu Trp Ser Ala Val  Ile Met Cys
    1115            1120            1125

Ala Thr  Ile Ala Met Val Leu  Val Asn Met Phe Gly  Val Met Trp
    1130            1135            1140

Leu Trp  Gly Ile Ser Leu Asn  Ala Val Ser Leu Val  Asn Leu Val
    1145            1150            1155

Met Ser  Cys Gly Ile Ser Val  Glu Phe Cys Ser His  Ile Thr Arg
    1160            1165            1170

Ala Phe  Thr Val Ser Met Lys  Gly Ser Arg Val Glu  Arg Ala Glu
    1175            1180            1185

Glu Ala  Leu Ala His Met Gly  Ser Ser Val Phe Ser  Gly Ile Thr
    1190            1195            1200

Leu Thr  Lys Phe Gly Gly Ile  Val Val Leu Ala Phe  Ala Lys Ser
    1205            1210            1215

Gln Ile  Phe Gln Ile Phe Tyr  Phe Arg Met Tyr Leu  Ala Met Val
    1220            1225            1230

Leu Leu  Gly Ala Thr His Gly  Leu Ile Phe Leu Pro  Val Leu Leu
    1235            1240            1245

Ser Tyr  Ile Gly Pro Ser Val  Asn Lys Ala Lys Ser  Cys Ala Thr
    1250            1255            1260

Glu Glu  Arg Tyr Lys Gly Thr  Glu Arg Glu Arg Leu  Leu Asn Phe
    1265            1270            1275
```